(12) United States Patent
Nishiuchi et al.

(10) Patent No.: US 9,034,403 B2
(45) Date of Patent: May 19, 2015

(54) YEAST EXTRACT CONTAINING γ-GLU-X OR γ-GLU-X-GLY AND A METHOD FOR PRODUCING THE SAME

(75) Inventors: Hiroaki Nishiuchi, Kawasaki (JP); Wataru Hoshino, Kawasaki (JP); Junko Yamazaki, Kawasaki (JP); Toshimi Mizukoshi, Kawasaki (JP); Vsevolod Aleksandrovich Serebryanyy, Moscow (RU); Olga Aleksandrovna Sofyanovich, Moscow (RU); Dmitriy Aleksandrovich Cheshev, Moscow (RU); V. Elena Matrosova, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 13/593,974

(22) Filed: Aug. 24, 2012

(65) Prior Publication Data

US 2013/0045305 A1 Feb. 21, 2013

Related U.S. Application Data

(63) Continuation of application No. PCT/JP2011/059480, filed on Apr. 12, 2011.

(30) Foreign Application Priority Data

| Apr. 12, 2010 | (JP) | 2010-091719 |
| Jul. 5, 2010 | (RU) | 2010127403 |
| Sep. 9, 2010 | (JP) | 2010-201962 |

(51) Int. Cl.
*A23L 1/28* (2006.01)
*C12P 21/02* (2006.01)
*C12N 1/16* (2006.01)
*C07K 14/395* (2006.01)
*C12N 1/18* (2006.01)

(52) U.S. Cl.
CPC ............... *C12P 21/02* (2013.01); *C07K 14/395* (2013.01); *C12N 1/18* (2013.01)

(58) Field of Classification Search
CPC ........... A23L 1/28; A23L 1/228; C12P 21/02; C12P 13/14; C12N 1/16; C12N 1/18; C12N 9/1096; C12N 21/02; C07K 16/18
USPC .................. 435/254.2, 254.21; 426/61, 60, 62
See application file for complete search history.

(56) References Cited

U.S. PATENT DOCUMENTS

| 6,013,485 | A | 1/2000 | Jaeger | |
| 6,143,295 | A | 11/2000 | Jaeger | |
| 6,348,335 | B1 | 2/2002 | Jaeger | |
| 7,118,775 | B2 * | 10/2006 | Kohmura et al. | 426/656 |
| 2009/0130282 | A1 | 5/2009 | Hofmann et al. | |
| 2009/0239310 | A1 * | 9/2009 | Ohsu et al. | 436/501 |
| 2009/0246835 | A1 | 10/2009 | Iwatani et al. | |
| 2010/0136197 | A1 | 6/2010 | Eto et al. | |
| 2011/0097805 | A1 | 4/2011 | Ohsu et al. | |

FOREIGN PATENT DOCUMENTS

| EP | 2 251 413 | | 11/2010 |
| JP | 54-157890 | A | 12/1979 |
| JP | 60-75279 | A | 4/1985 |
| JP | 2-295480 | A | 12/1990 |
| JP | 6-16702 | B2 | 3/1994 |
| JP | 8-332081 | A | 12/1996 |
| JP | 2004-113155 | A | 4/2004 |
| JP | 2004-298014 | A | 10/2004 |
| JP | 2008-99578 | A | 5/2008 |
| RU | 2070875 | C1 | 12/1996 |
| WO | WO 2007/042288 | A2 | 4/2007 |
| WO | WO 2007/055388 | A2 | 5/2007 |
| WO | WO 2007/055393 | | 5/2007 |
| WO | WO 2008/139946 | A1 | 11/2008 |
| WO | WO 2009/110624 | | 9/2009 |

OTHER PUBLICATIONS

Wen, S. et al. 2004. Utilization of amino acids to enhance glutathione production in *Saccharomyces cerevisiae*. Enzy. Microbial Technol. 35: 501-507.*
Nisbet, T. M. et al., J. Gen. Microbiol. 115: 127-133 (1979).*
Wiles, A. M. et al. Microbiology, 152: 3133-3145 (2006).*
Alton Meister et al., "Glutathione", Ann. Rev. Biochem., vol. 52, 1983, pp. 711-760.
Hideyuki Suzuki et al., "Use of Bacterial γ-Glutamyltranspeptidase for Enzymatic Synthesis of γ-d-Glutamyl Compounds", Applied and Environmental Microbiology, vol. 69, No. 11, 2003, pp. 6399-6404 and cover page.
A. Dunkel, et al., "Molecular and sensory characterization of γ-glutamyl peptides as key contributors to the kokumi taste of edible beans (*Phaseolus vulgaris L.*)", J. Argric. Food Chem., Aug. 8, 2007, vol. 55, pp. 6712-6719.
G. Payne, et al., "γ-Glutamyltransferase is not involved in the bulk uptake of amino acids, peptides or γ-glutamyl-amino acids in yeast (*Saccharomyces cerevisiae*)", Biochem. J., Feb. 1, 1984, vol. 218, No. 1, pp. 147-155.
A. Bourbouloux et al., "Hgt1p, a High Affinity Glutathione Transporter from the Yeast *Saccharomyces cerevisiae*", The Journal of Biological Chemistry, vol. 275, No. 18, Apr. 28, 2000, pp. 13259-13265.

(Continued)

*Primary Examiner* — Hamid R Badr

(74) *Attorney, Agent, or Firm* — Oblon, McClelland, Maier & Neustadt, L.L.P.

(57) ABSTRACT

A yeast extract containing a peptide, such as γ-Glu-X and γ-Glu-X-Gly, wherein X can represent an amino acid or an amino acid derivative other than Cys and derivatives thereof, is prepared by culturing a yeast in a medium containing a peptide such as γ-Glu-X, γ-Glu-X-Gly and X-Gly, and preparing a yeast extract from the obtained cells.

18 Claims, 14 Drawing Sheets

(56) References Cited

OTHER PUBLICATIONS

D. Ganguli et al., "The alternative pathway of glutathione degradation is mediated by a novel protein complex involving three new genes in *Saccharomyces cerevisiae*", Genetics, vol. 175, No. 3, Jan. 1, 2006, pp. 1137-1151.

K. Mehdi, et al., "γ-Glutamyl transpeptidase in the yeast *Saccharomyces cerevisiae* and its role in the vacuolar transport and metabolism of glutathione", Biochemical Journal, vol. 359, No. 3, Nov. 1, 2001, pp. 631-637.

K. Rambabu, et al., "Studies on the properties of the variants of gamma-glutamyl transpeptidase in human urine", J. Biosci., vol. 4, No. 3, Sep. 1, 1982, pp. 287-294.

International Preliminary Report on Patentability and Written Opinion issued Oct. 26, 2012 in PCT/JP2011/059480 filed Apr. 12, 2011.

Yoichi Ueda, et al., "Characteristic Flavor Constituents in Water Extract of Garlic", Agric. Biol. Chem., 54(1), 1990, pp. 163-169.

Yoichi Ueda, et al., "Flavor Characteristics of Glutathione in Raw and Cooked Foodstuffs", Biosci. Biotech. Biochem., 61(12), 1997, pp. 1977-1980.

Minghua Wang, et al., "Activation of Family C G-protein-coupled Receptors by the Tripeptide Glutathione", Journal of Biological Chemistry, vol. 281, No. 13, Mar. 31, 2006, pp. 8864-8870.

Ana San Gabriel, et al., "The calcium-sensing receptor in taste tissue", Biochemical and Biophysical Research Communications, 378, 2009, pp. 414-418.

Takeaki Ohsu, et al., "Involvement of the Calcium-sensing Receptor in Human Taste Perception", Journal of Biological Chemistry, vol. 285, No. 2, Jan. 8, 2010, pp. 1016-1022.

Simone Toelstede, et al., "Kokumi-Active Glutamyl Peptides in Cheeses and Their Biogeneration by *Penicillium roqueforti*", Journal of Agricultural and Food Chemistry, 57, 2009, pp. 3738-3748.

Naoyuki Taniguchi, "γ-glutamyl cycle", Protein Nucleic acid Enzyme, Special Issue "Epoch of Glutathione research", vol. 33, No. 9, pp. 1432-1441 plus cover page (with partial English-language translation).

Ronald A. Vitali, et al., "The Isolation of γ-L-Glutamyl Peptides from a Fermentation Broth", The Journal of Biological Chemistry, vol. 240, No. 6, Jun. 1965, pp. 2508-2511.

Kuniki Kino, et al., "Novel substrate specificity of glutathione synthesis enzymes from *Streptococcus agalactiae* and *Colstridium acetobutylicum*", Biochemical and Biophysical Research Communications, 352, 2007, pp. 351-359.

B. Volesky, et al., "Biosorption of heavy metals by *Saccharomyces cerevisiae*", Appl Microbiol Biotechnol, 42, 1995, pp. 797-806.

Jaspreet Kaur, et al., "Differential roles played by the native cysteine residues of the yeast glutathione transporter, Hgt1p", FEMS Yeast Res, 9, 2009, pp. 849-866.

U.S. Appl. No. 13/838,065, filed Mar. 15, 2013, Nishiuchi, et al.
U.S. Appl. No. 13/593,974, filed Aug. 24, 2012, Nishiuchi, et al.

* cited by examiner

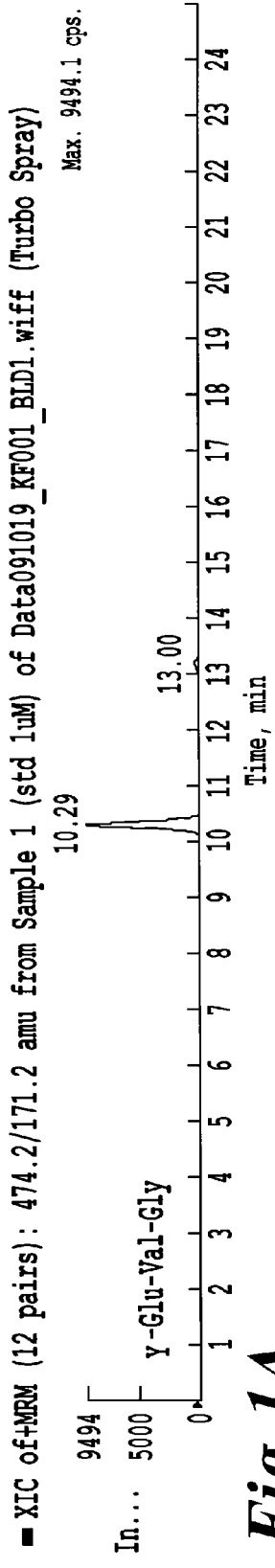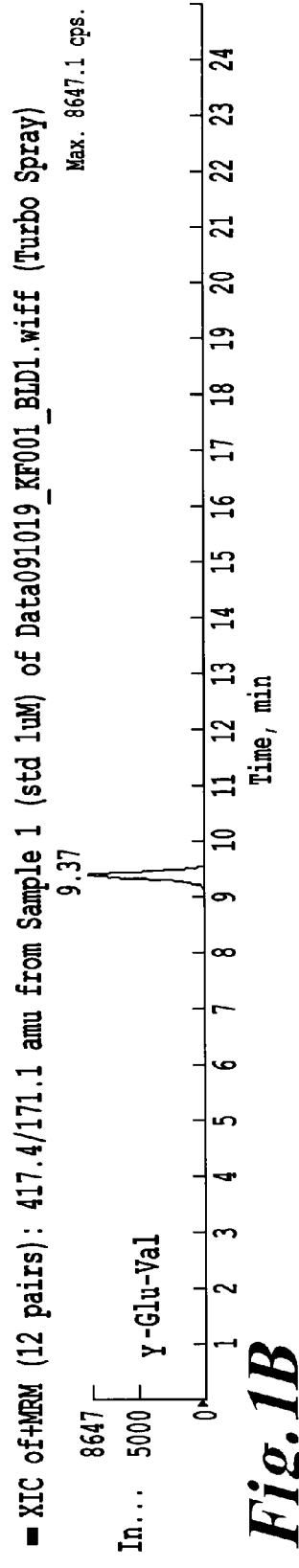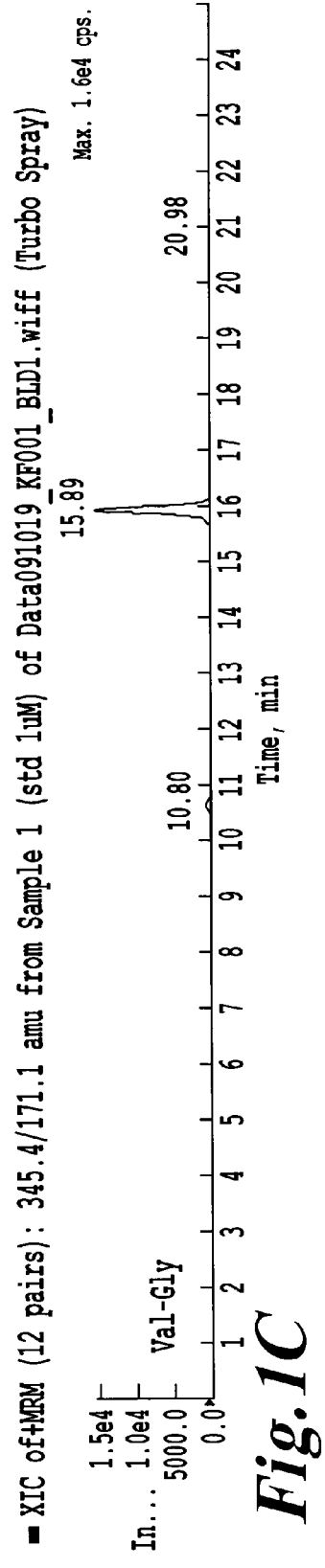

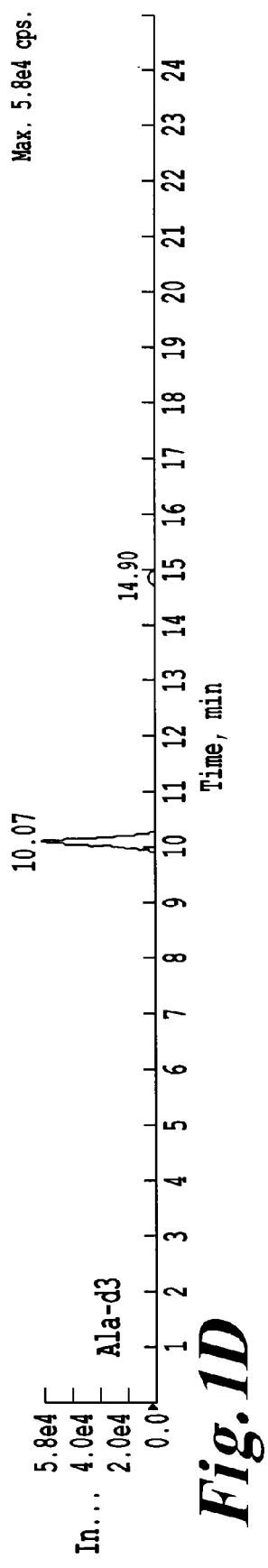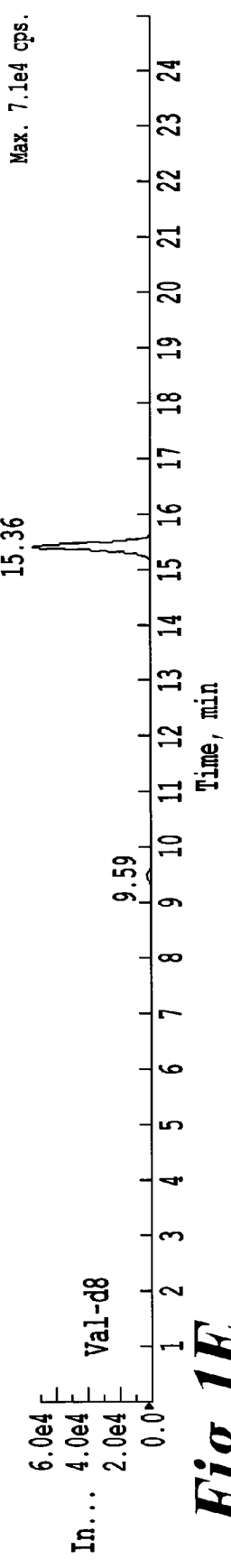

SEQUENCE LISTING

<160> NUMBER OF SEQ ID NOS: 61

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
gataaggaga atccatacaa                                        20

<210> SEQ ID NO 2
<211> LENGTH: 60
<212> TYPE: DNA
<213> ORGANISM: Artificial Sequence
<220> FEATURE:
<223> OTHER INFORMATION: primer

<400> SEQUENCE: 2
gtgagtttag tatacatgca tttacttata atacagtttt gatttatctt cgtttcctgc    60

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
aaaactgtat tataagtaaa                                        20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
cacttatttg cgatacagaa                                        20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gataaggaga atccatacaa                                        20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
cacttatttg cgatacagaa                                        20

<210> SEQ ID NO 7
<211> LENGTH: 29
<212> TYPE: DNA
<213> ORGANISM: Artificial Sequence

```
<220> FEATURE:
<223> OTHER INFORMATION: primer

<400> SEQUENCE: 7
atagcatgct cataaaattg ataaggaga                                29

<210> SEQ ID NO 8
<211> LENGTH: 29
<212> TYPE: DNA
<213> ORGANISM: Artificial Sequence
<220> FEATURE:
<223> OTHER INFORMATION: primer

<400> SEQUENCE: 8
atagaattca ggacgtcatt agtggcgaa                                29

<210> SEQ ID NO 9
<211> LENGTH: 35
<212> TYPE: DNA
<213> ORGANISM: Artificial Sequence
<220> FEATURE:
<223> OTHER INFORMATION: primer

<400> SEQUENCE: 9
atactgcaga taatcgatta atttttttt ctttc                          35

<210> SEQ ID NO 10
<211> LENGTH: 29
<212> TYPE: DNA
<213> ORGANISM: Artificial Sequence
<220> FEATURE:
<223> OTHER INFORMATION: primer

<400> SEQUENCE: 10
atactgcaga agtagataat tacttcctt                                29

<210> SEQ ID NO 11
<211> LENGTH: 26
<212> TYPE: DNA
<213> ORGANISM: Artificial Sequence
<220> FEATURE:
<223> OTHER INFORMATION: primer

<400> SEQUENCE: 11
atagacgtct aattttttt tctttc                                    26

<210> SEQ ID NO 12
<211> LENGTH: 29
<212> TYPE: DNA
<213> ORGANISM: Artificial Sequence
<220> FEATURE:
<223> OTHER INFORMATION: primer

<400> SEQUENCE: 12
atagacgtct gttttatatt tgttgtaaa                                29

<210> SEQ ID NO 13
<211> LENGTH: 100
<212> TYPE: DNA
<213> ORGANISM: Artificial Sequence
<220> FEATURE:
<223> OTHER INFORMATION: primer

<400> SEQUENCE: 13
agaaagtgtc atttccatca gtacgctttt ttggccgggt tagctagtgc tgacaaatag    60
```

```
<210> SEQ ID NO 14
<211> LENGTH: 100
<212> TYPE: DNA
<213> ORGANISM: Artificial Sequence
<220> FEATURE:
<223> OTHER INFORMATION: primer

<400> SEQUENCE: 14
aatccattag tgatagccca ttggttaact tcctggatca attcattcaa ttgatccttg      60
gaaggtggat agtgtgccat tgttttatat ttgttgtaaa                          100

<210> SEQ ID NO 15
<211> LENGTH: 30
<212> TYPE: DNA
<213> ORGANISM: Artificial Sequence
<220> FEATURE:
<223> OTHER INFORMATION: primer

<400> SEQUENCE: 15
agttacagca atgaaagagc agagcgagag                                      30

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16
attactgctg ctgttccagc ccatatccaa                                      30

<210> SEQ ID NO 17
<211> LENGTH: 100
<212> TYPE: DNA
<213> ORGANISM: Artificial Sequence
<220> FEATURE:
<223> OTHER INFORMATION: primer

<400> SEQUENCE: 17
ttttcagcag ttgcttgttg ctgctgcctg ttaatcacat caaacccact gcaagggcag      60
tcgatgggtc tgtaaacgcc tcttaaccca actgcacaga                          100

<210> SEQ ID NO 18
<211> LENGTH: 100
<212> TYPE: DNA
<213> ORGANISM: Artificial Sequence
<220> FEATURE:
<223> OTHER INFORMATION: primer

<400> SEQUENCE: 18
ttgatctgga taggaatggt tgttggcgtt ggcgagggct ccgactccaa cgagtcgctc      60
tccctataaa tggtactcat tgttttatat ttgttgtaaa                          100

<210> SEQ ID NO 19
<211> LENGTH: 2476
<212> TYPE: DNA
<213> ORGANISM: Saccharomyces cerevisiae
<220> FEATURE:
<221> NAME/KEY: CDS
<222> LOCATION: (501)..(1976)

<400> SEQUENCE: 19
```

(prior continued entry, top of page:)

```
ttgaaccttc ttgaattatc tcttaaccca actgcacaga                          100
```

```
aacttctggg actagttcag aacaattcaa tgtatgggat tggataataatt ggacaagtgc    60
```
*(corrections as visible)*

```
aacttctggg actagttcag aacaattcaa tgtatgggat tggataatt  ggacaagtgc     60 tacttgaaca tttgaagttt ccatactttt gatactttg  aagttacttc gtttggtgtt    120
atggtcacca acatctttt  tttctccttc tttcaaactc ttttttaact ccagaaaaga    180
aattctttat ttcacaaaaa tttctcccca cttttaatgt aattttttctt tatataaat    240 atatatatat atacatgagt atcaatacaa tataacctaa tctagctttt tatccaatgg    300
acttgactat catcagtact agaaagtgtc atttccatca gtacgctttt ttggccgggt    360
tagctagtgc tgacaaatag ttgaaccttc ttgaattatc taaatgtctc ccaaatcaac    420
cacatccata tacgatcctc caaaggtagc aaagtgccac ttcaagcaat tataggaaga    480
aagcactact cctataaaat atg gca cac tat cca cct tcc aag gat caa ttg    533
                      Met Ala His Tyr Pro Pro Ser Lys Asp Gln Leu
                       1               5                  10 aat gaa ttg atc cag gaa gtt aac caa tgg gct atc act aat gga tta     581
Asn Glu Leu Ile Gln Glu Val Asn Gln Trp Ala Ile Thr Asn Gly Leu
            15                  20                  25 tcc atg tat cct cct aaa ttc gag gag aac cca tca aat gca tcg gtg     629
Ser Met Tyr Pro Pro Lys Phe Glu Glu Asn Pro Ser Asn Ala Ser Val
        30                  35                  40 tca cca gta act atc tat cca acc cca att cct agg aaa tgt ttt gat     677
Ser Pro Val Thr Ile Tyr Pro Thr Pro Ile Pro Arg Lys Cys Phe Asp
    45                  50                  55 gag gcc gtt caa ata caa ccg gta ttc aat gaa tta tac gcc cgt att     725
Glu Ala Val Gln Ile Gln Pro Val Phe Asn Glu Leu Tyr Ala Arg Ile
60                  65                  70                  75 acc caa gat atg gcc caa cct gat tct tat tta cat aaa aca act gaa     773
Thr Gln Asp Met Ala Gln Pro Asp Ser Tyr Leu His Lys Thr Thr Glu
                80                  85                  90 gcg tta gct cta tca gat tcc gag ttt act gga aaa ctg tgg tct cta     821
Ala Leu Ala Leu Ser Asp Ser Glu Phe Thr Gly Lys Leu Trp Ser Leu
            95                 100                 105 tac ctt gct acc tta aaa tct gca cag tac aaa aag cag aat ttt agg     869
Tyr Leu Ala Thr Leu Lys Ser Ala Gln Tyr Lys Lys Gln Asn Phe Arg
        110                 115                 120 cta ggt ata ttt aga tca gat tat ttg att gat aag aaa aag ggt act     917
Leu Gly Ile Phe Arg Ser Asp Tyr Leu Ile Asp Lys Lys Lys Gly Thr
    125                 130                 135 gaa cag att aag caa gtc gag ttt aat aca gtg tca gtg tca ttt gca     965
Glu Gln Ile Lys Gln Val Glu Phe Asn Thr Val Ser Val Ser Phe Ala
140                 145                 150                 155 ggc ctt agc gag aaa gtt gat aga ttg cac tct tat tta aat agg gca    1013
Gly Leu Ser Glu Lys Val Asp Arg Leu His Ser Tyr Leu Asn Arg Ala
                160                 165                 170 aac aag tac gat cct aaa gga cca att tat aat gat caa aat atg gtc    1061
Asn Lys Tyr Asp Pro Lys Gly Pro Ile Tyr Asn Asp Gln Asn Met Val
            175                 180                 185 att tct gat tca gga tac ctt ttg tct aag gca ttg gcc aaa gct gtg    1109
Ile Ser Asp Ser Gly Tyr Leu Leu Ser Lys Ala Leu Ala Lys Ala Val
        190                 195                 200 gaa tcg tat aag tca caa caa agt tct tct aca act agt gat cct att    1157
Glu Ser Tyr Lys Ser Gln Gln Ser Ser Ser Thr Thr Ser Asp Pro Ile
    205                 210                 215 gtc gca ttc att gtg caa aga aac gag aga aat gtg ttt gat caa aag    1205
Val Ala Phe Ile Val Gln Arg Asn Glu Arg Asn Val Phe Asp Gln Lys
220                 225                 230                 235 gtc ttg gaa ttg aat ctg ttg gaa aaa ttc ggt acc aaa tct gtt agg    1253
Val Leu Glu Leu Asn Leu Leu Glu Lys Phe Gly Thr Lys Ser Val Arg
                240                 245                 250
```

| | |
|---|---|
| ttg acg ttt gat gat gtt aac gat aaa ttg ttc att gat gat aaa acg<br>Leu Thr Phe Asp Asp Val Asn Asp Lys Leu Phe Ile Asp Asp Lys Thr<br>255 260 265 | 1301 |
| gga aag ctt ttc att agg gac aca gag cag gaa ata gcg gtg gtt tat<br>Gly Lys Leu Phe Ile Arg Asp Thr Glu Gln Glu Ile Ala Val Val Tyr<br>270 275 280 | 1349 |
| tac aga acg ggt tac aca acc act gat tac acg tcc gaa aag gac tgg<br>Tyr Arg Thr Gly Tyr Thr Thr Thr Asp Tyr Thr Ser Glu Lys Asp Trp<br>285 290 295 | 1397 |
| gag gca aga cta ttc ctc gaa aaa agt ttc gca ata aag gcc cca gat<br>Glu Ala Arg Leu Phe Leu Glu Lys Ser Phe Ala Ile Lys Ala Pro Asp<br>300 305 310 315 | 1445 |
| tta ctc act caa tta tct ggc tcc aag aaa att cag caa ttg ttg aca<br>Leu Leu Thr Gln Leu Ser Gly Ser Lys Lys Ile Gln Gln Leu Leu Thr<br>320 325 330 | 1493 |
| gat gag ggc gta tta ggt aaa tac atc tcc gat gct gag aaa aag agt<br>Asp Glu Gly Val Leu Gly Lys Tyr Ile Ser Asp Ala Glu Lys Lys Ser<br>335 340 345 | 1541 |
| agt ttg tta aaa act ttt gtc aaa ata tat ccc ttg gat gat acg aag<br>Ser Leu Leu Lys Thr Phe Val Lys Ile Tyr Pro Leu Asp Asp Thr Lys<br>350 355 360 | 1589 |
| ctt ggc agg gaa ggc aag agg ctg gca tta agt gag ccc tct aaa tac<br>Leu Gly Arg Glu Gly Lys Arg Leu Ala Leu Ser Glu Pro Ser Lys Tyr<br>365 370 375 | 1637 |
| gtg tta aaa cca cag cgg gaa ggt ggc gga aac aat gtt tat aaa gaa<br>Val Leu Lys Pro Gln Arg Glu Gly Gly Gly Asn Asn Val Tyr Lys Glu<br>380 385 390 395 | 1685 |
| aat att cct aat ttt ttg aaa ggt atc gaa gaa cgt cac tgg gat gca<br>Asn Ile Pro Asn Phe Leu Lys Gly Ile Glu Glu Arg His Trp Asp Ala<br>400 405 410 | 1733 |
| tat att ctc atg gag ttg att gaa cca gag ttg aat gaa aat aat att<br>Tyr Ile Leu Met Glu Leu Ile Glu Pro Glu Leu Asn Glu Asn Asn Ile<br>415 420 425 | 1781 |
| ata tta cgt gat aac aaa tct tac aac gaa cca atc atc agt gaa cta<br>Ile Leu Arg Asp Asn Lys Ser Tyr Asn Glu Pro Ile Ile Ser Glu Leu<br>430 435 440 | 1829 |
| gga att tat ggt tgc gtt cta ttt aac gac gag caa gtt tta tcg aac<br>Gly Ile Tyr Gly Cys Val Leu Phe Asn Asp Glu Gln Val Leu Ser Asn<br>445 450 455 | 1877 |
| gaa ttt agt ggc tca tta cta aga tcc aaa ttt aat act tca aat gaa<br>Glu Phe Ser Gly Ser Leu Leu Arg Ser Lys Phe Asn Thr Ser Asn Glu<br>460 465 470 475 | 1925 |
| ggt gga gtg gcg gca gga ttc gga tgt ttg gac agt att att ctt tac<br>Gly Gly Val Ala Ala Gly Phe Gly Cys Leu Asp Ser Ile Ile Leu Tyr<br>480 485 490 | 1973 |
| tag gtgtacatgt actatacaca tagatgctag gaagatgatg ctagaacttg | 2026 |
| attaacaatt agttaaggaa tatataatca cacttctaca taaatttgct gttttaggct | 2086 |
| cattccttct ttctttcacc ctttagtagc gaagtacacc atttagctgc accaacagtg | 2146 |
| ttgctagata tggtgactat tgtgaagaag ggtattaact ctagtagacc ggcagacata | 2206 |
| ccgaaacata tgaaacttgc gtaatgctcg tactgaaaat cttttggcctg tttcttactg | 2266 |
| aatcccttta gtaaaagta cctctgcaaa taggtaaagg ttcttttttgg ggccattagt | 2326 |
| tgatttgcca agattggtcc tacaatagga attagcgaca gtaatgttag tgaagtaaaa | 2386 |
| ttggagactt taaaaaacat tctgaatagt aatctgggaa tcttaaaaat ccgacttccc | 2446 |
| tttattgtgt tgaaatttct caccgcatca | 2476 |

<210> SEQ ID NO 20
<211> LENGTH: 491
<212> TYPE: PRT
<213> ORGANISM: Saccharomyces cerevisiae

<400> SEQUENCE: 20

Met Ala His Tyr Pro Pro Ser Lys Asp Gln Leu Asn Glu Leu Ile Gln
1               5                   10                  15

Glu Val Asn Gln Trp Ala Ile Thr Asn Gly Leu Ser Met Tyr Pro Pro
            20                  25                  30

Lys Phe Glu Glu Asn Pro Ser Asn Ala Ser Val Ser Pro Val Thr Ile
        35                  40                  45

Tyr Pro Thr Pro Ile Pro Arg Lys Cys Phe Asp Glu Ala Val Gln Ile
    50                  55                  60

Gln Pro Val Phe Asn Glu Leu Tyr Ala Arg Ile Thr Gln Asp Met Ala
65                  70                  75                  80

Gln Pro Asp Ser Tyr Leu His Lys Thr Thr Glu Ala Leu Ala Leu Ser
                85                  90                  95

Asp Ser Glu Phe Thr Gly Lys Leu Trp Ser Leu Tyr Leu Ala Thr Leu
            100                 105                 110

Lys Ser Ala Gln Tyr Lys Lys Gln Asn Phe Arg Leu Gly Ile Phe Arg
        115                 120                 125

Ser Asp Tyr Leu Ile Asp Lys Lys Gly Thr Glu Gln Ile Lys Gln
    130                 135                 140

Val Glu Phe Asn Thr Val Ser Val Ser Phe Ala Gly Leu Ser Glu Lys
145                 150                 155                 160

Val Asp Arg Leu His Ser Tyr Leu Asn Arg Ala Asn Lys Tyr Asp Pro
                165                 170                 175

Lys Gly Pro Ile Tyr Asn Asp Gln Asn Met Val Ile Ser Asp Ser Gly
            180                 185                 190

Tyr Leu Leu Ser Lys Ala Leu Ala Lys Ala Val Glu Ser Tyr Lys Ser
        195                 200                 205

Gln Gln Ser Ser Thr Thr Ser Asp Pro Ile Val Ala Phe Ile Val
    210                 215                 220

Gln Arg Asn Glu Arg Asn Val Phe Asp Gln Lys Val Leu Glu Leu Asn
225                 230                 235                 240

Leu Leu Glu Lys Phe Gly Thr Lys Ser Val Arg Leu Thr Phe Asp Asp
                245                 250                 255

Val Asn Asp Lys Leu Phe Ile Asp Asp Lys Thr Gly Lys Leu Phe Ile
            260                 265                 270

Arg Asp Thr Glu Gln Glu Ile Ala Val Val Tyr Tyr Arg Thr Gly Tyr
        275                 280                 285

Thr Thr Thr Asp Tyr Thr Ser Glu Lys Asp Trp Glu Ala Arg Leu Phe
    290                 295                 300

Leu Glu Lys Ser Phe Ala Ile Lys Ala Pro Asp Leu Leu Thr Gln Leu
305                 310                 315                 320

Ser Gly Ser Lys Lys Ile Gln Gln Leu Leu Thr Asp Glu Gly Val Leu
                325                 330                 335

Gly Lys Tyr Ile Ser Asp Ala Lys Lys Ser Ser Leu Leu Lys Thr
            340                 345                 350

Phe Val Lys Ile Tyr Pro Leu Asp Asp Thr Lys Leu Gly Arg Glu Gly
        355                 360                 365

Lys Arg Leu Ala Leu Ser Glu Pro Ser Lys Tyr Val Leu Lys Pro Gln
    370                 375                 380

```
Arg Glu Gly Gly Gly Asn Asn Val Tyr Lys Glu Asn Ile Pro Asn Phe
385                 390                 395                 400

Leu Lys Gly Ile Glu Glu Arg His Trp Asp Ala Tyr Ile Leu Met Glu
            405                 410                 415

Leu Ile Glu Pro Glu Leu Asn Glu Asn Asn Ile Ile Leu Arg Asp Asn
                420                 425                 430

Lys Ser Tyr Asn Glu Pro Ile Ile Ser Glu Leu Gly Ile Tyr Gly Cys
            435                 440                 445

Val Leu Phe Asn Asp Glu Gln Val Leu Ser Asn Glu Phe Ser Gly Ser
        450                 455                 460

Leu Leu Arg Ser Lys Phe Asn Thr Ser Asn Glu Gly Gly Val Ala Ala
465                 470                 475                 480

Gly Phe Gly Cys Leu Asp Ser Ile Ile Leu Tyr
            485                 490

<210> SEQ ID NO 21
<211> LENGTH: 3400
<212> TYPE: DNA
<213> ORGANISM: Saccharomyces cerevisiae
<220> FEATURE:
<221> NAME/KEY: CDS
<222> LOCATION: (501)..(2900)

<400> SEQUENCE: 21
```

| | | |
|---|---|---|
| gacgttgcat caaaggccaa gacatggcat tagtcaccct tgttgcaacg atagacgcat | 60 |
| actacggacc cctcaaacct ccctacctgc ccgtcgctat cgcattaatt ttcttttttt | 120 |
| ccactatttt tccggcccgc cacacctccg actacaagac gccacatcta cgttttgtca | 180 |
| cacaaaatcc aggacaatag ccgtctgcaa ggcaccaagg ttttcagcag ttgcttgttg | 240 |
| ctgctgcctg ttaatcacat caaacccact gcaagggcag tcgatgggtc tgtaaacgcc | 300 |
| ttagcaatcg ttgttgaaga agagagctc ttatcatcat ggggtgccca tcattttct | 360 |
| ttttttttca aattttgggc tattcaatga attgtttcga ctatatatgg acaatcatcg | 420 |
| gaagctgtgt attcttggta aaagttttc gactgtgtgg cagaaaataa ccgcaacaat | 480 |

```
tatataacgt cacagaacac atg agt acc att tat agg gag agc gac tcg ttg    533
                       Met Ser Thr Ile Tyr Arg Glu Ser Asp Ser Leu
                         1               5                  10 gag tcg gag ccc tcg cca acg cca aca acc att cct atc cag atc aat    581
Glu Ser Glu Pro Ser Pro Thr Pro Thr Thr Ile Pro Ile Gln Ile Asn
             15                  20                  25 atg gaa gag gaa aag aaa gat gct ttc gtt aag aat att gac gag gac    629
Met Glu Glu Glu Lys Lys Asp Ala Phe Val Lys Asn Ile Asp Glu Asp
         30                  35                  40 gtc aat aat ctc act gcg act act gat gag gag gac cgc gat ccg gaa    677
Val Asn Asn Leu Thr Ala Thr Thr Asp Glu Glu Asp Arg Asp Pro Glu
 45                  50                  55 agc caa aaa ttc gac agg cat tcc ata cag gag gaa ggt ctc gtt tgg    725
Ser Gln Lys Phe Asp Arg His Ser Ile Gln Glu Glu Gly Leu Val Trp
 60                  65                  70                  75 aag ggc gac cct aca tac ttg ccc aat tct cca tat cct gaa gtg aga    773
Lys Gly Asp Pro Thr Tyr Leu Pro Asn Ser Pro Tyr Pro Glu Val Arg
                 80                  85                  90 tcg gcg gtg tcc atc gag gat gac ccc acc atc cgc ctc aac cac tgg    821
Ser Ala Val Ser Ile Glu Asp Asp Pro Thr Ile Arg Leu Asn His Trp
             95                 100                 105 aga acg tgg ttc ttg acc acg gtg ttt gtg gta gtt ttc gcc ggt gtt    869
Arg Thr Trp Phe Leu Thr Thr Val Phe Val Val Val Phe Ala Gly Val
```

-continued

```
            110                 115                 120
aat caa ttt ttt tcc ctg aga tat cca tcg cta gag atc aac ttc ctt       917
Asn Gln Phe Phe Ser Leu Arg Tyr Pro Ser Leu Glu Ile Asn Phe Leu
    125                 130                 135 gtt gca caa gtt gtt tgc tac cca att ggt agg ata ctg gct ctc ttg       965
Val Ala Gln Val Val Cys Tyr Pro Ile Gly Arg Ile Leu Ala Leu Leu
140                 145                 150                 155 ccc gac tgg aag tgt tct aaa gtg cca ttt ttc gat tta aac ccg ggc      1013
Pro Asp Trp Lys Cys Ser Lys Val Pro Phe Phe Asp Leu Asn Pro Gly
                160                 165                 170 cca ttt acc aaa aag gaa cac gcc gtg gtc aca att gcc gtg gcg ctt      1061
Pro Phe Thr Lys Lys Glu His Ala Val Val Thr Ile Ala Val Ala Leu
        175                 180                 185 act tcc tct act gca tac gct atg tac att ttg aac gcc cag gga agc      1109
Thr Ser Ser Thr Ala Tyr Ala Met Tyr Ile Leu Asn Ala Gln Gly Ser
            190                 195                 200 ttt tac aac atg aaa ctt aat gtc gga tat cag ttc ttg ttg gtt tgg      1157
Phe Tyr Asn Met Lys Leu Asn Val Gly Tyr Gln Phe Leu Leu Val Trp
    205                 210                 215 aca tct caa atg att ggt tat ggt gct gca ggt ctt acc aga aga tgg      1205
Thr Ser Gln Met Ile Gly Tyr Gly Ala Ala Gly Leu Thr Arg Arg Trp
220                 225                 230                 235 gtc gtc aac cct gca agc tct atc tgg cct cag act tta att tca gtg      1253
Val Val Asn Pro Ala Ser Ser Ile Trp Pro Gln Thr Leu Ile Ser Val
                240                 245                 250 tcc ttg ttt gat tcg ttg cac tcg aga aaa gtt gaa aag aca gtc gca      1301
Ser Leu Phe Asp Ser Leu His Ser Arg Lys Val Glu Lys Thr Val Ala
        255                 260                 265 aat ggt tgg acg atg ccc cgt tac agg ttc ttc tta atc gtc ctt atc      1349
Asn Gly Trp Thr Met Pro Arg Tyr Arg Phe Phe Leu Ile Val Leu Ile
            270                 275                 280 gga tcg ttc atc tgg tat tgg gta cct gga ttc ctc ttt acc ggt ctg      1397
Gly Ser Phe Ile Trp Tyr Trp Val Pro Gly Phe Leu Phe Thr Gly Leu
    285                 290                 295 tcc tat ttc aac gtt atc cta tgg ggg tcg aag aca aga cac aat ttc      1445
Ser Tyr Phe Asn Val Ile Leu Trp Gly Ser Lys Thr Arg His Asn Phe
300                 305                 310                 315 atc gct aac aca atc ttt ggt act caa agt ggt ctc ggt gcg ttg cca      1493
Ile Ala Asn Thr Ile Phe Gly Thr Gln Ser Gly Leu Gly Ala Leu Pro
                320                 325                 330 att aca ttt gac tac acc cag gtt tcc caa gcc atg tcc ggc tct gtt      1541
Ile Thr Phe Asp Tyr Thr Gln Val Ser Gln Ala Met Ser Gly Ser Val
        335                 340                 345 ttc gcc aca cca ttc tac gtc tcc gcc aac acc tat gca tca gtg ttg      1589
Phe Ala Thr Pro Phe Tyr Val Ser Ala Asn Thr Tyr Ala Ser Val Leu
            350                 355                 360 ata ttc ttc gtc ata gtg ctg cca tgt ctt tat ttt acg aat acc tgg      1637
Ile Phe Phe Val Ile Val Leu Pro Cys Leu Tyr Phe Thr Asn Thr Trp
    365                 370                 375 tat gcc aaa tac atg ccc gtc att tca ggt tct act tat gac aac act      1685
Tyr Ala Lys Tyr Met Pro Val Ile Ser Gly Ser Thr Tyr Asp Asn Thr
380                 385                 390                 395 caa aac aaa tac aac gta aca aag att ctt aac gag gat tat tcc att      1733
Gln Asn Lys Tyr Asn Val Thr Lys Ile Leu Asn Glu Asp Tyr Ser Ile
                400                 405                 410 aat ctt gag aaa tat aag gaa tac tca ccg gta ttc gtt cca ttt tcc      1781
Asn Leu Glu Lys Tyr Lys Glu Tyr Ser Pro Val Phe Val Pro Phe Ser
        415                 420                 425 tat ctt ttg tcg tat gct tta aat ttt gcc gct gtt atc gcc gtt ttt      1829
```

-continued

```
Tyr Leu Leu Ser Tyr Ala Leu Asn Phe Ala Ala Val Ile Ala Val Phe
        430                 435                 440 gtc cac tgc atc tta tac cac ggt aaa gat att gtc gcc aag ttt aaa      1877
Val His Cys Ile Leu Tyr His Gly Lys Asp Ile Val Ala Lys Phe Lys
    445                 450                 455 gac cgt aaa aat ggt ggc act gac att cac atg aga atc tac tcc aag      1925
Asp Arg Lys Asn Gly Gly Thr Asp Ile His Met Arg Ile Tyr Ser Lys
460                 465                 470                 475 aac tat aag gat tgt ccc gat tgg tgg tat tta ctt ttg cag att gtc      1973
Asn Tyr Lys Asp Cys Pro Asp Trp Trp Tyr Leu Leu Leu Gln Ile Val
                480                 485                 490 atg atc ggt tta gga ttt gta gca gtg tgc tgt ttc gat act aag ttc      2021
Met Ile Gly Leu Gly Phe Val Ala Val Cys Cys Phe Asp Thr Lys Phe
                495                 500                 505 cca gct tgg gca ttt gtt att gca ata tta att tcc ctt gta aat ttc      2069
Pro Ala Trp Ala Phe Val Ile Ala Ile Leu Ile Ser Leu Val Asn Phe
            510                 515                 520 atc ccg caa ggt atc ttg gaa gca atg act aac caa cac gta ggt ttg      2117
Ile Pro Gln Gly Ile Leu Glu Ala Met Thr Asn Gln His Val Gly Leu
        525                 530                 535 aat att atc aca gaa ttg atc tgc ggt tat atg ctg cct tta aga cca      2165
Asn Ile Ile Thr Glu Leu Ile Cys Gly Tyr Met Leu Pro Leu Arg Pro
540                 545                 550                 555 atg gca aac tta tta ttc aag cta tac gga ttt att gtc atg aga caa      2213
Met Ala Asn Leu Leu Phe Lys Leu Tyr Gly Phe Ile Val Met Arg Gln
                560                 565                 570 ggc ttg aat ttg agt aga gat ttg aaa tta gcc atg tac atg aag gtt      2261
Gly Leu Asn Leu Ser Arg Asp Leu Lys Leu Ala Met Tyr Met Lys Val
                575                 580                 585 tcc cct cgt ttg atc ttt gcc gtt caa atc tat gcc act atc ata tca      2309
Ser Pro Arg Leu Ile Phe Ala Val Gln Ile Tyr Ala Thr Ile Ile Ser
            590                 595                 600 ggc atg gtt aac gtt ggt gtc cag gaa tgg atg atg cat aat atc gat      2357
Gly Met Val Asn Val Gly Val Gln Glu Trp Met Met His Asn Ile Asp
        605                 610                 615 ggc tta tgt acc acc gat caa cca aat ggc ttc act tgt gct aat ggt      2405
Gly Leu Cys Thr Thr Asp Gln Pro Asn Gly Phe Thr Cys Ala Asn Gly
620                 625                 630                 635 cgc acg gtt ttc aat gct tcc att atc tgg tct ttg cca aag tat ctt      2453
Arg Thr Val Phe Asn Ala Ser Ile Ile Trp Ser Leu Pro Lys Tyr Leu
                640                 645                 650 ttc tca tca ggg cgc att tat aat ccg ctg atg tgg ttc ttg att          2501
Phe Ser Ser Gly Arg Ile Tyr Asn Pro Leu Met Trp Phe Phe Leu Ile
                655                 660                 665 ggt ttg cta ttc cca cta gcc gtt tat gct gtt caa tgg aaa ttc cct      2549
Gly Leu Leu Phe Pro Leu Ala Val Tyr Ala Val Gln Trp Lys Phe Pro
            670                 675                 680 aaa ttt aaa ttt gct aag cac att cat act cct gta ttt ttc aca ggc      2597
Lys Phe Lys Phe Ala Lys His Ile His Thr Pro Val Phe Phe Thr Gly
685                 690                 695 cca ggt aat att cca cca agc aca cct tat aac tac tca tta ttt ttt      2645
Pro Gly Asn Ile Pro Pro Ser Thr Pro Tyr Asn Tyr Ser Leu Phe Phe
700                 705                 710                 715 gca atg tca ttc tgc cta aac ttg ata aga aaa aga tgg aga gct tgg      2693
Ala Met Ser Phe Cys Leu Asn Leu Ile Arg Lys Arg Trp Arg Ala Trp
                720                 725                 730 ttc aat aag tac aat ttc gtc atg ggg gcc ggt gtt gaa gca ggt gtg      2741
Phe Asn Lys Tyr Asn Phe Val Met Gly Ala Gly Val Glu Ala Gly Val
                735                 740                 745
```

-continued

| | | |
|---|---|---|
| gca atc tcc gtc gtc atc atc ttc ttg tgt gta cag tac cca ggt ggt<br>Ala Ile Ser Val Val Ile Ile Phe Leu Cys Val Gln Tyr Pro Gly Gly<br>750 755 760 | 2789 |
| aag ctc agc tgg tgg gga aac aac gtt tgg aaa aga acg tat gat aat<br>Lys Leu Ser Trp Trp Gly Asn Asn Val Trp Lys Arg Thr Tyr Asp Asn<br>765 770 775 | 2837 |
| gat tat aaa aaa ttt tat acc tta aag aaa ggt gag aca ttt ggt tat<br>Asp Tyr Lys Lys Phe Tyr Thr Leu Lys Lys Gly Glu Thr Phe Gly Tyr<br>780 785 790 795 | 2885 |
| gat aaa tgg tgg taa tcatgaaaac ataataataa acctgcagag gttcatatca<br>Asp Lys Trp Trp | 2940 |
| agttttaatt caaaatttgg cacacgtaat agcaaacttt agttcatatt ctgtaatatt | 3000 |
| aagaaattat tttcttttct gtcatccttt catattgctt aacttgaaat actttatctc | 3060 |
| aacgtttaat tatactgtta ataatgtat ttctatattt tagagcacat tttggtcgaa | 3120 |
| acattcaaag cgaccctgc aatatttagc ggaggcatct catccgcctt attttgtaa | 3180 |
| attaacgatc tttagcgcat gccaagtgtt cgataacaaa ttccgacttt aagaaaaaac | 3240 |
| gggcacgagc atacaataaa aaaacttta aaatttatac ctccttgagg tgttctattt | 3300 |
| tatgatagat ccgtatttca gataccaaat gttatataca cttttttaag cttggatttt | 3360 |
| tttctgaata cacggacctt acaaatgcta taaaaaaaaa | 3400 |

<210> SEQ ID NO 22
<211> LENGTH: 799
<212> TYPE: PRT
<213> ORGANISM: Saccharomyces cerevisiae

<400> SEQUENCE: 22

Met Ser Thr Ile Tyr Arg Glu Ser Asp Ser Leu Glu Ser Glu Pro Ser
1               5                   10                  15

Pro Thr Pro Thr Thr Ile Pro Ile Gln Ile Asn Met Glu Glu Glu Lys
            20                  25                  30

Lys Asp Ala Phe Val Lys Asn Ile Asp Glu Asp Val Asn Asn Leu Thr
        35                  40                  45

Ala Thr Thr Asp Glu Glu Asp Arg Asp Pro Glu Ser Gln Lys Phe Asp
    50                  55                  60

Arg His Ser Ile Gln Glu Glu Gly Leu Val Trp Lys Gly Asp Pro Thr
65                  70                  75                  80

Tyr Leu Pro Asn Ser Pro Tyr Pro Glu Val Arg Ser Ala Val Ser Ile
                85                  90                  95

Glu Asp Asp Pro Thr Ile Arg Leu Asn His Trp Arg Thr Trp Phe Leu
            100                 105                 110

Thr Thr Val Phe Val Val Phe Ala Gly Val Asn Gln Phe Phe Ser
        115                 120                 125

Leu Arg Tyr Pro Ser Leu Glu Ile Asn Phe Leu Val Ala Gln Val Val
    130                 135                 140

Cys Tyr Pro Ile Gly Arg Ile Leu Ala Leu Pro Asp Trp Lys Cys
145                 150                 155                 160

Ser Lys Val Pro Phe Phe Asp Leu Asn Pro Gly Pro Phe Thr Lys Lys
                165                 170                 175

Glu His Ala Val Val Thr Ile Ala Val Ala Leu Thr Ser Ser Thr Ala
            180                 185                 190

Tyr Ala Met Tyr Ile Leu Asn Ala Gln Gly Ser Phe Tyr Asn Met Lys
        195                 200                 205

Leu Asn Val Gly Tyr Gln Phe Leu Leu Val Trp Thr Ser Gln Met Ile

```
                    210                 215                 220
Gly Tyr Gly Ala Ala Gly Leu Thr Arg Arg Trp Val Val Asn Pro Ala
225                 230                 235                 240

Ser Ser Ile Trp Pro Gln Thr Leu Ile Ser Val Ser Leu Phe Asp Ser
            245                 250                 255

Leu His Ser Arg Lys Val Glu Lys Thr Val Ala Asn Gly Trp Thr Met
                260                 265                 270

Pro Arg Tyr Arg Phe Phe Leu Ile Val Leu Ile Gly Ser Phe Ile Trp
            275                 280                 285

Tyr Trp Val Pro Gly Phe Leu Phe Thr Gly Leu Ser Tyr Phe Asn Val
        290                 295                 300

Ile Leu Trp Gly Ser Lys Thr Arg His Asn Phe Ile Ala Asn Thr Ile
305                 310                 315                 320

Phe Gly Thr Gln Ser Gly Leu Gly Ala Leu Pro Ile Thr Phe Asp Tyr
            325                 330                 335

Thr Gln Val Ser Gln Ala Met Ser Gly Ser Val Phe Ala Thr Pro Phe
                340                 345                 350

Tyr Val Ser Ala Asn Thr Tyr Ala Ser Val Leu Ile Phe Phe Val Ile
            355                 360                 365

Val Leu Pro Cys Leu Tyr Phe Thr Asn Thr Trp Tyr Ala Lys Tyr Met
370                 375                 380

Pro Val Ile Ser Gly Ser Thr Tyr Asp Asn Thr Gln Asn Lys Tyr Asn
385                 390                 395                 400

Val Thr Lys Ile Leu Asn Glu Asp Tyr Ser Ile Asn Leu Glu Lys Tyr
            405                 410                 415

Lys Glu Tyr Ser Pro Val Phe Val Pro Phe Ser Tyr Leu Leu Ser Tyr
                420                 425                 430

Ala Leu Asn Phe Ala Ala Val Ile Ala Val Phe Val His Cys Ile Leu
            435                 440                 445

Tyr His Gly Lys Asp Ile Val Ala Lys Phe Lys Asp Arg Lys Asn Gly
        450                 455                 460

Gly Thr Asp Ile His Met Arg Ile Tyr Ser Lys Asn Tyr Lys Asp Cys
465                 470                 475                 480

Pro Asp Trp Trp Tyr Leu Leu Leu Gln Ile Val Met Ile Gly Leu Gly
            485                 490                 495

Phe Val Ala Val Cys Cys Phe Asp Thr Lys Phe Pro Ala Trp Ala Phe
                500                 505                 510

Val Ile Ala Ile Leu Ile Ser Leu Val Asn Phe Ile Pro Gln Gly Ile
            515                 520                 525

Leu Glu Ala Met Thr Asn Gln His Val Gly Leu Asn Ile Ile Thr Glu
        530                 535                 540

Leu Ile Cys Gly Tyr Met Leu Pro Leu Arg Pro Met Ala Asn Leu Leu
545                 550                 555                 560

Phe Lys Leu Tyr Gly Phe Ile Val Met Arg Gln Gly Leu Asn Leu Ser
            565                 570                 575

Arg Asp Leu Lys Leu Ala Met Tyr Met Lys Val Ser Pro Arg Leu Ile
                580                 585                 590

Phe Ala Val Gln Ile Tyr Ala Thr Ile Ile Ser Gly Met Val Asn Val
            595                 600                 605

Gly Val Gln Glu Trp Met Met His Asn Ile Asp Gly Leu Cys Thr Thr
        610                 615                 620

Asp Gln Pro Asn Gly Phe Thr Cys Ala Asn Gly Arg Thr Val Phe Asn
625                 630                 635                 640
```

Ala Ser Ile Ile Trp Ser Leu Pro Lys Tyr Leu Phe Ser Ser Gly Arg
                645                 650                 655

Ile Tyr Asn Pro Leu Met Trp Phe Phe Leu Ile Gly Leu Leu Phe Pro
            660                 665                 670

Leu Ala Val Tyr Ala Val Gln Trp Lys Phe Pro Lys Phe Lys Phe Ala
        675                 680                 685

Lys His Ile His Thr Pro Val Phe Phe Thr Gly Pro Gly Asn Ile Pro
    690                 695                 700

Pro Ser Thr Pro Tyr Asn Tyr Ser Leu Phe Phe Ala Met Ser Phe Cys
705                 710                 715                 720

Leu Asn Leu Ile Arg Lys Arg Trp Arg Ala Trp Phe Asn Lys Tyr Asn
                725                 730                 735

Phe Val Met Gly Ala Gly Val Glu Ala Gly Val Ala Ile Ser Val Val
            740                 745                 750

Ile Ile Phe Leu Cys Val Gln Tyr Pro Gly Gly Lys Leu Ser Trp Trp
        755                 760                 765

Gly Asn Asn Val Trp Lys Arg Thr Tyr Asp Asn Asp Tyr Lys Lys Phe
    770                 775                 780

Tyr Thr Leu Lys Lys Gly Glu Thr Phe Gly Tyr Asp Lys Trp Trp
785                 790                 795

<210> SEQ ID NO 23
<211> LENGTH: 4393
<212> TYPE: DNA
<213> ORGANISM: Artificial Sequence
<220> FEATURE:
<223> OTHER INFORMATION: plasmid pUC19AOX-G418-BRI

<400> SEQUENCE: 23
gacgaaaggg cctcgtgata cgcctatttt tataggttaa tgtcatgata ataatggttt     60
cttagacgtc aggtggcact tttcggggaa atgtgcgcgg aaccccctatt tgtttatttt    120 tctaaataca ttcaaatatg tatccgctca tgagacaata accctgataa atgcttcaat    180
aatattgaaa aaggaagagt atgagtattc aacatttccg tgtcgccctt attccctttt    240
ttgcggcatt ttgccttcct gtttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140

-continued

```
tcctttttga taatctcatg accaaaatcc cttaacgtga gttttcgttc cactgagcgt    1200
cagaccccgt agaaaagatc aaaggatctt cttgagatcc ttttttttctg cgcgtaatct   1260 gctgcttgca aacaaaaaaa ccaccgctac cagcggtggt ttgtttgccg gatcaagagc    1320
taccaactct tttccgaag gtaactggct tcagcagagc gcagatacca aatactgtcc     1380
ttctagtgta gccgtagtta ggccaccact tcaagaactc tgtagcaccg cctacatacc    1440
tcgctctgct aatcctgtta ccagtggctg ctgccagtgg cgataagtcg tgtcttaccg    1500
ggttggactc aagacgatag ttaccggata aggcgcagcg gtcgggctga acggggggtt    1560
cgtgcacaca gcccagcttg gagcgaacga cctacaccga actgagatac ctacagcgtg    1620
agctatgaga aagcgccacg cttcccgaag ggagaaaggc ggacaggtat ccggtaagcg    1680
gcagggtcgg aacaggagag cgcacgaggg agcttccagg gggaaacgcc tggtatcttt    1740
atagtcctgt cgggtttcgc cacctctgac ttgagcgtcg atttttgtga tgctcgtcag    1800
gggggcggag cctatggaaa aacgccagca acgcggcctt tttacggttc ctggccttt     1860 gctggccttt tgctcacatg ttctttcctg cgttatcccc tgattctgtg ataaccgta     1920 ttaccgccct tgagtgagct gataccgctc gccgcagccg aacgaccgag cgcagcgagt    1980
cagtgagcga ggaagcggaa gagcgcccaa tacgcaaacc gcctctcccc gcgcgttggc    2040
cgattcatta atgcagctgg cacgacaggt ttcccgactg gaaagcgggc agtgagcgca    2100
acgcaattaa tgtgagttag ctcactcatt aggcaccccca ggctttacac tttatgcttc    2160
cggctcgtat gttgtgtgga attgtgagcg gataacaatt tcacacagga aacagctatg    2220
accatgatta cgccaagctt gcatgcctgc aggtcgactc tagaggatcc ccatccttt     2280 gttgtttccg ggtgtacaat atggacttcc tcttttctgg caaccaaacc catacatcgg    2340
gattcctata ataccttcgt tggtctccct aacatgtagg tggcggaggg gagatataca    2400
atagaacaga taccagacaa gacataatgg gctaaacaag actacaccaa ttacactgcc    2460
tcattgatgg tggtacataa cgaactaata ctgtagccct agacttgata gccatcatca    2520
tatcgaagtt tcactacct ttttccattt gccatctatt gaagtaataa taggcgcatg     2580
caacttcttt tctttttttt tcttttctct ctccccccgtt gttgtctcac catatccgca   2640
atgacaaaaa aaatgatgga agacactaaa ggaaaaaatt aacgacaaag acagcaccaa    2700
cagatgtcgt tgttccagag ctgatgaggg gtatcttcga acacacgaaa cttttttcctt   2760 ccttcattca cgcacactac tctctaatga gcaacggtat acggccttcc ttccagttac    2820
ttgaatttga aataaaaaaa gtttgccgct ttgctatcaa gtataaatag acctgcaatt    2880
attaatcttt tgtttcctcg tcattgttct cgttcccttt cttccttgtt tcttttttctg   2940 cacaatattt caagctatac caagcataca atcaactatc tcatatacaa tcaaggaatt    3000
gatcatgtgg attgaacaag atggattgca cgcaggttct ccggccgctt gggtggagag    3060
gctattcggc tatgactggg cacaacagac aatcggctgc tctgatgccg ccgtgttccg    3120
gctgtcagcg caggggcgcc cggttctttt tgtcaagacc gacctgtccg gtgccctgaa    3180
tgaactgcag gacgaggcag cgcggctatc gtggctggcc acgacgggcg ttccttgcgc    3240
agctgtgctc gacgttgtca ctgaagcggg aagggactgg ctgctattgg gcgaagtgcc    3300
ggggcaggat ctcctgtcat ctcaccttgc tcctgccgag aaagtatcca tcatggctga    3360
tgcaatgcgg cggctgcata cgcttgatcc ggctacctgc ccattcgacc accaagcgaa    3420
acatcgcatc gagcgagcac gtactcggat ggaagccggt cttgtcgatc aggatgatct    3480
ggacgaagag catcaggggc tcgcgccagc cgaactgttc gccaggctca aggcgcgcat    3540
```

```
gcccgacggc gaggatctcg tcgtgaccca tggcgatgcc tgcttgccga atatcatggt    3600
ggaaaatggc cgcttttctg gattcatcga ctgtggccgg ctgggtgtgg cggaccgcta    3660
tcaggacata gcgttggcta cccgtgatat tgctgaagag cttggcggcg aatgggctga    3720
ccgcttcctc gtgctttacg gtatcgccgc tcccgattcg cagcgcatcg ccttctatcg    3780
ccttcttgac gagttcttct gagcgggact ctggggttcg aaatgaccga ccaagcgacg    3840
cccaacctgc catcacgaga tttcgattcc accgccgcct tctatgaaag gttgggcttc    3900
ggaatcgttt tccgggacgc cggctggatg atcctccagc gcgggatct catgctggag    3960 ttcttcgccc accccgggta ccgagctcga attaattcac tggccgtcgt tttacaacgt    4020
cgtgactggg aaaaccctgg cgttacccaa cttaatcgcc ttgcagcaca tccccctttc    4080
gccagctggg gtaatagcga agaggcccgc accgatcgcc cttcccaaca gttgcgcagc    4140
ctgaatggcg aatggcgcct gatgcggtat tttctcctta cgcatctgtg cggtatttca    4200
caccgcatat ggtgcactct cagtacaatc tgctctgatg ccgcatagtt aagccagccc    4260
cgacacccgc caacacccgc tgacgcgccc tgacgggctt gtctgctccc ggcatccgct    4320
tacagacaag ctgtgaccgt ctccgggagc tgcatgtgtc agaggttttc accgtcatca    4380
ccgaaacgcg cga                                                       4393

<210> SEQ ID NO 24
<211> LENGTH: 66
<212> TYPE: DNA
<213> ORGANISM: Artificial Sequence
<220> FEATURE:
<223> OTHER INFORMATION: primer URA3Km-L1

<400> SEQUENCE: 24
gaaggttaat gtggctgtgg tttcagggtc cataaagctt ccatcctttt gttgtttccg    60
ggtgta                                                               66

<210> SEQ ID NO 25
<211> LENGTH: 66
<212> TYPE: DNA
<213> ORGANISM: Artificial Sequence
<220> FEATURE:
<223> OTHER INFORMATION: primer URA3Km-R2

<400> SEQUENCE: 25
aggtattgga tagttccttt ttataaaggc catgaagctt tcagaagaac tcgtcaagaa    60
ggcgat                                                               66

<210> SEQ ID NO 26
<211> LENGTH: 18
<212> TYPE: DNA
<213> ORGANISM: Artificial Sequence
<220> FEATURE:
<223> OTHER INFORMATION: primer ura3up2

<400> SEQUENCE: 26
gaggctactg cgccaatt                                                  18

<210> SEQ ID NO 27
<211> LENGTH: 23
<212> TYPE: DNA
<213> ORGANISM: Artificial Sequence
<220> FEATURE:
<223> OTHER INFORMATION: primer ura3dn2
```

<400> SEQUENCE: 27

```
gaagtcattg acacagtctg tga                                          23
```

<210> SEQ ID NO 28
<211> LENGTH: 4575
<212> TYPE: DNA
<213> ORGANISM: Artificial Sequence
<220> FEATURE:
<223> OTHER INFORMATION: plasmid pKS-URA3-13

<400> SEQUENCE: 28

```
ctaaattgta agcgttaata ttttgttaaa attcgcgtta aattttttgtt aaatcagctc    60
atttttttaac caataggccg aaatcggcaa atcccttat aaatcaaaag aatagaccga   120
gatagggttg agtgttgttc cagtttggaa caagagtcca ctattaaaga acgtggactc   180
caacgtcaaa gggcgaaaaa ccgtctatca gggcgatggc ccactacgtg aaccatcacc   240
ctaatcaagt tttttggggt cgaggtgccg taaagcacta aatcggaacc ctaaagggag   300
cccccgattt agagcttgac ggggaaagcc ggcgaacgtg gcgagaaagg aagggaagaa   360
agcgaaagga gcgggcgcta gggcgctggc aagtgtagcg gtcacgctgc gcgtaaccac   420
cacacccgcc gcgcttaatg cgccgctaca gggcgcgtcc cattcgccat tcaggctgcg   480
caactgttgg gaagggcgat cggtgcgggc ctcttcgcta ttacgccagc tggcgaaagg   540
gggatgtgct gcaaggcgat taagttgggt aacgccaggg ttttcccagt cacgacgttg   600
taaaacgacg gccagtgagc gcgcgtaata cgactcacta gggcgaat tggagctcca    660
ccgcggtggc ggccgctcta gaactagtgg atccccccgaa gtcattgaca cagtctgtga   720
aacatctttc taccagatta gagtacaaac gcatgaaatc cttcatttgc ttttgttcca   780
ctacttttg gaactcttgt tgttctttgg agttcaatgc gtccatcttt acagtcctgt   840
cttattgttc ttgatttgtg ccccgtaaaa tactgttact tggttctggc gaggtattgg   900
atagttcctt tttataaagg ccatgaagct ttttctttcc aatttttttt ttttcgtcat   960
tatagaaatc attacgaccg agattccgg gtaataactg atataattaa attgaagctc  1020
taatttgtga gttagtata catgcattta cttataatac agttttttag ttttgctggc  1080
cgcatcttct caaatatgct tcccagcctg cttttctgta acgttcaccc tctaccttag  1140
catcccttcc ctttgcaaat agtcctcttc aacaataat aatgtcagat cctgtagaga  1200
ccacatcatc cacggttcta tactgttgac ccaatgcgtc tcccttgtca tctaaaccca  1260
caccgggtgt cataatcaac caatcgtaac cttcatctct tccacccatg tctctttgag  1320
caataaagcc gataacaaaa tctttgtcgc tcttcgcaat gtcaacagta cccttagtat  1380
attctccagt agctagggag cccttgcatg acaattctgc taacatcaaa aggcctctag  1440
gttcctttgt tacttcttcc gccgcctgct tcaaaccgct aacaatacct gggcccacca  1500
caccgtgtgc attcgtaatg tctgcccatt ctgctattct gtatacaccc gcagagtact  1560
gcaatttgac tgtattacca atgtcagcaa attttctgtc ttcgaagagt aaaaaattgt  1620
acttggcgga taatgccttt agcggcttaa ctgtgccctc catggaaaaa tcagtcaaga  1680
tatccacatg tgtttttagt aaacaaattt gggacctaa tgcttcaact aactccagta  1740
attccttggt ggtacgaaca tccaatgaag cacacaagtt tgtttgcttt tcgtgcatga  1800
tattaaatag cttggcagca acaggactag gatgagtagc agcacgttcc ttatatgtag  1860
ctttcgacat gatttatctt cgtttcctgc aggtttttgt tctgtgcagt tgggttaaga  1920
atactgggca atttcatgtt tcttcaacac cacatatgcg tatatatacc aatctaagtc  1980
```

| | | | | |
|---|---|---|---|---|
| tgtgctcctt | ccttcgttct | tccttctgct | cggagattac | cgaatcaaaa aaatttcaaa | 2040 |
| gaaaccggaa | tcaaaaaaaa | gaacaaaaaa | aaaaaagatg | aattgaaaag ctttatggac | 2100 |
| cctgaaacca | cagccacatt | aaccttcttt | gatggtcaaa | acttatcctt caccataaat | 2160 |
| atgcctcgca | aaaaaggtaa | ttaacatata | tagaattaca | ttatttatga aatatcatca | 2220 |
| ctatctctta | gcatctttaa | tccttttcta | catcagataa | cttcggtttg ttatcatcgt | 2280 |
| ctgtattgtc | atcaattggc | gcagtagcct | cgggctgcag | gaattcgata tcaagcttat | 2340 |
| cgataccgtc | gacctcgagg | gggggcccgg | tacccagctt | ttgttcccct tagtgagggt | 2400 |
| taattgcgcg | cttggcgtaa | tcatggtcat | agctgtttcc | tgtgtgaaat tgttatccgc | 2460 |
| tcacaattcc | acacaacata | cgagccggaa | gcataaagtg | taaagcctgg ggtgcctaat | 2520 |
| gagtgagcta | actcacatta | attgcgttgc | gctcactgcc | cgctttccag tcgggaaacc | 2580 |
| tgtcgtgcca | gctgcattaa | tgaatcggcc | aacgcgcggg | gagaggcggt ttgcgtattg | 2640 |
| ggcgctcttc | cgcttcctcg | ctcactgact | cgctgcgctc | ggtcgttcgg ctgcggcgag | 2700 |
| cggtatcagc | tcactcaaag | gcggtaatac | ggttatccac | agaatcaggg gataacgcag | 2760 |
| gaaagaacat | gtgagcaaaa | ggccagcaaa | aggccaggaa | ccgtaaaaag gccgcgttgc | 2820 |
| tggcgttttt | ccataggctc | cgcccccctg | acgagcatca | caaaaatcga cgctcaagtc | 2880 |
| agaggtggcg | aaacccgaca | ggactataaa | gataccaggc | gtttccccct ggaagctccc | 2940 |
| tcgtgcgctc | tcctgttccg | accctgccgc | ttaccggata | cctgtccgcc tttctccctt | 3000 |
| cgggaagcgt | ggcgctttct | catagctcac | gctgtaggta | tctcagttcg gtgtaggtcg | 3060 |
| ttcgctccaa | gctgggctgt | gtgcacgaac | cccccgttca | gcccgaccgc tgcgccttat | 3120 |
| ccggtaacta | tcgtcttgag | tccaacccgg | taagacacga | cttatcgcca ctggcagcag | 3180 |
| ccactggtaa | caggattagc | agagcgaggt | atgtaggcgg | tgctacagag ttcttgaagt | 3240 |
| ggtggcctaa | ctacggctac | actagaagga | cagtatttgg | tatctgcgct ctgctgaagc | 3300 |
| cagttacctt | cggaaaaaga | gttggtagct | cttgatccgg | caaacaaacc accgctggta | 3360 |
| gcggtggttt | ttttgtttgc | aagcagcaga | ttacgcgcag | aaaaaaagga tctcaagaag | 3420 |
| atcctttgat | cttttctacg | gggtctgacg | ctcagtggaa | cgaaaactca cgttaaggga | 3480 |
| ttttggtcat | gagattatca | aaaaggatct | tcacctagat | ccttttaaat taaaaatgaa | 3540 |
| gttttaaatc | aatctaaagt | atatatgagt | aaacttggtc | tgacagttac caatgcttaa | 3600 |
| tcagtgaggc | acctatctca | gcgatctgtc | tatttcgttc | atccatagtt gcctgactcc | 3660 |
| ccgtcgtgta | gataactacg | atacgggagg | gcttaccatc | tggccccagt gctgcaatga | 3720 |
| taccgcgaga | cccacgctca | ccggctccag | atttatcagc | aataaaccag ccagccggaa | 3780 |
| gggccgagcg | cagaagtggt | cctgcaactt | tatccgcctc | catccagtct attaattgtt | 3840 |
| gccgggaagc | tagagtaagt | agttcgccag | ttaatagttt | gcgcaacgtt gttgccattg | 3900 |
| ctacaggcat | cgtggtgtca | cgctcgtcgt | ttggtatggc | ttcattcagc tccgttccc | 3960 |
| aacgatcaag | gcgagttaca | tgatccccca | tgttgtgcaa | aaaagcggtt agctccttcg | 4020 |
| gtcctccgat | cgttgtcaga | agtaagttgg | ccgcagtgtt | atcactcatg gttatggcag | 4080 |
| cactgcataa | ttctcttact | gtcatgccat | ccgtaagatg | cttttctgtg actggtgagt | 4140 |
| actcaaccaa | gtcattctga | gaatagtgta | tgcggcgacc | gagttgctct tgcccggcgt | 4200 |
| caatacggga | taataccgcg | ccacatagca | gaactttaaa | agtgctcatc attggaaaac | 4260 |
| gttcttcggg | gcgaaaactc | tcaaggatct | taccgctgtt | gagatccagt tcgatgtaac | 4320 |

```
ccactcgtgc acccaactga tcttcagcat ctttttacttt caccagcgtt tctgggtgag    4380
caaaaacagg aaggcaaaat gccgcaaaaa agggaataag ggcgacacgg aaatgttgaa    4440
tactcatact cttcctttt caatattatt gaagcattta tcagggttat tgtctcatga    4500
gcggatacat atttgaatgt atttagaaaa ataaacaaat aggggttccg cgcacatttc    4560
cccgaaaagt gccac                                                     4575

<210> SEQ ID NO 29
<211> LENGTH: 6002
<212> TYPE: DNA
<213> ORGANISM: Artificial Sequence
<220> FEATURE:
<223> OTHER INFORMATION: plasmid pKS-URA3-13-kanMX

<400> SEQUENCE: 29
ctaaattgta agcgttaata ttttgttaaa attcgcgtta aatttttgtt aaatcagctc      60
attttttaac caataggccg aaatcggcaa aatcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt ttttttgggt cgaggtgccg taaagcacta atcggaacc ctaaagggag    300 cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tggagctcca    660
ccgcggtggc ggccgctcta gaactagtgg atccccgaa gtcattgaca cagtctgtga    720
aacatctttc taccagatta gagtacaaac gcatgaaatc cttcatttgc ttttgttcca    780
ctactttttg gaactcttgt tgttctttgg agttcaatgc gtccatcttt acagtcctgt    840
cttattgttc ttgatttgtg ccccgtaaaa tactgttact tggttctggc gaggtattgg    900
atagttcctt tttataaagg ccatgaagct ttttctttcc aattttttt ttttcgtcat    960 tatagaaatc attacgaccg agattccccgg gtaataactg atataattaa attgaagctc    1020
taatttgtga gtttagtata catgcattta cttataatac agttttttag ttttgctggc    1080
cgcatcttct caaatatgct tcccagcctg ctttctgta acgttcaccc tctaccttag    1140
catcccttcc ctttgcaaat agtcctcttc caacaataat aatgtcagat cctgtagaga    1200
ccacatcatc cacggttcta tactgttgac ccaatgcgtc tcccttgtca tctaaaccca    1260
caccgggtgt cataatcaac caatcgtaac cttcatctct tccacccatg tctctttgag    1320
caataaagcc gataacaaaa tctttgtcgc tcttcgcaat gtcaacagta cccttagtat    1380
attctccagt agctagggag cccttgcatg acaattctgc taacatcaaa aggcctgtcg    1440 acaacccta atataacttc gtataatgta tgctatacga agttattagg tctagagatc    1500
tgtttagctt gcctcgtccc cgccgggtca cccggccagc gacatggagg cccagaatac    1560
cctccttgac agtcttgacg tgcgcagctc agggcgatga tgtgactgtc gcccgtacat    1620
ttagcccata catccccatg tataatcatt tgcatccata catttgatg gccgcacggc    1680 gcgaagcaaa aattacggct cctcgctgca gacctgcgag cagggaaacg ctccctcac    1740 agacgcgttg aattgtcccc acgccgcgcc cctgtagaga aatataaaag gttaggattt    1800
```

```
gccactgagg ttcttctttc atatacttcc ttttaaaatc ttgctaggat acagttctca   1860
catcacatcc gaacataaac aaccatgggt aaggaaaaga ctcacgtttc gaggccgcga   1920
ttaaattcca acatggatgc tgatttatat gggtataaat gggctcgcga taatgtcggg   1980
caatcaggtg cgacaatcta tcgattgtat gggaagcccg atgcgccaga gttgtttctg   2040
aaacatggca aaggtagcgt tgccaatgat gttacagatg agatggtcag actaaactgg   2100
ctgacggaat ttatgcctct tccgaccatc aagcatttta tccgtactcc tgatgatgca   2160
tggttactca ccactgcgat ccccggcaaa acagcattcc aggtattaga agaatatcct   2220
gattcaggtg aaaatattgt tgatgcgctg gcagtgttcc tgcgccggtt gcattcgatt   2280
cctgtttgta attgtccttt taacagcgat cgcgtatttc gtctcgctca ggcgcaatca   2340
cgaatgaata acggtttggt tgatgcgagt gattttgatg acgagcgtaa tggctggcct   2400
gttgaacaag tctggaaaga atgcataag cttttgccat tctcaccgga ttcagtcgtc   2460
actcatggtg atttctcact tgataacctt attttttgacg aggggaaatt aataggttgt   2520
attgatgttg gacgagtcgg aatcgcagac cgataccagg atcttgccat cctatggaac   2580
tgcctcggtg agttttctcc ttcattacag aaacggcttt ttcaaaaata tggtattgat   2640
aatcctgata tgaataaatt gcagtttcat ttgatgctcg atgagttttt ctaatcagta   2700
ctgacaataa aaagattctt gttttcaaga acttgtcatt tgtatagttt tttatattg    2760
tagttgttct attttaatca aatgttagcg tgatttatat ttttttttcgc ctcgacatca   2820
tctgcccaga tgcgaagtta agtgcgcaga aagtaatatc atgcgtcaat cgtatgtgaa   2880
tgctggtcgc tatactgctg tcgattcgat actaacgccg ccatccagtg tcgaaaacga   2940
gctctcgaga acccttaata taacttcgta taatgtatgc tatacgaagt tattaggtga   3000
tatcagatcc actagtggcc tatgcggccg cggatctgcc ggtctcccta tagtgagtcg   3060
tattaatttc gataagccag gttaacccat ggaaaaatca gtcaagatat ccacatgtgt   3120
ttttagtaaa caaattttgg gacctaatgc ttcaactaac tccagtaatt ccttggtggt   3180
acgaacatcc aatgaagcac acaagtttgt ttgcttttcg tgcatgatat taaaatagctt  3240
ggcagcaaca ggactaggat gagtagcagc acgttcctta tatgtagctt tcgacatgat   3300
ttatcttcgt ttcctgcagg ttttgttct gtgcagttgg gttaagaata ctgggcaatt   3360
tcatgttttct tcaacaccac atatgcgtat atataccaat ctaagtctgt gctccttcct   3420
tcgttcttcc ttctgctcgg agattaccga atcaaaaaaa tttcaaagaa accggaatca   3480
aaaaaagaa caaaaaaaaa aaagatgaat tgaaagctt tatggaccct gaaaccacag   3540
ccacattaac cttctttgat ggtcaaaact tatccttcac cataaatatg cctcgcaaaa   3600
aagtaatta acatatatag aattacatta tttatgaaat atcatcacta tctcttagca   3660
tcttaatcc ttttctacat cagataactt cggtttgtta tcatcgtctg tattgtcatc    3720
aattggcgca gtagcctcgg gctgcaggaa ttcgatatca agcttatcga taccgtcgac   3780
ctcgaggggg ggcccggtac ccagcttttg ttccctttag tgagggttaa ttgcgcgctt   3840
ggcgtaatca tggtcatagc tgtttcctgt gtgaaattgt tatccgctca caattccaca   3900
caacatacga gccggaagca taaagtgtaa agcctggggt gcctaatgag tgagctaact   3960
cacattaatt gcgttgcgct cactgcccgc tttccagtcg ggaaacctgt cgtgccagct   4020
gcattaatga atcggccaac gcgcgggag aggcggtttg cgtattgggc gctcttccgc    4080
ttcctcgctc actgactcgc tgcgctcggt cgttcggctg cggcgagcgg tatcagctca   4140
```

```
ctcaaaggcg gtaatacggt tatccacaga atcaggggat aacgcaggaa agaacatgtg    4200
agcaaaaggc cagcaaaagg ccaggaaccg taaaaaggcc gcgttgctgg cgttttttcca   4260 taggctccgc cccctgacg agcatcacaa aaatcgacgc tcaagtcaga ggtggcgaaa     4320
cccgacagga ctataaagat accaggcgtt tccccctgga agctccctcg tgcgctctcc    4380
tgttccgacc ctgccgctta ccggatacct gtccgccttt ctcccttcgg gaagcgtggc    4440
gctttctcat agctcacgct gtaggtatct cagttcggtg taggtcgttc gctccaagct    4500
gggctgtgtg cacgaacccc ccgttcagcc cgaccgctgc gccttatccg gtaactatcg    4560
tcttgagtcc aacccggtaa gacacgactt atcgccactg gcagcagcca ctggtaacag    4620
gattagcaga gcgaggtatg taggcggtgc tacagagttc ttgaagtggt ggcctaacta    4680
cggctacact agaaggacag tatttggtat ctgcgctctg ctgaagccag ttaccttcgg    4740
aaaaagagtt ggtagctctt gatccggcaa acaaaccacc gctggtagcg tggtttttt    4800 tgtttgcaag cagcagatta cgcgcagaaa aaaaggatct caagaagatc ctttgatctt    4860
ttctacgggg tctgacgctc agtggaacga aaactcacgt taagggattt tggtcatgag    4920
attatcaaaa aggatcttca cctagatcct tttaaattaa aaatgaagtt ttaaatcaat    4980
ctaaagtata tatgagtaaa cttggtctga cagttaccaa tgcttaatca gtgaggcacc    5040
tatctcagcg atctgtctat ttcgttcatc catagttgcc tgactccccg tcgtgtagat    5100
aactacgata cgggagggct taccatctgg ccccagtgct gcaatgatac cgcgagaccc    5160
acgctcaccg gctccagatt tatcagcaat aaaccagcca gccggaaggg ccgagcgcag    5220
aagtggtcct gcaactttat ccgcctccat ccagtctatt aattgttgcc gggaagctag    5280
agtaagtagt tcgccagtta atagtttgcg caacgttgtt gccattgcta caggcatcgt    5340
ggtgtcacgc tcgtcgtttg gtatggcttc attcagctcc ggttcccaac gatcaaggcg    5400
agttacatga tcccccatgt tgtgcaaaaa agcggttagc tccttcggtc ctccgatcgt    5460
tgtcagaagt aagttggccg cagtgttatc actcatggtt atggcagcac tgcataattc    5520
tcttactgtc atgccatccg taagatgctt ttctgtgact ggtgagtact caaccaagtc    5580
attctgagaa tagtgtatgc ggcgaccgag ttgctcttgc ccggcgtcaa tacgggataa    5640
taccgcgcca catagcagaa ctttaaaagt gctcatcatt ggaaaacgtt cttcggggcg    5700
aaaactctca aggatcttac cgctgttgag atccagttcg atgtaaccca ctcgtgcacc    5760
caactgatct tcagcatctt ttactttcac cagcgtttct gggtgagcaa aaacaggaag    5820
gcaaaatgcc gcaaaaaagg aataagggc gacacggaaa tgttgaatac tcatactctt    5880
cctttttcaa tattattgaa gcatttatca gggttattgt ctcatgagcg gatacatatt    5940
tgaatgtatt tagaaaaata aacaaatagg ggttccgcgc acatttcccc gaaaagtgcc    6000
ac                                                                   6002
```

<210> SEQ ID NO 30
<211> LENGTH: 66
<212> TYPE: DNA
<213> ORGANISM: Artificial Sequence
<220> FEATURE:
<223> OTHER INFORMATION: primer hgt1-pUG6u

<400> SEQUENCE: 30

```
ggaaagccaa aaattcgaca ggcattccat acaggaggaa ggtctcgcag ctgaagcttc      60
gtacgc                                                                66
```

<210> SEQ ID NO 31
<211> LENGTH: 66
<212> TYPE: DNA
<213> ORGANISM: Artificial Sequence
<220> FEATURE:
<223> OTHER INFORMATION: primer hgt1-pUG6d

<400> SEQUENCE: 31
ttgccacacc tgcttcaaca ccggccccca tgacgaaatt gtacgcatag gccactagtg    60
gatctg                                                              66

<210> SEQ ID NO 32
<211> LENGTH: 22
<212> TYPE: DNA
<213> ORGANISM: Artificial Sequence
<220> FEATURE:
<223> OTHER INFORMATION: primer hgt1-51

<400> SEQUENCE: 32
ttaatcacat caaacccact gc                                            22

<210> SEQ ID NO 33
<211> LENGTH: 22
<212> TYPE: DNA
<213> ORGANISM: Artificial Sequence
<220> FEATURE:
<223> OTHER INFORMATION: primer hgt1-33

<400> SEQUENCE: 33
ccgatgattg tccatatata gt                                            22

<210> SEQ ID NO 34
<211> LENGTH: 66
<212> TYPE: DNA
<213> ORGANISM: Artificial Sequence
<220> FEATURE:
<223> OTHER INFORMATION: primer ptr2-pUG6u

<400> SEQUENCE: 34
gccactgggt tgtcgtattt tttccagttt tggtgttacg ttacacccag ctgaagcttc    60
gtacgc                                                              66

<210> SEQ ID NO 35
<211> LENGTH: 66
<212> TYPE: DNA
<213> ORGANISM: Artificial Sequence
<220> FEATURE:
<223> OTHER INFORMATION: primer ptr2-pUG6d

<400> SEQUENCE: 35
aaagaaatca agacatatgc gggtatttgc cagcaaacgt ggacgcatag gccactagtg    60
gatctg                                                              66

<210> SEQ ID NO 36
<211> LENGTH: 18
<212> TYPE: DNA
<213> ORGANISM: Artificial Sequence
<220> FEATURE:
<223> OTHER INFORMATION: primer ptr2-51

<400> SEQUENCE: 36
atgctcaacc atcccagc                                                 18

<210> SEQ ID NO 37

```
<211> LENGTH: 18
<212> TYPE: DNA
<213> ORGANISM: Artificial Sequence
<220> FEATURE:
<223> OTHER INFORMATION: primer ptr2-31

<400> SEQUENCE: 37
cccgtcaacg taatatgg                                                    18

<210> SEQ ID NO 38
<211> LENGTH: 25
<212> TYPE: DNA
<213> ORGANISM: Artificial Sequence
<220> FEATURE:
<223> OTHER INFORMATION: primer adh1L1

<400> SEQUENCE: 38
atttcggata tccttttgtt gtttc                                             25

<210> SEQ ID NO 39
<211> LENGTH: 25
<212> TYPE: DNA
<213> ORGANISM: Artificial Sequence
<220> FEATURE:
<223> OTHER INFORMATION: primer adh1R1

<400> SEQUENCE: 39
tgtatatgag atagttgatt gtatg                                             25

<210> SEQ ID NO 40
<211> LENGTH: 66
<212> TYPE: DNA
<213> ORGANISM: Artificial Sequence
<220> FEATURE:
<223> OTHER INFORMATION: primer PADH1-HGT1

<400> SEQUENCE: 40
ccgactccaa cgagtcgctc tccctataaa tggtactcat tgtatatgag atagttgatt       60
gtatgc                                                                 66

<210> SEQ ID NO 41
<211> LENGTH: 65
<212> TYPE: DNA
<213> ORGANISM: Artificial Sequence
<220> FEATURE:
<223> OTHER INFORMATION: primer HGT1-PADH1

<400> SEQUENCE: 41
attcaatgaa ttgtttcgac tatatatgga caatcatcgg atttcggata tccttttgtt       60
gtttc                                                                  65

<210> SEQ ID NO 42
<211> LENGTH: 22
<212> TYPE: DNA
<213> ORGANISM: Artificial Sequence
<220> FEATURE:
<223> OTHER INFORMATION: primer hgt53

<400> SEQUENCE: 42
gatcgatact aacttccgag ac                                                22

<210> SEQ ID NO 43
<211> LENGTH: 22
<212> TYPE: DNA
<213> ORGANISM: Artificial Sequence
```

```
<220> FEATURE:
<223> OTHER INFORMATION: primer hgt33

<400> SEQUENCE: 43
ccgatgattg tccatatata gt                                              22

<210> SEQ ID NO 44
<211> LENGTH: 19
<212> TYPE: DNA
<213> ORGANISM: Artificial Sequence
<220> FEATURE:
<223> OTHER INFORMATION: primer ptr52

<400> SEQUENCE: 44
ggctgcttct ccctttca                                                   19

<210> SEQ ID NO 45
<211> LENGTH: 18
<212> TYPE: DNA
<213> ORGANISM: Artificial Sequence
<220> FEATURE:
<223> OTHER INFORMATION: primer ptr32

<400> SEQUENCE: 45
ttgcagtgga gcagcact                                                   18

<210> SEQ ID NO 46
<211> LENGTH: 55
<212> TYPE: DNA
<213> ORGANISM: Artificial Sequence
<220> FEATURE:
<223> OTHER INFORMATION: primer PTR2-PADH1

<400> SEQUENCE: 46
aaggtatacc acagtgctgc tccactgcaa atttcggata tccttttgtt gtttc          55

<210> SEQ ID NO 47
<211> LENGTH: 66
<212> TYPE: DNA
<213> ORGANISM: Artificial Sequence
<220> FEATURE:
<223> OTHER INFORMATION: primer PADH1-PTR2

<400> SEQUENCE: 47
cctgagcatc atctgagcct tggctgggat ggttgagcat tgtatatgag atagttgatt     60
gtatgc                                                                66

<210> SEQ ID NO 48
<211> LENGTH: 31
<212> TYPE: DNA
<213> ORGANISM: Artificial Sequence
<220> FEATURE:
<223> OTHER INFORMATION: primer tdh3-EcoR1

<400> SEQUENCE: 48
tggaattcaa acacgctttt tcagttcgag t                                    31

<210> SEQ ID NO 49
<211> LENGTH: 31
<212> TYPE: DNA
<213> ORGANISM: Artificial Sequence
<220> FEATURE:
<223> OTHER INFORMATION: primer tdh3-Pci1

<400> SEQUENCE: 49
```
acacatgttg tttgtttatg tgtgtttatt c        31

<210> SEQ ID NO 50
<211> LENGTH: 66
<212> TYPE: DNA
<213> ORGANISM: Artificial Sequence
<220> FEATURE:
<223> OTHER INFORMATION: primer GSH1-pUG

<400> SEQUENCE: 50
ggtctcgagt cacttgtaga agctgaaaat tgagcagatt tagtgcatag gccactagtg        60
gatctg        66

<210> SEQ ID NO 51
<211> LENGTH: 66
<212> TYPE: DNA
<213> ORGANISM: Artificial Sequence
<220> FEATURE:
<223> OTHER INFORMATION: primer PTDH3-GSH1

<400> SEQUENCE: 51
gactcaaacc actgcaaagg cgtgcccaaa gctaagagtc ccatgttgtt tgtttatgtg        60
tgttta        66

<210> SEQ ID NO 52
<211> LENGTH: 62
<212> TYPE: DNA
<213> ORGANISM: Artificial Sequence
<220> FEATURE:
<223> OTHER INFORMATION: primer PTDH3-GSH2

<400> SEQUENCE: 52
attcattcaa ttgatccttg gaaggtggat agtgtgccat gttgtttgtt tatgtgtgtt        60
ta        62

<210> SEQ ID NO 53
<211> LENGTH: 72
<212> TYPE: DNA
<213> ORGANISM: Artificial Sequence
<220> FEATURE:
<223> OTHER INFORMATION: primer GSH2-pUG

<400> SEQUENCE: 53
gatcctccaa aggtagcaaa gtgccacttc aagcaattat aggaagaaag gcataggcca        60
ctagtggatc tg        72

<210> SEQ ID NO 54
<211> LENGTH: 20
<212> TYPE: DNA
<213> ORGANISM: Artificial Sequence
<220> FEATURE:
<223> OTHER INFORMATION: primer GSH2up2

<400> SEQUENCE: 54
ccacatcttc taatatggat        20

<210> SEQ ID NO 55
<211> LENGTH: 20
<212> TYPE: DNA
<213> ORGANISM: Artificial Sequence
<220> FEATURE:
<223> OTHER INFORMATION: primer GSH2d_tail

<400> SEQUENCE: 55
ctttcttcct ataattgctt                                          20

<210> SEQ ID NO 56
<211> LENGTH: 65
<212> TYPE: DNA
<213> ORGANISM: Artificial Sequence
<220> FEATURE:
<223> OTHER INFORMATION: primer yepgsh2-F

<400> SEQUENCE: 56
cccgcgccca ccggaaggag ctgactgggt tgaaggctct caaggcgaag ttatattaag    60
ggttg                                                                65

<210> SEQ ID NO 57
<211> LENGTH: 65
<212> TYPE: DNA
<213> ORGANISM: Artificial Sequence
<220> FEATURE:
<223> OTHER INFORMATION: primer yepgsh2-R

<400> SEQUENCE: 57
tcgcttcgct acttggagcc actatcgact acgcgatcat ggcgatcatc ttcctagcat    60
ctatg                                                                65

<210> SEQ ID NO 58
<211> LENGTH: 2806
<212> TYPE: DNA
<213> ORGANISM: Saccharomyces cerevisiae
<220> FEATURE:
<221> NAME/KEY: CDS
<222> LOCATION: (501)..(2306)

<400> SEQUENCE: 58
gttcaggatc ctcgaagaac aggaaaaagg acaaccgtcc ttttcacttc acgttcgcag    60
ggctttcctc gatataatgg cgattacaca agcggtggcg tcttgaaaaa agttgggttt   120
cttatctgta cggcgatcac tcccctcata tgatagctgt gtagagtgac ttgctctttg   180
attggcctta cttcttgcat ctatcatcct ttctttttact ctctccaatc accacaactc   240
atatcattct acatttcatt ttattgttct gtacaatttt taggtttgta aaatatataa   300
gtgatgtaca tatcttctat atcctttccg tttgtgtcta ttttagggtt ggcttattac   360
gcattattcc tactttattt ttacttgctt acttgaaaaa gaaggtatac cacagtgctg   420
ctccactgca acaatataa aatattatca attattttt tttttcttct tttgaattag    480
atcactaata aactcttata atg ctc aac cat ccc agc caa ggc tca gat gat    533
                       Met Leu Asn His Pro Ser Gln Gly Ser Asp Asp
                        1               5                  10 gct cag gac gaa aag caa ggc gac ttc ccg gtc atc gaa gag gag aag      581
Ala Gln Asp Glu Lys Gln Gly Asp Phe Pro Val Ile Glu Glu Glu Lys
                15                  20                  25 acc cag gct gta acg ctg aag gat tcg tat gtt agc gac gac gtc gcc      629
Thr Gln Ala Val Thr Leu Lys Asp Ser Tyr Val Ser Asp Asp Val Ala
            30                  35                  40 aac tcc acg gaa cgc tac aac ttg tcc cct tct ccg gag gac gaa gac      677
Asn Ser Thr Glu Arg Tyr Asn Leu Ser Pro Ser Pro Glu Asp Glu Asp
        45                  50                  55 ttc gaa ggc ccc act gaa gaa gaa atg cag act tta agg cac gtt ggt      725
Phe Glu Gly Pro Thr Glu Glu Glu Met Gln Thr Leu Arg His Val Gly
    60                  65                  70                  75 ggt aaa att cct atg agg tgt tgg tta att gct att gta gag ctt tcc      773

```
                Gly Lys Ile Pro Met Arg Cys Trp Leu Ile Ala Ile Val Glu Leu Ser
                                80                  85                  90 gag aga ttc tcc tac tac ggg ctt tcc gca cca ttc caa aac tac atg          821
Glu Arg Phe Ser Tyr Tyr Gly Leu Ser Ala Pro Phe Gln Asn Tyr Met
            95                  100                 105 gaa tat gga cct aat gac tcc cca aag ggt gtt ctg agc ttg aac agt          869
Glu Tyr Gly Pro Asn Asp Ser Pro Lys Gly Val Leu Ser Leu Asn Ser
        110                 115                 120 cag ggt gcc act ggg ttg tcg tat ttt ttc cag ttt tgg tgt tac gtt          917
Gln Gly Ala Thr Gly Leu Ser Tyr Phe Phe Gln Phe Trp Cys Tyr Val
    125                 130                 135 aca cca gtt ttc ggt ggt tac gtt gcg gac acc ttc tgg ggt aaa tat          965
Thr Pro Val Phe Gly Gly Tyr Val Ala Asp Thr Phe Trp Gly Lys Tyr
140                 145                 150                 155 aat aca att tgt tgc ggt acc gct att tac att gcc ggt att ttc att         1013
Asn Thr Ile Cys Cys Gly Thr Ala Ile Tyr Ile Ala Gly Ile Phe Ile
                160                 165                 170 cta ttt atc act tcg att ccc tcc gtt ggt aac aga gac agt gct att         1061
Leu Phe Ile Thr Ser Ile Pro Ser Val Gly Asn Arg Asp Ser Ala Ile
            175                 180                 185 ggt ggg ttc att gct gcc att att ctg atc ggt att gcc act ggt atg         1109
Gly Gly Phe Ile Ala Ala Ile Ile Leu Ile Gly Ile Ala Thr Gly Met
        190                 195                 200 att aaa gct aac ctt tcc gtg ttg att gcc gac cag ctt cct aag cgg         1157
Ile Lys Ala Asn Leu Ser Val Leu Ile Ala Asp Gln Leu Pro Lys Arg
    205                 210                 215 aaa ccc tcc atc aaa gtt tta aaa tcg ggc gaa aga gtc att gtc gat         1205
Lys Pro Ser Ile Lys Val Leu Lys Ser Gly Glu Arg Val Ile Val Asp
220                 225                 230                 235 tca aat att act tta caa aac gtt ttt atg ttc ttc tat ttc atg atc         1253
Ser Asn Ile Thr Leu Gln Asn Val Phe Met Phe Phe Tyr Phe Met Ile
                240                 245                 250 aat gtc ggt tct cta tca tta atg gcc act act gaa ttg gaa tat cat         1301
Asn Val Gly Ser Leu Ser Leu Met Ala Thr Thr Glu Leu Glu Tyr His
            255                 260                 265 aag ggg ttc tgg gcg gcc tat cta ttg ccc ttc tgc ttc ttt tgg atc         1349
Lys Gly Phe Trp Ala Ala Tyr Leu Leu Pro Phe Cys Phe Phe Trp Ile
        270                 275                 280 gct gtt gtc act ttg att ttt ggt aaa aag caa tac att caa aga cca         1397
Ala Val Val Thr Leu Ile Phe Gly Lys Lys Gln Tyr Ile Gln Arg Pro
    285                 290                 295 atc gga gat aaa gtc atc gct aaa agt ttt aaa gtt tgt tgg att tta         1445
Ile Gly Asp Lys Val Ile Ala Lys Ser Phe Lys Val Cys Trp Ile Leu
300                 305                 310                 315 act aag aat aag ttc gac ttc aac gct gct aaa cct tct gtt cat cca         1493
Thr Lys Asn Lys Phe Asp Phe Asn Ala Ala Lys Pro Ser Val His Pro
                320                 325                 330 gaa aag aac tat cca tgg aat gac aaa ttt gtt gat gaa att aag aga         1541
Glu Lys Asn Tyr Pro Trp Asn Asp Lys Phe Val Asp Glu Ile Lys Arg
            335                 340                 345 gct ttg gcg gct tgt aaa gtc ttt ata ttc tac cca att tat tgg acc         1589
Ala Leu Ala Ala Cys Lys Val Phe Ile Phe Tyr Pro Ile Tyr Trp Thr
        350                 355                 360 caa tac ggt acc atg att tcc agt ttc atc act cag gcc agt atg atg         1637
Gln Tyr Gly Thr Met Ile Ser Ser Phe Ile Thr Gln Ala Ser Met Met
    365                 370                 375 gaa tta cat gga att ccc aac gat ttc tta caa gca ttc gat tcc att         1685
Glu Leu His Gly Ile Pro Asn Asp Phe Leu Gln Ala Phe Asp Ser Ile
380                 385                 390                 395
```

```
gcg ttg atc att ttc atc cca att ttt gaa aaa ttc gta tat cct ttc      1733
Ala Leu Ile Ile Phe Ile Pro Ile Phe Glu Lys Phe Val Tyr Pro Phe
            400                 405                 410 att aga aga tac act cca cta aaa cca att aca aaa att ttc ttc ggt      1781
Ile Arg Arg Tyr Thr Pro Leu Lys Pro Ile Thr Lys Ile Phe Phe Gly
        415                 420                 425 ttc atg ttt gga tct ttt gcc atg aca tgg gct gct gtt cta caa agt      1829
Phe Met Phe Gly Ser Phe Ala Met Thr Trp Ala Ala Val Leu Gln Ser
    430                 435                 440 ttc gtt tac aag gct ggt cca tgg tat aat gaa cct ctg ggt cac aac      1877
Phe Val Tyr Lys Ala Gly Pro Trp Tyr Asn Glu Pro Leu Gly His Asn
445                 450                 455 acc cca aat cat gtc cac gtt tgc tgg caa ata ccc gca tat gtc ttg      1925
Thr Pro Asn His Val His Val Cys Trp Gln Ile Pro Ala Tyr Val Leu
460                 465                 470                 475 att tct ttt tca gag atc ttt gcc tct atc act ggg ttg gaa tac gct      1973
Ile Ser Phe Ser Glu Ile Phe Ala Ser Ile Thr Gly Leu Glu Tyr Ala
            480                 485                 490 tat tcc aaa gcc cca gct tcc atg aaa tcg ttt att atg tcc att ttc      2021
Tyr Ser Lys Ala Pro Ala Ser Met Lys Ser Phe Ile Met Ser Ile Phe
        495                 500                 505 tta ttg act aac gcc ttt ggt tct gca atc ggt tgt gca ttg tcc cca      2069
Leu Leu Thr Asn Ala Phe Gly Ser Ala Ile Gly Cys Ala Leu Ser Pro
    510                 515                 520 gtg acc gtt gat cct aaa ttt aca tgg tta ttc act ggt ttg gct gtt      2117
Val Thr Val Asp Pro Lys Phe Thr Trp Leu Phe Thr Gly Leu Ala Val
525                 530                 535 gcc tgc ttt att tct ggt tgt ttg ttc tgg ttg tgc ttc agg aag tat      2165
Ala Cys Phe Ile Ser Gly Cys Leu Phe Trp Leu Cys Phe Arg Lys Tyr
540                 545                 550                 555 aat gat aca gag gaa gaa atg aac gct atg gac tac gaa gaa gaa gac      2213
Asn Asp Thr Glu Glu Glu Met Asn Ala Met Asp Tyr Glu Glu Glu Asp
            560                 565                 570 gaa ttt gat ctc aat cca att tcc gca cct aaa gct aac gat att gaa      2261
Glu Phe Asp Leu Asn Pro Ile Ser Ala Pro Lys Ala Asn Asp Ile Glu
        575                 580                 585 ata tta gaa cca atg gaa agt cta aga tcc acc acc aaa tat tag          2306
Ile Leu Glu Pro Met Glu Ser Leu Arg Ser Thr Thr Lys Tyr
    590                 595                 600 tgcgtttaat taacttactg tcttttttttt tttttttttt ttaaccatat tacgttgacg   2366
ggagttttct gtgctgctgt tatttgtttc acagaactct ctcctcttcc attgctatcg   2426
aacagataaa atggaatttc tttatgtata attactattg tataatattc agtaaatcta   2486
aattttaagc tcatatatct aaacactaca acatggaagc agcttgtcct cttcaggctc   2546
actgtatccg tttactctta tttgcgcgtat ttgcatacca ttatctcaaa tgacttgtta   2606
ttatatcttg atatatattg tattatagaa caatttgtga agagaggtcc atattaagat   2666
ttcctcccat ttacaaatag aatagaaaag gaaatatata tgtagtaaaa aaatcgtgat   2726
gtatacaaac tttggatttg tggagatcgt aataaatcga ttatttcaac ttcttctttg   2786
gacgcaattg gttggtgtga                                               2806

<210> SEQ ID NO 59
<211> LENGTH: 601
<212> TYPE: PRT
<213> ORGANISM: Saccharomyces cerevisiae

<400> SEQUENCE: 59

Met Leu Asn His Pro Ser Gln Gly Ser Asp Asp Ala Gln Asp Glu Lys
```

-continued

```
1               5                    10                   15
Gln Gly Asp Phe Pro Val Ile Glu Glu Lys Thr Gln Ala Val Thr
                20                  25                  30

Leu Lys Asp Ser Tyr Val Ser Asp Val Ala Asn Ser Thr Glu Arg
                35                  40                  45

Tyr Asn Leu Ser Pro Ser Pro Glu Asp Glu Asp Phe Glu Gly Pro Thr
                50                  55                  60

Glu Glu Glu Met Gln Thr Leu Arg His Val Gly Gly Lys Ile Pro Met
65                  70                  75                  80

Arg Cys Trp Leu Ile Ala Ile Val Glu Leu Ser Glu Arg Phe Ser Tyr
                85                  90                  95

Tyr Gly Leu Ser Ala Pro Phe Gln Asn Tyr Met Glu Tyr Gly Pro Asn
                100                 105                 110

Asp Ser Pro Lys Gly Val Leu Ser Leu Asn Ser Gln Gly Ala Thr Gly
                115                 120                 125

Leu Ser Tyr Phe Phe Gln Phe Trp Cys Tyr Val Thr Pro Val Phe Gly
                130                 135                 140

Gly Tyr Val Ala Asp Thr Phe Trp Gly Lys Tyr Asn Thr Ile Cys Cys
145                 150                 155                 160

Gly Thr Ala Ile Tyr Ile Ala Gly Ile Phe Ile Leu Phe Ile Thr Ser
                165                 170                 175

Ile Pro Ser Val Gly Asn Arg Asp Ser Ala Ile Gly Gly Phe Ile Ala
                180                 185                 190

Ala Ile Ile Leu Ile Gly Ile Ala Thr Gly Met Ile Lys Ala Asn Leu
                195                 200                 205

Ser Val Leu Ile Ala Asp Gln Leu Pro Lys Arg Lys Pro Ser Ile Lys
                210                 215                 220

Val Leu Lys Ser Gly Glu Arg Val Ile Val Asp Ser Asn Ile Thr Leu
225                 230                 235                 240

Gln Asn Val Phe Met Phe Phe Tyr Phe Met Ile Asn Val Gly Ser Leu
                245                 250                 255

Ser Leu Met Ala Thr Thr Glu Leu Glu Tyr His Lys Gly Phe Trp Ala
                260                 265                 270

Ala Tyr Leu Leu Pro Phe Cys Phe Phe Trp Ile Ala Val Val Thr Leu
                275                 280                 285

Ile Phe Gly Lys Lys Gln Tyr Ile Gln Arg Pro Ile Gly Asp Lys Val
                290                 295                 300

Ile Ala Lys Ser Phe Lys Val Cys Trp Ile Leu Thr Lys Asn Lys Phe
305                 310                 315                 320

Asp Phe Asn Ala Ala Lys Pro Ser Val His Pro Glu Lys Asn Tyr Pro
                325                 330                 335

Trp Asn Asp Lys Phe Val Asp Glu Ile Lys Arg Ala Leu Ala Ala Cys
                340                 345                 350

Lys Val Phe Ile Phe Tyr Pro Ile Tyr Trp Thr Gln Tyr Gly Thr Met
                355                 360                 365

Ile Ser Ser Phe Ile Thr Gln Ala Ser Met Met Glu Leu His Gly Ile
370                 375                 380

Pro Asn Asp Phe Leu Gln Ala Phe Asp Ser Ile Ala Leu Ile Ile Phe
385                 390                 395                 400

Ile Pro Ile Phe Glu Lys Phe Val Tyr Pro Phe Ile Arg Arg Tyr Thr
                405                 410                 415

Pro Leu Lys Pro Ile Thr Lys Ile Phe Phe Gly Phe Met Phe Gly Ser
                420                 425                 430
```

```
Phe Ala Met Thr Trp Ala Ala Val Leu Gln Ser Phe Val Tyr Lys Ala
            435                 440                 445

Gly Pro Trp Tyr Asn Glu Pro Leu Gly His Asn Thr Pro Asn His Val
    450                 455                 460

His Val Cys Trp Gln Ile Pro Ala Tyr Val Leu Ile Ser Phe Ser Glu
465                 470                 475                 480

Ile Phe Ala Ser Ile Thr Gly Leu Glu Tyr Ala Tyr Ser Lys Ala Pro
                485                 490                 495

Ala Ser Met Lys Ser Phe Ile Met Ser Ile Phe Leu Leu Thr Asn Ala
            500                 505                 510

Phe Gly Ser Ala Ile Gly Cys Ala Leu Ser Pro Val Thr Val Asp Pro
        515                 520                 525

Lys Phe Thr Trp Leu Phe Thr Gly Leu Ala Val Ala Cys Phe Ile Ser
    530                 535                 540

Gly Cys Leu Phe Trp Leu Cys Phe Arg Lys Tyr Asn Asp Thr Glu Glu
545                 550                 555                 560

Glu Met Asn Ala Met Asp Tyr Glu Glu Glu Asp Glu Phe Asp Leu Asn
                565                 570                 575

Pro Ile Ser Ala Pro Lys Ala Asn Asp Ile Glu Ile Leu Glu Pro Met
            580                 585                 590

Glu Ser Leu Arg Ser Thr Thr Lys Tyr
        595                 600

<210> SEQ ID NO 60
<211> LENGTH: 3037
<212> TYPE: DNA
<213> ORGANISM: Saccharomyces cerevisiae
<220> FEATURE:
<221> NAME/KEY: CDS
<222> LOCATION: (501)..(2537)

<400> SEQUENCE: 60
gctcttgaat ggcgacagcc tattgcccca gtgttccctc aacaaccttg gtagttggag      60
cgcaattagc gtatcctgta ccatactaat tctcttctgc ccaacgacgg ctgccattag     120
tcagcatggc gcgcacgtga ctacaactgt ggctggaaac cttttcgtcc tccccggttt     180
ttcagtgagc cgactctact acaatgcttt tcatttttc actcagaaaa acctgcaatt     240
tgccaaattg gccatgctct gtgcctccct gacaaagga catcttccct gtttataaac     300
ggcggcttac caaaagttga agcttgttct tgcctcttat gagtggagca atcgattata     360
ttgaatcgtt gtgctggagt agttggatct ttccacgtgg tctcgagtca cttgtagaag     420
ctgaaaattg agcagattta gtagggct acattgtagg gtggtttaga gtatcgaaaa     480
tatacatata gaagaataaa atg gga ctc tta gct ttg ggc acg cct ttg cag   533
                         Met Gly Leu Leu Ala Leu Gly Thr Pro Leu Gln
                          1               5                  10 tgg ttt gag tct agg acg tac aat gaa cac ata agg gat gaa ggt atc      581
Trp Phe Glu Ser Arg Thr Tyr Asn Glu His Ile Arg Asp Glu Gly Ile
             15                  20                  25 gag cag ttg ttg tat att ttc caa gct gct ggt aaa aga gac aat gac      629
Glu Gln Leu Leu Tyr Ile Phe Gln Ala Ala Gly Lys Arg Asp Asn Asp
         30                  35                  40 cct ctt ttt tgg gga gac gag ctt gag tac atg gtt gta gat ttt gat      677
Pro Leu Phe Trp Gly Asp Glu Leu Glu Tyr Met Val Val Asp Phe Asp
     45                  50                  55 gat aag gag aga aat tct atg ctc gac gtt tgc cat gac aag ata ctc      725
Asp Lys Glu Arg Asn Ser Met Leu Asp Val Cys His Asp Lys Ile Leu
```

```
                60                  65                  70                  75
act gag ctt aat atg gag gat tcg tcc ctt tgt gag gct aac gat gtg        773
Thr Glu Leu Asn Met Glu Asp Ser Ser Leu Cys Glu Ala Asn Asp Val
                    80                  85                  90 agt ttt cac cct gag tat ggc cgg tat atg tta gag gca aca cca gct        821
Ser Phe His Pro Glu Tyr Gly Arg Tyr Met Leu Glu Ala Thr Pro Ala
            95                 100                 105 tct cca tat ttg aat tac gtg ggt agt tac gtt gag gtt aac atg caa        869
Ser Pro Tyr Leu Asn Tyr Val Gly Ser Tyr Val Glu Val Asn Met Gln
        110                 115                 120 aaa aga cgt gcc att gca gaa tat aag cta tct gaa tat gcg aga caa        917
Lys Arg Arg Ala Ile Ala Glu Tyr Lys Leu Ser Glu Tyr Ala Arg Gln
    125                 130                 135 gat agt aaa aat aac ttg cat gtg ggc tcc agg tct gtc cct ttg acg        965
Asp Ser Lys Asn Asn Leu His Val Gly Ser Arg Ser Val Pro Leu Thr
140                 145                 150                 155 ctg act gtc ttc ccg agg atg gga tgc ccc gac ttt att aac att aag       1013
Leu Thr Val Phe Pro Arg Met Gly Cys Pro Asp Phe Ile Asn Ile Lys
                160                 165                 170 gat ccg tgg aat cat aaa aat gcc gct tcc agg tct ctg ttt tta ccc       1061
Asp Pro Trp Asn His Lys Asn Ala Ala Ser Arg Ser Leu Phe Leu Pro
            175                 180                 185 gat gaa gtc att aac aga cat gtc agg ttt cct aac ttg aca gca tcc       1109
Asp Glu Val Ile Asn Arg His Val Arg Phe Pro Asn Leu Thr Ala Ser
        190                 195                 200 atc agg acc agg cgt ggt gaa aaa gtt tgc atg aat gtt ccc atg tat       1157
Ile Arg Thr Arg Arg Gly Glu Lys Val Cys Met Asn Val Pro Met Tyr
    205                 210                 215 aaa gat ata gct act cca gaa acg gat gac tcc atc tac gat cga gat       1205
Lys Asp Ile Ala Thr Pro Glu Thr Asp Asp Ser Ile Tyr Asp Arg Asp
220                 225                 230                 235 tgg ttt tta cca gaa gac aaa gag gcg aaa ctg gct tcc aaa ccg ggt       1253
Trp Phe Leu Pro Glu Asp Lys Glu Ala Lys Leu Ala Ser Lys Pro Gly
                240                 245                 250 ttc att tat atg gat tcc atg ggt ttt ggc atg ggc tgt tcg tgc tta       1301
Phe Ile Tyr Met Asp Ser Met Gly Phe Gly Met Gly Cys Ser Cys Leu
            255                 260                 265 caa gtg acc ttt cag gca ccc aat atc aac aag gca cgt tac ctg tac       1349
Gln Val Thr Phe Gln Ala Pro Asn Ile Asn Lys Ala Arg Tyr Leu Tyr
        270                 275                 280 gat gca tta gtg aat ttt gca cct ata atg cta gcc ttc tct gcc gct       1397
Asp Ala Leu Val Asn Phe Ala Pro Ile Met Leu Ala Phe Ser Ala Ala
    285                 290                 295 gcg cct gct ttt aaa ggt tgg cta gcc gac caa gat gtt cgt tgg aat       1445
Ala Pro Ala Phe Lys Gly Trp Leu Ala Asp Gln Asp Val Arg Trp Asn
300                 305                 310                 315 gtg ata tct ggt gcg gtg gac gac cgt act ccg aag gaa aga ggt gtt       1493
Val Ile Ser Gly Ala Val Asp Asp Arg Thr Pro Lys Glu Arg Gly Val
                320                 325                 330 gcg cca tta cta ccc aaa tac aac aag aac gga ttt gga ggc att gcc       1541
Ala Pro Leu Leu Pro Lys Tyr Asn Lys Asn Gly Phe Gly Gly Ile Ala
            335                 340                 345 aaa gac gta caa gat aaa gtc ctt gaa ata cca aag tca aga tat agt       1589
Lys Asp Val Gln Asp Lys Val Leu Glu Ile Pro Lys Ser Arg Tyr Ser
        350                 355                 360 tcg gtt gat ctt ttc ttg ggt ggg tcg aaa ttt ttc aat agg act tat       1637
Ser Val Asp Leu Phe Leu Gly Gly Ser Lys Phe Phe Asn Arg Thr Tyr
    365                 370                 375 aac gac aca aat gta cct att aat gaa aaa gta tta gga cga cta cta       1685
```

```
Asn Asp Thr Asn Val Pro Ile Asn Glu Lys Val Leu Gly Arg Leu Leu
380                 385                 390                 395 gag aat gat aag gcg cca ctg gac tat gat ctt gct aaa cat ttt gcg    1733
Glu Asn Asp Lys Ala Pro Leu Asp Tyr Asp Leu Ala Lys His Phe Ala
                    400                 405                 410 cat ctc tac ata aga gat cca gta tct aca ttc gaa gaa ctg ttg aat    1781
His Leu Tyr Ile Arg Asp Pro Val Ser Thr Phe Glu Glu Leu Leu Asn
                415                 420                 425 cag gac aac aaa acg tct tca aat cac ttt gaa aac atc caa agt aca    1829
Gln Asp Asn Lys Thr Ser Ser Asn His Phe Glu Asn Ile Gln Ser Thr
            430                 435                 440 aat tgg cag aca tta cgt ttt aaa ccc ccc aca caa caa gca acc ccg    1877
Asn Trp Gln Thr Leu Arg Phe Lys Pro Pro Thr Gln Gln Ala Thr Pro
445                 450                 455 gac aaa aag gat tct cct ggt tgg aga gtg gaa ttc aga cca ttt gaa    1925
Asp Lys Lys Asp Ser Pro Gly Trp Arg Val Glu Phe Arg Pro Phe Glu
460                 465                 470                 475 gtg caa cta tta gat ttt gag aac gct gcg tat tcc gtg ctc ata tac    1973
Val Gln Leu Leu Asp Phe Glu Asn Ala Ala Tyr Ser Val Leu Ile Tyr
                    480                 485                 490 ttg att gtc gat agc att ttg acc ttt tcc gat aat att aac gca tat    2021
Leu Ile Val Asp Ser Ile Leu Thr Phe Ser Asp Asn Ile Asn Ala Tyr
                495                 500                 505 att cat atg tcc aaa gta tgg gaa aat atg aag ata gcc cat cac aga    2069
Ile His Met Ser Lys Val Trp Glu Asn Met Lys Ile Ala His His Arg
            510                 515                 520 gat gct atc cta ttt gaa aaa ttt cat tgg aaa aaa tca ttt cgc aac    2117
Asp Ala Ile Leu Phe Glu Lys Phe His Trp Lys Lys Ser Phe Arg Asn
525                 530                 535 gac acc gat gtg gaa act gaa gat tat tct ata agc gag att ttc cat    2165
Asp Thr Asp Val Glu Thr Glu Asp Tyr Ser Ile Ser Glu Ile Phe His
540                 545                 550                 555 aat cca gag aat ggt ata ttt cct caa ttt gtt acg cca atc cta tgc    2213
Asn Pro Glu Asn Gly Ile Phe Pro Gln Phe Val Thr Pro Ile Leu Cys
                    560                 565                 570 caa aaa ggg ttt gta acc aaa gat tgg aaa gaa tta aag cat tct tcc    2261
Gln Lys Gly Phe Val Thr Lys Asp Trp Lys Glu Leu Lys His Ser Ser
                575                 580                 585 aaa cac gag aga cta tac tat tat tta aag cta att tct gat aga gca    2309
Lys His Glu Arg Leu Tyr Tyr Tyr Leu Lys Leu Ile Ser Asp Arg Ala
            590                 595                 600 agc ggt gaa ttg cca aca aca gca aaa ttc ttt aga aat ttt gta cta    2357
Ser Gly Glu Leu Pro Thr Thr Ala Lys Phe Phe Arg Asn Phe Val Leu
605                 610                 615 caa cat cca gat tac aaa cat gat tca aaa att tca aag tcg atc aat    2405
Gln His Pro Asp Tyr Lys His Asp Ser Lys Ile Ser Lys Ser Ile Asn
620                 625                 630                 635 tat gat ttg ctt tct acg tgt gat aga ctt acc cat tta gac gat tca    2453
Tyr Asp Leu Leu Ser Thr Cys Asp Arg Leu Thr His Leu Asp Asp Ser
                    640                 645                 650 aaa ggt gaa ttg aca tcc ttt tta gga gct gaa att gca gaa tat gta    2501
Lys Gly Glu Leu Thr Ser Phe Leu Gly Ala Glu Ile Ala Glu Tyr Val
                655                 660                 665 aaa aaa aat aag cct tca ata gaa agc aaa tgt taa actccttta          2547
Lys Lys Asn Lys Pro Ser Ile Glu Ser Lys Cys
            670                 675 cttcggttgt gaaagaaagt tgacattatc gatttgggtg acacggtgat gaaaaagca   2607 acgaccagta ttatacctct ttttttatt attcagttta tattttgca agtgatctta    2667
```

-continued

```
agcatttcta cacaaactta tgccaacgtg accatttatt attttatata gcaaaaaaaa    2727
atgaggggcc ttgcagaaca attgttgcga gtttctaata acaagcacgt agaatattgg    2787
ccatttaatt tttctcttca atttatagaa tggttgtgtt agtgacaaaa agaatattct    2847
tccccgccag gactcgaacc tggaatctcc tggttcgtag ccagacgccg tgaccattgg    2907
gccacgagga acaagaatat aaagatctct gagggcaagg tatgcctatg tcgcaataaa    2967
atgtttgttc ctgcgcaaaa gtaaagttct attaatatac aactacacag ttatcggttc    3027
acactattcg                                                           3037
```

<210> SEQ ID NO 61
<211> LENGTH: 678
<212> TYPE: PRT
<213> ORGANISM: Saccharomyces cerevisiae

<400> SEQUENCE: 61

```
Met Gly Leu Leu Ala Leu Gly Thr Pro Leu Gln Trp Phe Glu Ser Arg
 1               5                  10                  15

Thr Tyr Asn Glu His Ile Arg Asp Glu Gly Ile Glu Gln Leu Leu Tyr
                20                  25                  30

Ile Phe Gln Ala Ala Gly Lys Arg Asp Asn Asp Pro Leu Phe Trp Gly
            35                  40                  45

Asp Glu Leu Glu Tyr Met Val Val Asp Phe Asp Lys Glu Arg Asn
     50                  55                  60

Ser Met Leu Asp Val Cys His Asp Lys Ile Leu Thr Glu Leu Asn Met
 65                  70                  75                  80

Glu Asp Ser Ser Leu Cys Glu Ala Asn Asp Val Ser Phe His Pro Glu
                 85                  90                  95

Tyr Gly Arg Tyr Met Leu Glu Ala Thr Pro Ala Ser Pro Tyr Leu Asn
            100                 105                 110

Tyr Val Gly Ser Tyr Val Glu Val Asn Met Gln Lys Arg Arg Ala Ile
        115                 120                 125

Ala Glu Tyr Lys Leu Ser Glu Tyr Ala Arg Gln Asp Ser Lys Asn Asn
    130                 135                 140

Leu His Val Gly Ser Arg Ser Val Pro Leu Thr Leu Thr Val Phe Pro
145                 150                 155                 160

Arg Met Gly Cys Pro Asp Phe Ile Asn Ile Lys Asp Pro Trp Asn His
                165                 170                 175

Lys Asn Ala Ala Ser Arg Ser Leu Phe Leu Pro Asp Glu Val Ile Asn
            180                 185                 190

Arg His Val Arg Phe Pro Asn Leu Thr Ala Ser Ile Arg Thr Arg Arg
        195                 200                 205

Gly Glu Lys Val Cys Met Asn Val Pro Met Tyr Lys Asp Ile Ala Thr
    210                 215                 220

Pro Glu Thr Asp Asp Ser Ile Tyr Asp Arg Asp Trp Phe Leu Pro Glu
225                 230                 235                 240

Asp Lys Glu Ala Lys Leu Ala Ser Lys Pro Gly Phe Ile Tyr Met Asp
                245                 250                 255

Ser Met Gly Phe Gly Met Gly Cys Ser Cys Leu Gln Val Thr Phe Gln
            260                 265                 270

Ala Pro Asn Ile Asn Lys Ala Arg Tyr Leu Tyr Asp Ala Leu Val Asn
        275                 280                 285

Phe Ala Pro Ile Met Leu Ala Phe Ser Ala Ala Pro Ala Phe Lys
    290                 295                 300
```

```
Gly Trp Leu Ala Asp Gln Asp Val Arg Trp Asn Val Ile Ser Gly Ala
305                 310                 315                 320

Val Asp Asp Arg Thr Pro Lys Glu Arg Gly Val Ala Pro Leu Leu Pro
                325                 330                 335

Lys Tyr Asn Lys Asn Gly Phe Gly Gly Ile Ala Lys Asp Val Gln Asp
            340                 345                 350

Lys Val Leu Glu Ile Pro Lys Ser Arg Tyr Ser Ser Val Asp Leu Phe
        355                 360                 365

Leu Gly Gly Ser Lys Phe Phe Asn Arg Thr Tyr Asn Asp Thr Asn Val
    370                 375                 380

Pro Ile Asn Glu Lys Val Leu Gly Arg Leu Leu Glu Asn Asp Lys Ala
385                 390                 395                 400

Pro Leu Asp Tyr Asp Leu Ala Lys His Phe Ala His Leu Tyr Ile Arg
                405                 410                 415

Asp Pro Val Ser Thr Phe Glu Glu Leu Leu Asn Gln Asp Asn Lys Thr
            420                 425                 430

Ser Ser Asn His Phe Glu Asn Ile Gln Ser Thr Asn Trp Gln Thr Leu
        435                 440                 445

Arg Phe Lys Pro Pro Thr Gln Gln Ala Thr Pro Asp Lys Lys Asp Ser
    450                 455                 460

Pro Gly Trp Arg Val Glu Phe Arg Pro Phe Glu Val Gln Leu Leu Asp
465                 470                 475                 480

Phe Glu Asn Ala Ala Tyr Ser Val Leu Ile Tyr Leu Ile Val Asp Ser
                485                 490                 495

Ile Leu Thr Phe Ser Asp Asn Ile Asn Ala Tyr Ile His Met Ser Lys
            500                 505                 510

Val Trp Glu Asn Met Lys Ile Ala His His Arg Asp Ala Ile Leu Phe
        515                 520                 525

Glu Lys Phe His Trp Lys Lys Ser Phe Arg Asn Asp Thr Asp Val Glu
    530                 535                 540

Thr Glu Asp Tyr Ser Ile Ser Glu Ile Phe His Asn Pro Glu Asn Gly
545                 550                 555                 560

Ile Phe Pro Gln Phe Val Thr Pro Ile Leu Cys Gln Lys Gly Phe Val
                565                 570                 575

Thr Lys Asp Trp Lys Glu Leu Lys His Ser Ser Lys His Glu Arg Leu
            580                 585                 590

Tyr Tyr Tyr Leu Lys Leu Ile Ser Asp Arg Ala Ser Gly Glu Leu Pro
        595                 600                 605

Thr Thr Ala Lys Phe Phe Arg Asn Phe Val Leu Gln His Pro Asp Tyr
    610                 615                 620

Lys His Asp Ser Lys Ile Ser Lys Ser Ile Asn Tyr Asp Leu Leu Ser
625                 630                 635                 640

Thr Cys Asp Arg Leu Thr His Leu Asp Asp Ser Lys Gly Glu Leu Thr
                645                 650                 655

Ser Phe Leu Gly Ala Glu Ile Ala Glu Tyr Val Lys Lys Asn Lys Pro
            660                 665                 670

Ser Ile Glu Ser Lys Cys
        675
```

YEAST EXTRACT CONTAINING γ-GLU-X OR γ-GLU-X-GLY AND A METHOD FOR PRODUCING THE SAME

BACKGROUND OF THE INVENTION

1. Technical Field

The present invention relates to a yeast extract containing γ-Glu-X-Gly or γ-Glu-X and a method for producing the same. The yeast extract of the present invention is useful in the field of foodstuffs such as seasonings and health foods.

2. Background Art

Yeast extracts have a function of imparting atsumi (thickness), umami, etc. to foodstuffs, and have been widely used as seasonings in the field of foodstuffs. Especially, glutathione (henceforth also referred to as "GSH"), which is a tripeptide consisting of glutamic acid, cysteine and glycine, is known to impart kokumi to foodstuffs (Ueda et al., Agric. Biol. Chem., 54, 163-169 (1990), Ueda et al., Biosci. Biotechnolo. Biochem., 61, 1977-1980 (1997)), and seasonings containing GSH have been developed.

Meanwhile, although the calcium sensing receptor (CaSR), which is a G-protein classified into the class C, has been reported to respond to GSH (Wang et al., Journal of Biological Chemistry, 281, 8864-8870 (2006)), the physiological significance thereof has not been clarified. Moreover, this CaSR is present also in the lingual cells, and it was considered to show a certain taste response (Gabriel et al., Biochemical and Biophysical Research Communications, 378, 414-418 (2009)). Then, it has recently been clarified that this CaSR participates in recognition of kokumi in humans (Ohsu et al., Journal of Biological Chemistry, 285, 1016-1022 (2010)). This reference reported that not only GSH has been recognized as a kokumi substance, but also several γ-glutamyl compounds similarly respond to CaSR. Furthermore, it has been reported that peptides represented by the general formula γ-Glu-X or γ-Glu-X-Gly (X can represent an amino acid or amino acid derivative other than Cys), for example, γ-Glu-Met, γ-Glu-Thr, γ-Glu-Val-Gly, etc. have a kokumi-imparting effect (WO2007/055393). Moreover, the group of esters including S- or O-carboxyalkylated γ-glutamyl or β-asparagyl peptides etc., are also reported as kokumi substances (WO2007/042288). Although these peptides impart kokumi to foodstuffs like GSH, they do not have a reduced SH group unlike GSH. It is known that a substance having the reduced SH group such as GSH is generally unstable, and titer thereof is reduced with formation of disulfide bond (WO2007/042288). However, γ-Glu-X, γ-Glu-X-Gly etc. are considered useful from the viewpoint that the kokumi-imparting peptides not having the reduced SH group are stable.

As for foodstuffs containing a γ-Glu dipeptide, it has been reported that various γ-Glu dipeptides were detected in Gouda cheese ripened over a long period of time, even as long as about 44 weeks (Toelstede, S and Hofmann, T, J. Agric. Food. Chem., 2009). This reference reported that various γ-Glu dipeptides such as γ-Glu-Ala, γ-Glu-Glu and γ-Glu-Gln were detected in a total amount of 3590 μmol/kg of dry materials at most. This value corresponds to 0.088% in terms of weight percentage based on the solid content.

However, a yeast extract containing γ-Glu-X and γ-Glu-X-Gly in an amount enabling impartation of kokumi has not been previously reported.

Furthermore, it is known that the synthesis and decomposition of glutathione, which is one of the γ-glutamyl compounds, is catalyzed by a plurality of enzymes which make up the γ-glutamyl cycle. In particular, γ-glutamyl transpeptidase is known to transfer the glutamate of GSH at the γ-position to another compound having an amino group, resulting in decomposition of GSH to cysteinylglycine (Protein Nucleic acid Enzyme, 1988-7, VOL. 33, NO. 9, ISSN 003909450, Special Issue "Epoch of glutathione research", pp. 1432-1433). It is considered that, if the compound having an amino group in this rearrangement reaction is an amino acid, a dipeptide of γ-Glu-X can be generated as a by-product. However, research into making a microorganism effectively produce this by-product has not been positively performed to date, partially because it is a by-product.

Findings about the dipeptide γ-Glu-X that have been reported include an analysis of the fermentation broth of *Micrococcus glutamicus* (Ronald et al., Journal of Biological Chemistry, 240, p 2508-2511 (1965)). This reference reported that the fermentation broth was loaded onto various columns to separate peptides etc., and to isolate γ-Glu-Glu, γ-Glu-Val, and γ-Glu-Leu. However, these were found as a result of separation with various columns, and the amounts of these peptides contained in the broth were not determined.

Furthermore, an enzyme responsible for GSH biosynthesis was newly isolated from *Streptococcus agalactiae* and *Clostridium acetobutylicum*, and the substrate specificity thereof was analyzed (Kino et al., JBB research communications, 352, pp. 351-359 (2007)). GSH is usually biosynthesized by two different enzymes called γ-glutamylcysteine synthetase, which combines Glu and Cys to generate γ-Glu-Cys, and glutathione synthetase, which combines the produced γ-Glu-Cys and Gly to generate GSH. However, the aforementioned two kinds of microorganisms have a unique enzyme which is essentially a fusion of γ-glutamylcysteine synthetase and glutathione synthetase. It was reported that, according to an in vitro analysis, the substrate recognition of this enzyme was slightly ambiguous, i.e., it also recognized amino acids other than Cys, and as a result, it could generate γ-Glu-X and γ-Glu-X-Gly. However, these are nevertheless in vitro results, and it was not described whether or not those microorganisms that produced marked amounts of peptides such as γ-Glu-X and γ-Glu-X-Gly, also contain many compounds having an amino group besides the target X.

Yeast extracts are seasonings which have been widely used in the field of foodstuffs, and are highly accepted by consumers. Therefore, a yeast extract can be used as a carrier of γ-Glu-X-Gly or γ-Glu-X. Yeast strains containing minerals have been studied for this use. It is known that if a metal is added to a medium, yeasts take up the metal into the cells (B. Volesky, H. A., Appl. Microbiol. Biotechnol., 42; 797-806 (1995)). In particular, if trace elements such as zinc, iron, copper, manganese, selenium, molybdenum and chromium are added to the medium, yeasts can be used to supply such trace elements via enrichment in foodstuffs (Japanese Patent Laid-open (Kokai) No. 2004-298014). As a result, methods for producing mineral-containing yeast have been developed (Japanese Patent Laid-open No. 54-157890, Japanese Patent Laid-open No. 60-75279, Japanese Patent Publication (Kokoku) No. 6-16702).

Furthermore, mineral-containing yeast also have an advantage concerning taste. For example, yeast containing a high amount of magnesium are described in Japanese Patent Laid-open No. 8-332081. This reference describes that although magnesium-enriched foodstuffs containing inorganic magnesium salt were also marketed, a strong bitterness and astringency was noted due to the mineral salt. As a result, it was quite more difficult to routinely eat the magnesium-enriched foodstuffs containing inorganic magnesium salt as compared to foodstuffs containing naturally occurring magnesium. Japanese Patent Laid-open No. 8-332081 also discloses a technique of producing a natural material by making yeast take up magnesium. As for nutritional merit, the technique disclosed in Japanese Patent Laid-open No. 2008-99578 can be exemplified. According to this reference, although zinc contributes to improving taste and generative function, etc., the reference overlooks that zinc is often not taken in sufficient amounts. If zinc is added during the yeast cultivation process, yeast takes up zinc into cells, but water-soluble zinc binds with a protein or an amino acid, and accumulates as amorphous zinc at a high concentration. The amorphous zinc is more efficiently absorbed into the body, as compared to crystalline zinc. As a result, improved absorption can be obtained by incorporating zinc into yeast, as compared to simply taking zinc as it is.

As described above, there are various advantages to making yeast take up a target substance and adding either the yeast or a yeast extract to foodstuffs, as compared to simply adding the target substance to foodstuffs. However, unlike minerals, which are essential nutrients, the ability of yeast to take up an amino acid or a peptide is delicately controlled, and it simply applying the technique for incorporating minerals into yeast to the techniques for uptake of amino acid or peptides was considered to be difficult.

There has been much research concerning the generation of GSH or γ-Glu-Cys using yeast Examples of such research include the report that the GSH content was improved by mutagenizing a *Saccharomyces* yeast and selecting a strain having improved zinc resistance (Japanese Patent Laid-open No. 02-295480), the report that suppression of the MET25 gene expression was derepressed by making a cell contain a mutant MET30 gene and thereby increase intracellular γ-Glu-Cys content (Japanese Patent Application No. 2002-282743), and so forth. Moreover, the latest scientific findings include uptake of GSH by Hgt1p. Although GSH and the dimer thereof, GSSG, were taken into cells by Hgt1p, uptake of GSH by Hgt1p was not affected even in the presence of excessive amounts of amino acids, various dipeptides, and tripeptides. Therefore, it is considered that Hgt1p is not a nonspecific transporter as once thought, but a transporter specific to GSH (Bourbouloux et al., Journal of Biological Chemistry, 275, pp. 13259-13265 (2000)). Furthermore, a search for the active site of Hgt1p has also been performed (Kaur et al., FEMS Yeast Res., 9, 849-866 (2009)).

As described above, although many findings about GSH and the precursor thereof, γ-Glu-Cys, have been reported, there have been no reports about yeast cells containing such a substance as γ-Glu-X and γ-Glu-X-Gly, and a method for producing an extract prepared from the cells.

SUMMARY OF THE INVENTION

Aspects of the present invention include providing a yeast extract containing γ-Glu-X or γ-Glu-X-Gly, and providing a method for producing the yeast.

The above aspects were achieved by finding that a yeast took up γ-Glu-X and γ-Glu-X-Gly (X represents an amino acid or an amino acid derivative other than Cys, the same shall apply in the following descriptions) into cells, and a yeast extract containing γ-Glu-X or γ-Glu-X-Gly could be produced by preparing the yeast extract from a yeast cultured in a medium containing γ-Glu-X or γ-Glu-X-Gly. Moreover, it was found that if yeast was cultured in a medium containing γ-Glu-X or X-Gly, these compounds were taken up into the cells, and γ-Glu-X-Gly could be generated via an intracellular enzymatic reaction. Furthermore, it was also found that a yeast extract containing γ-Glu-X or γ-Glu-X-Gly could be produced by allowing γ-glutamyl transferase to act on a yeast extract raw material to which an amino acid or a peptide selected from X and X-Gly was added.

It is an aspect of the present invention to provide a yeast extract containing a peptide selected from the group consisting of γ-Glu-X and γ-Glu-X-Gly in a total amount of 0.005% or more based on dry weight of the yeast extract, wherein X represents an amino acid or an amino acid derivative other than Cys and derivatives thereof).

It is a further aspect of the present invention to provide the yeast extract as described above, which contains the peptide in a total amount of 0.02% or more.

It is a further aspect of the present invention to provide the yeast extract as described above, wherein X is Val.

It is a further aspect of the present invention to provide the yeast extract as described above, wherein X is nVal.

It is a further aspect of the present invention to provide the yeast extract as described above, wherein the yeast is *Saccharomyces cerevisiae*.

It is a further aspect of the present invention to provide a method for producing a yeast extract containing a peptide selected from the group consisting of γ-Glu-X and γ-Glu-X-Gly, which comprises culturing a yeast in a medium containing a peptide selected from the group consisting of γ-Glu-X, γ-Glu-X-Gly and X-Gly, and preparing a yeast extract from the obtained cells, wherein X represents an amino acid or an amino acid derivative other than Cys and derivatives thereof.

It is a further aspect of the present invention to provide the method as described above, wherein the medium contains 0.1 ppm or more of the peptide, and the yeast extract contains the peptide selected from the group consisting of γ-Glu-X and γ-Glu-X-Gly in a total amount of 0.005% or more based on dry weight of the yeast extract.

It is a further aspect of the present invention to provide the method as described above, wherein X is Val.

It is a further aspect of the present invention to provide the method as described above, wherein the yeast has been modified so that uptake of the peptide into cells is improved.

It is a further aspect of the present invention to provide the method as described above, wherein the activity of Hgt1p of the yeast has been enhanced.

It is a further aspect of the present invention to provide the method as described above, wherein the activity of Ptr2p of the yeast has been enhanced.

It is a further aspect of the present invention to provide the method as described above, wherein the activity of glutathione synthetase of the yeast has been enhanced.

It is a further aspect of the present invention to provide a method for producing a yeast extract containing γ-Glu-nVal, which comprises culturing a yeast in a medium containing nVal.

It is a further aspect of the present invention to provide the method as described above, wherein the activity of γ-glutamylcysteine synthetase of yeast has been enhanced.

It is a further aspect of the present invention to provide the method as described above, wherein the yeast is *Saccharomyces cerevisiae*.

It is a further aspect of the present invention to provide a method for producing a yeast extract containing a peptide selected from the group consisting of γ-Glu-X and γ-Glu-X-Gly, which comprises allowing a γ-glutamyl transferase to act on a yeast extract raw material to which an amino acid or a peptide selected from the group consisting of X and X-Gly is added, wherein X represents an amino acid or an amino acid derivative other than Cys and derivatives thereof.

It is a further aspect of the present invention to provide the method as described above, wherein the amino acid or peptide is added in a total amount of 1% or more based on dry weight of the yeast extract raw material, and the yeast extract contains a peptide selected from the group consisting of γ-Glu-X and γ-Glu-X-Gly in a total amount of 0.005% or more based on dry weight of the yeast extract.

It is a further aspect of the present invention to provide the method as described above, wherein X is Val.

It is a further aspect of the present invention to provide the method as described above, wherein X is nVal.

It is a further aspect of the present invention to provide the method as described above, wherein the yeast is *Saccharomyces cerevisiae*.

According to the present invention, a yeast extract containing γ-Glu-X, γ-Glu-X-Gly, or these both can be produced. A yeast extract containing these peptides is excellent in kokumi.

Moreover, the yeast extract containing γ-Glu-X is also useful as a raw material for producing a yeast extract containing γ-Glu-X-Gly.

BRIEF DESCRIPTION OF THE DRAWINGS

FIG. 1 shows HPLC-MS chromatograms of γ-Glu-Val-Gly, γ-Glu-Val and Val-Gly standard samples.

CDS=coding sequence of target gene
up-CDS=region upstream target gene.

Horizontally stroked boxes designate a 40-base pairs overlapping region, black box designates a 40-base fragment for homologous recombination with 5'-region of target gene.

Figure 10:
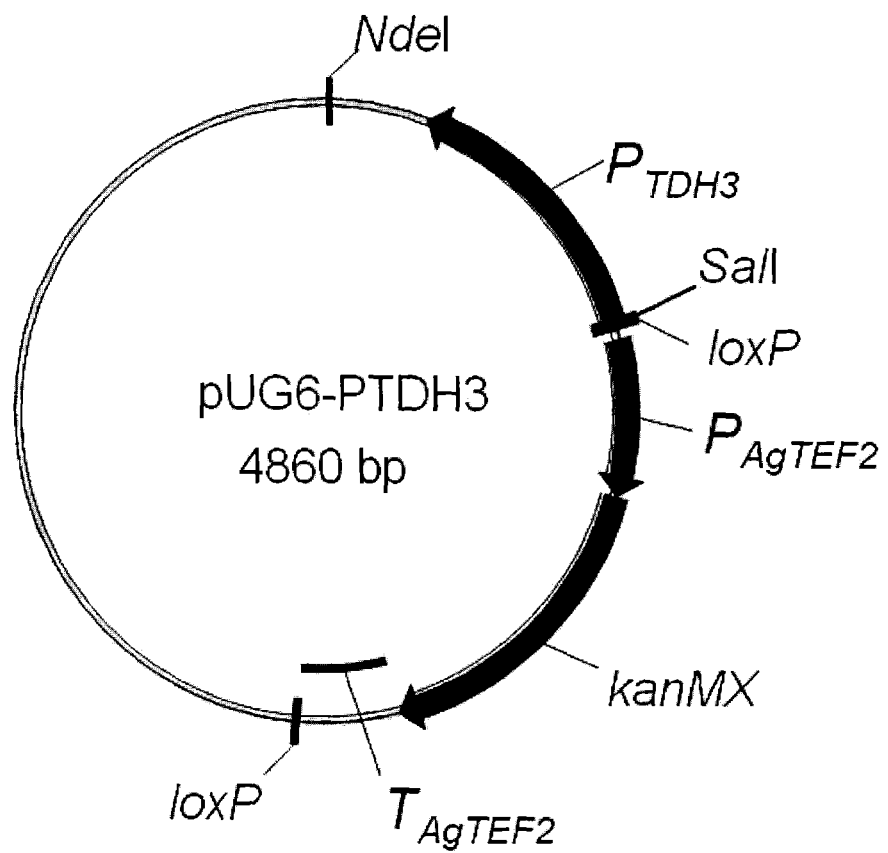

FIG. 10 shows the map of pUG6-PTDH3.

Figure 11:
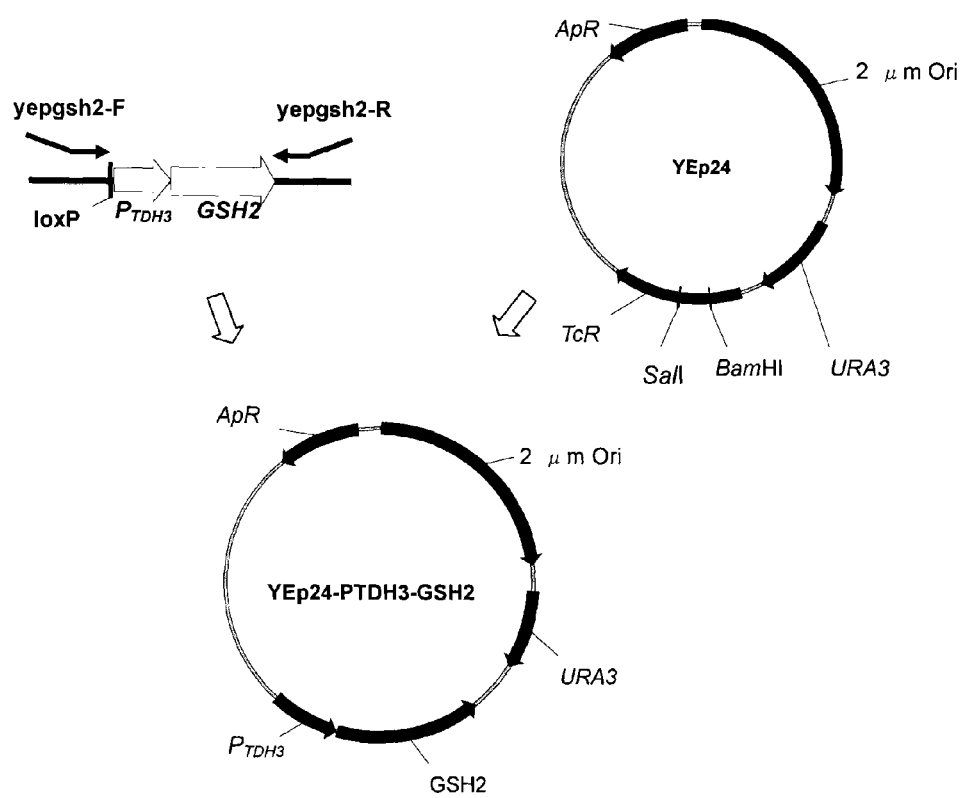

FIG. 11 shows cloning of the $P_{TDH3}$-GSH2 cassette into multicopy yeast vector.

DETAILED DESCRIPTION OF THE PREFERRED EMBODIMENTS

The yeast extract in accordance with the presently described subject matter contains a peptide such as γ-Glu-X and γ-Glu-X-Gly in a total amount of 0.005% or more based on dry weight of the yeast extract, wherein X can represent an amino acid or an amino acid derivative other than Cys and derivatives thereof. The yeast extract can contain the peptide in a total amount of 0.005% or more, 0.02% or more, 0.1% or more, or 0.5% or more, based on dry weight of the yeast extract.

The yeast used as the raw material of the yeast extract is the same as the yeast used for the method described later.

Glu and Gly in the peptide represent glutamic acid and glycine, respectively. The symbol "-" represents a peptide bond. "γ" of γ-Glu means that another amino acid binds via the carboxy group of the glutamic acid at the γ-position.

"X" can represent any of 19 kinds of amino acid among the natural amino acids or a derivative thereof, except for Cys and derivatives thereof. Cys represents cysteine, and examples of the derivatives thereof include α-aminobutyric acid, β-aminobutyric acid, and so forth. The aforementioned amino acids except for Cys and derivatives thereof include neutral amino acids such as glycine (Gly), alanine (Ala), valine (Val), leucine (Leu), isoleucine (Ile), serine (Ser), threonine (Thr), methionine (Met), asparagine (Asn), glutamine (Gln) and proline (Pro), acidic amino acids such as aspartic acid (Asp) and glutamic acid (Glu), basic amino acids such as lysine (Lys), arginine (Arg) and histidine (His), and aromatic amino acids such as phenylalanine (Phe), tyrosine (Tyr) and tryptophan (Trp). In particular, when X is a hydrophobic amino acid, the kokumi effect of the peptide is high, and such a peptide is a particular example. Examples of such hydrophobic amino acids include Val, Ala, Leu, Phe, and so forth.

Examples of the derivatives of amino acid include, for example, norvaline (nVal), norleucine (nLeu), tert-leucine (tLeu), hydroxyproline (Hyp), and so forth.

Among the aforementioned peptides, particular examples are γ-Glu-Val-Gly, γ-Glu-Val, γ-Glu-nVal-Gly, γ-Glu-nVal, and Val-Gly.

In addition, the aforementioned amino acids and amino acid derivatives are all L-isomers.

The form of the yeast extract is not particularly limited, and it may be in the form of powder or solution. The yeast extract can have the same uses as that of conventional yeast extracts, for example, seasonings, food additives, health foods, and so forth. The yeast extract is excellent in its kokumi-imparting effect. Kokumi means a taste that cannot be expressed with the five basic tastes, and means a taste that enhances not only the basic tastes but also marginal tastes of the basic tastes, such as thickness, growth (mouthfulness), continuity, and harmony. Since the kokumi-imparting effect is more strongly exerted in the presence of umami or salty taste, an umami substance such as sodium L-glutamate and taste nucleotides, and/or a salty substance such as sodium chloride may be added to the yeast extract. Moreover, an umami substance and/or a salty substance may be added to seasonings, food additives or health foods together with the yeast extract in accordance with the presently described subject matter.

As shown in the examples section, yeast extracts containing γ-Glu-Val-Gly, especially a solution containing a yeast extract, produced by the method described herein, showed a higher kokumi-enhancing effect as compared to a γ-Glu-Val-Gly solution having the same concentration of γ-Glu-Val-Gly as that of the solution. This indicates the usefulness of the yeast extract.

The yeast extract in accordance with the presently described subject mattercan be produced by, for example, the methods of the present invention described herein.

The first method in accordance with the presently described subject matteris a method for producing a yeast extract containing a peptide selected from γ-Glu-X-Gly and γ-Glu-X, which includes the steps of culturing a yeast in a medium containing a peptide selected from γ-Glu-X-Gly, γ-Glu-X and X-Gly, and preparing a yeast extract from the obtained cells, wherein X represents an amino acid or an amino acid derivative other than Cys and derivatives thereof.

The yeast is not particularly limited, so long as the chosen yeast can take up γ-Glu-X, γ-Glu-X-Gly or X-Gly into the cells thereof. Examples include yeasts belonging to the genus *Saccharomyces* such as *Saccharomyces cerevisiae*, those belonging to the genus *Candida* such as *Candida utilis*, those belonging to the genus *Pichia* such as *Pichia pastoris*, and those belonging to the genus *Schizosaccharomyces* such as *Schizosaccharomyces pombe*. Among these, *Saccharomyces cerevisiae* and *Candida utilis* are particular examples, and are frequently used for production of yeast extracts. The yeast may be a monoploid, or may have diploidy or a further higher polyploidy.

The yeast may be any wild-type strain, or various mutant strains, so long as the chosen yeast can intracellularly take up γ-Glu-X, γ-Glu-X-Gly or X-Gly and accumulate γ-Glu-X and/or γ-Glu-X-Gly in the cells. Examples of mutant strains include a strain with enhanced activities or activity of γ-glutamylcysteine synthetase (GSH1) and/or glutathione synthetase (GSH2). The yeast may also be modified so that the uptake of γ-Glu-X, γ-Glu-X-Gly or X-Gly into the cells is improved. The uptake of γ-Glu-X, γ-Glu-X-Gly or X-Gly can be improved by enhancing an activity of a protein which participates in the uptake of these peptides. Although Hgt1p had been reported to be a transporter specific to GSH, it is shown that, by enhancing the activity of Hgt1p, the uptake of γ-Glu-Val-Gly or γ-Glu-nVal-Gly can be improved (see the examples section). Therefore, it is possible that the uptake of not only γ-Glu-Val-Gly, but also other γ-Glu-X-Gly peptides into the cells can be improved by enhancing the Hgt1p activity. Also, Ptr2p had been reported to be an oligopeptide transporter. It is shown that, by enhancing the activity of Ptr2p, the uptake of Val-Gly seemed to be enhanced (see the examples section). Therefore, it is possible that the uptake of not only Val-Gly, but also other X-Gly peptides into the cells can be improved by enhancing Ptr2p activity. The nucleotide sequence of the gene coding for Ptr2p of *Saccharomyces cerevisiae* is shown in SEQ ID NO: 58. The amino acid sequence encoded by this nucleotide sequence is shown in SEQ ID NO: 59. The methods for enhancing the activity of the aforementioned enzyme or protein include enhancing expression thereof by replacing the promoter of the gene coding for the enzyme or protein on the chromosome with a stronger promoter, enhancing expression thereof by inserting the target gene into the chromosome to introduce two or more copies thereof, and enhancing expression thereof by incorporating a plasmid containing the target gene into the yeast, or the like.

As the promoter, a highly active conventional promoter may be obtained by using various reporter genes, or a known high expression promoter such as PGK1, PDC1, TDH3, TEF1 and HXT7 may be used. Alternatively, a plasmid having the replication origin of CEN4, or a multi-copy plasmid having the replication origin of 2 μm DNA may be used. Furthermore, a transposon may be used in order to introduce a target gene into an arbitrary region of the chromosome, or the target gene may be introduced by using rDNA sequences as a target, which is present in a copy number of 150 in the cell.

Enhancement of the activity of γ-glutamylcysteine synthetase is disclosed in, for example, U.S. Pat. No. 7,553,638; Otake Y. et al., Bioscience and Industry, volume 50, No. 10, pp. 989-994, 1992, and so forth. Although disruption of the glutathione synthetase gene is disclosed in U.S. Pat. No. 7,553,638, the glutathione synthetase activity can be enhanced in the same manner as that for enhancement of the activity of γ-glutamylcysteine synthetase. The activity of Hgt1p can also be enhanced in a similar manner.

The nucleotide sequences of the genes coding for Gsh1p and Gsh2p of *Saccharomyces cerevisiae* are disclosed in *Saccharomyces* Genome Database (http://www.yeastgenome.org/). The nucleotide sequences of the genes coding for Gsh1p and Gsh2p of *Candida utilis* are disclosed in U.S. Pat. No. 7,553,638. The nucleotide sequence of the gene coding for Gsh1p of *Saccharomyces cerevisiae* is shown in SEQ ID NO: 60. The amino acid sequence encoded by this nucleotide sequence is shown in SEQ ID NO: 61. The nucleotide sequence of the gene coding for Gsh2p of *Saccharomyces cerevisiae* is shown in SEQ ID NO: 19. The amino acid sequence encoded by this nucleotide sequence is shown in SEQ ID NO: 20.

The gene coding for Hgt1p can be obtained from *Saccharomyces* Genome Database (http://www.yeastgenome.org/). Synonyms of Hgt1p include Gsh11p, Opt1p or the like. The sequence disclosed as GSH11 of *Saccharomyces cerevisiae* is shown in SEQ ID NO: 21. Moreover, the amino acid sequence encoded by this nucleotide sequence is shown in SEQ ID NO: 22.

The method for producing the yeast extract is explained below.

First, a yeast is cultured in a medium containing the peptide. The medium is not particularly limited, so long as a medium in which the yeast can proliferate is chosen, and is not limited to the SD medium described in the examples. A medium usually used for industrial purposes can be used.

When the yeast is cultured, γ-Glu-X, γ-Glu-X-Gly or X-Gly is added to the aforementioned medium. One type of these peptides may be added, or a arbitrary mixture of two or more kinds of these peptides may be added. These peptides may be present in the medium from the start of the culture, or may be added to the medium at an arbitrary time during the culture. When the peptides are added to the medium during the culture, they can be added at 0 to 50 hours before the end of the culture (0 hour means that the culture is terminated immediately after the addition), 0.1 to 24 hours before the end of the culture, or 0.5 to 6 hours before the end of the culture. Furthermore, when the peptides are added during the culture, they may be continuously added.

Prior to the culture in the medium containing the peptides, a preculture may be performed. The medium used for the preculture may or may not contain the peptides.

The peptides are added to the medium usually in an amount of 0.1 ppm or more, 0.5 ppm or more, 1 ppm or more, 10 ppm or more, or 50 ppm or more, in terms of the final concentration in the culture broth at the time of the addition. Although the upper limit of the amount of the peptides is not particularly limited, it can be exemplified as less than 100,000 or 50,000 ppm from an aspect of production cost, it is usually 10,000 ppm or less, 1,000 ppm or less, or 500 ppm or less.

The peptide amount to be added to the medium is usually not less than 0.1 ppm, 0.5 ppm, 1 ppm, 10 ppm, or 50 ppm in terms of the final concentration in the culture broth at the time of the addition. The upper limit of the peptide amount is not specifically limited. However, the upper limit of the peptide amount can be set, for example, to be not more than 100,000 ppm or not more than 50,000 ppm in view of the production cost. The upper limit of the peptide amount is usually not more than 10,000 ppm, 1,000 ppm, or 500 ppm.

As the culture conditions, the same conditions as those used for usual production of yeast extracts can be used, and they may be suitably changed according to the chosen yeast. Arbitrary methods such as batch culture, fed-batch culture, and continuous culture may be used. When the yeast is *Saccharomyces cerevisiae*, it is preferably aerobically cultured by shaking or the like at 25 to 35° C., 27 to 33° C., or 28 to 32° C.

If the yeast is cultured as described above, γ-Glu-X, γ-Glu-X-Gly, or both can accumulate in the cells of the yeast. When γ-Glu-X or X-Gly is added to the medium, these peptides accumulate in the cells, and in addition, γ-Glu-X-Gly also accumulates. It is estimated that this is because γ-Glu-X-Gly is produced from γ-Glu-X and X-Gly, which have been taken up into the cells by the action of intracellular γ-glutamyl transferase. As shown in the examples section, the amount of γ-Glu-Val and γ-Glu-Val-Gly in the yeast did not correlate with the amount of GSH in the cells, and therefore it is considered that yeast extracts produced by the conventional methods do not contain γ-Glu-X or γ-Glu-X-Gly at a high concentration, even if they are produced from a yeast containing GSH at a high concentration.

The yeast extract can be prepared from the yeast in the same manner as that used for conventional production of yeast extracts. The yeast extract may be obtained by subjecting the yeast cells to hot water extraction and processing the extract, or by digesting the yeast cells and processing the digestion product. Furthermore, the obtained yeast extract may be concentrated, or may be dried and thereby made into powdered form, if needed.

In such a manner as described above, a yeast extract in which the amount of γ-Glu-X, γ-Glu-X-Gly or both are increased is obtained. The yeast extract can contain γ-Glu-X, γ-Glu-X-Gly, or both in a total amount of 0.005% or more, 0.02% or more, 0.1% or more, or 0.5% or more, based on dry weight of the yeast extract.

By allowing a γ-glutamyl transferase to act on the yeast extract containing γ-Glu-X obtained as described above in the same manner as that of the method described below, a yeast extract containing γ-Glu-X-Gly can be produced.

The second method in accordance with the presently described subject matter is a method for producing a yeast extract containing a peptide selected from γ-Glu-X and γ-Glu-X-Gly, which includes the steps of allowing a γ-glutamyl transferase to act on a yeast extract raw material to which an amino acid or a peptide such as X and X-Gly is added, wherein X represents an amino acid or an amino acid derivative other than Cys and derivatives thereof.

If a γ-glutamyl transferase is allowed to act on X or X-Gly, γ-Glu-X or γ-Glu-X-Gly is generated. Therefore, a yeast extract containing γ-Glu-X or γ-Glu-X-Gly can also be obtained by allowing a γ-glutamyl transferase to act on a yeast extract containing X or X-Gly. The yeast extract containing X and/or X-Gly may be prepared from a yeast cultured in a medium containing X and/or X-Gly, or may be obtained by adding X and/or X-Gly to a yeast extract raw material.

As the yeast extract raw material, a yeast extract obtained by a conventional method can be used.

One kind of X or X-Gly may be added to the yeast extract raw material, or an arbitrary mixture of two or more kinds of them may be added. X and/or X-Gly is added in a total amount of 1% or more, 5% or more, 10% or more, based on dry weight of the yeast extract raw material.

The reaction catalyzed by the γ-glutamyl transferase is performed in an aqueous solvent such as water or buffers. Specifically, for example, the yeast extract raw material is dissolved in the aqueous solvent, and the γ-glutamyl transferase is added. The reaction conditions can be suitably determined according to the γ-glutamyl transferase to be used. The reaction is usually allowed at pH 3 to 9 and 15 to 70° C. for 1 to 300 minutes, or pH 5 to 8 and 30 to 70° C. for 5 to 150 minutes.

Concentration of the yeast extract raw material in the aqueous solvent may be determined in view of ease of handling. The concentration is usually 0.1 to 50%, or 0.5 to 20%, in terms of dry weight of the yeast extract raw material.

Examples of the γ-glutamyl transferase include glutaminase, γ-glutamyl transpeptidase (γ-GTP), and so forth. As for the amount of the enzyme, in the case of γ-GTP, it is usually 0.001 to 1000 units/ml, 0.005 to 100 units/ml, y 0.01 to 25 units/ml, or 0.05 to 10 units/ml, wherein 1 unit is defined to be the activity of liberating 1.0 mmole of p-nitroaniline from γ-glutamyl-p-nitroanilide per 1 minute in a solution at pH 8.5 and 25° C. (definition described in Sigma General Catalogue, 2008-2009 Edition, p. 917). The amount of glutaminase can also be determined in a manner similar to that for γ-GTP.

After the enzymatic reaction, the γ-glutamyl transferase may be inactivated by, for example, a heat treatment at 80 to 100° C., but this is not always necessary.

As a substrate of the γ-glutamyl transferase, a γ-glutamyl compound, for example, GSH, may be added to the reaction mixture. GSH contained in the yeast extract may also be used as a substrate. In this case, a yeast extract prepared from yeast in which the content of GSH is increased, for example, a yeast in which activities or activity of Gsh1p and/or Gsh2p is enhanced can be used. Although a greater GSH content in the yeast extract is preferred, it is usually 1 to 50%, 1 to 30%, or 5 to 20%, based on dry weight of the yeast extract.

In such a manner as described above, a yeast extract in which the amount of γ-Glu-X, γ-Glu-X-Gly, or both is increased is obtained. The yeast extract can contain γ-Glu-X, γ-Glu-X-Gly or both in a total amount of 0.005% or more, 0.02% or more, 0.1% or more, or 0.5% or more, based on dry weight of the yeast extract.

The obtained yeast extract may be concentrated, or may be dried and thereby made into powdered form, if needed.

EXAMPLES

Hereinafter, the present invention will be explained more specifically with reference to the following non-limiting examples.

Example 1

Detection of γ-Glu-Val-Gly and γ-Glu-Val in Various Yeast Extracts

γ-Glu-Val-Gly, γ-Glu-Val, and Val-Gly contents in various commercially available yeast extracts were measured by fluorescence derivatization of the peptides with 6-aminoquinolyl-N-hydroxysuccinimidyl carbamate (AQC), and detection by LC-MS/MS according to the method described below. First, to 2.5 µL each of solutions of various yeast extracts diluted to an appropriate concentration, or 2.5 µL each of standard solutions containing γ-Glu-Val-Gly, γ-Glu-Val and Val-Gly, respectively, 2.5 µL of Milli-Q water, 5 µL of a 5 µM internal standard substance solution (L-alanine-3,3,3-d3, Sigma (Ala-D3), DL-valine-2,3,4,4,4,5,5,5-d8, Sigma (Val-d8), both are labeled with stable isotope), and 30 µL of a borate buffer (attached to AccQ-Fluor (registered trademark) Reagent Kit, Nihon Waters) were added. To each mixture, 10 µL of an AQC reagent solution (prepared by dissolving the reagent powder of the aforementioned reagent kit in 1 mL of acetonitrile) was added. This mixture was heated at 55° C. for 10 minutes, and then 100 µL of 0.1% formic acid aqueous solution was added to the mixture to prepare a sample for analysis.

Then, the sample for analysis prepared as described above was subjected to separation by the reverse phase liquid chromatography described below, and then introduced into a mass spectrometer. The separation conditions are as follows.

(1) HPLC: Agilent 1200 Series
(2) Separation column: Unison UK-Phenyl, internal diameter: 2.0 mm, length: 100 mm, particle size: 3 µm (Imtakt)
(3) Column temperature: 40° C.
(4) Mobile phase A: 25 mM Ammonium formate (pH 6.0 adjusted by aqueous ammonia)
(5) Mobile phase B: methanol
(6) Flow rate: 0.25 mL/min (7) Elution conditions: elution was performed by using mixtures of the mobile phase A and the mobile phase B. The ratios of the mobile phase B to the mixtures are as follows: 0 minute (5%), 0 to 17 minutes (5 to 40%), 17 to 17.1 minutes (40 to 80%), 17.1 to 19 minutes (80%), 19 to 19.1 minutes (80 to 5%), 19.1 to 27 minutes (5%).

Then, derivatized compounds of γ-Glu-Val-Gly, γ-Glu-Val, and Val-Gly eluted under the aforementioned separation conditions were introduced into a mass analyzer, and quantified by HPLC-MS chromatography. The analysis conditions are as follows.
(1) Mass analyzer: AB Sciex API3200 QTRAP
(2) Detection mode: Selected Ion Monitoring (positive ion mode)
(3) Selected ion: Table 1

TABLE 1

| Derivatized compound | First mass analyzer (Q1) | Second mass analyzer (Q3) |
| --- | --- | --- |
| γ-Glu-Val-Gly | 474.2 | 171.2 |
| γ-Glu-Val | 417.4 | 171.1 |
| Val-Gly | 345.4 | 171.1 |
| Ala-d3 | 263.0 | 171.1 |
| Val-d8 | 296.0 | 171.1 |

The derivatized compounds of γ-Glu-Val-Gly, γ-Glu-Val, and Val-Gly were quantified by using analysis software, Analyst ver. 1.4.2 (AB Sciex). As the internal standard substance for performing the quantification, derivatized compounds of Ala-d3 were used in the case of γ-Glu-Val-Gly and γ-Glu-Val, and a derivatized compound of Val-d8 was used in the case of Val-Gly, respectively. The results are shown in Table 2. In the table, "ND" means that the amount was below quantitation limit (the same shall apply to the following). The analysis results (HPLC-MS chromatograms) of derivatized internal standard amino acids, γ-Glu-Val-Gly, γ-Glu-Val, and Val-Gly standard samples are shown in FIG. 1.

TABLE 2

|  | γ-Glu-Val-Gly | γ-Glu-Val | Val-Gly |
| --- | --- | --- | --- |
| Brand A | ND | 0.3 ppm | 0.5 ppm |
| Brand B | ND | ND | ND |
| Brand C | 2.2 ppm | 19.2 ppm | 11.1 ppm |
| Brand D | ND | ND | 0.4 ppm |
| Brand E | 3.1 ppm | 25.9 ppm | 33.1 ppm |
| Brand F | ND | ND | 0.4 ppm |
| Brand G | 4.6 ppm | 38.3 ppm | 0.4 ppm |

As shown in Table 1, the amount of γ-Glu-Val-Gly in the various yeast extracts was several ppm at most. The amount of each of γ-Glu-Val and Val-Gly was on the order of several tens of ppm at most.

Example 2

Detection of γ-Glu-Val-Gly and γ-Glu-Val in Cells of Various Yeasts

Then, the intracellular content of γ-Glu-Val-Gly and γ-Glu-Val in various yeasts were measured. The *Saccharomyces cerevisiae* S288C strain was used as a standard, and the *Saccharomyces cerevisiae* AJ14819 strain (deposited as an international deposit as FERM BP-08502 strain) was used for it's high GSH content. The S288C strain is stored at the independent administrative agency, National Institute of Technology and Evaluation, Biological Resource Center (NBRC, NITE Biological Resource Center, 2-5-8 Kazusakamatari, Kisarazu-shi, Chiba-ken, 292-0818, Japan) with the number of NBRC1136, and can be provided therefrom. This strain is also stored at the American Type Culture Collection (12301 Parklawn Drive, Rockville, Md. 20852, United States of America) with the number of ATCC 26108, and can be provided therefrom. The AJ14819 strain was obtained by mutagenizing a monoploid yeast strain obtained from a commercially available *Saccharomyces cerevisiae* strain with EMS, and then selecting a mutant strain in which expression of the MET25 gene is not suppressed by methionine. The resulting strain was deposited at the independent administrative agency, Agency of Industrial Science and Technology, International Patent Organism Depository, Central 6, 1-1-1, Higashi, Tsukuba-shi, Ibaraki-ken, 305-8566, Japan) on Sep. 11, 2002, and assigned an accession number of FERM P-19007. Then, the deposit was converted to an international deposit under the provisions of the Budapest Treaty on Oct. 1, 2003, and assigned an accession number of FERM BP-08502 (Japanese Patent No. 4352877).

One loop of each of the aforementioned strains was inoculated into SD medium (50 ml in 500 ml-volume Sakaguchi flask), and cultured at 30° C. for 24 hours with shaking at a velocity of 120 rpm.

Composition of SD Medium:

| Glucose | 2% |
| --- | --- |
| Nitrogen Base | 1-fold concentration |

Nitrogen Base of 10-fold concentration was obtained by dissolving a mixture of 1.7 g of Bacto Yeast Nitrogen Base w/o Amino Acids and Ammonium Sulfate (Difco) and 5 g of ammonium sulfate in 100 ml of sterilized water, adjusting the solution to about pH 5.2, and sterilizing the solution by filter filtration.

Absorbance of the obtained culture broth was measured, the culture broth was inoculated into SD medium (400 ml in a 2 L-volume conical flask with baffle fins, a plurality of flasks) so that OD660 was 0.01 at the start of the culture (absorbance was measured by using DU640 SPECTROPHTOMETER, BECKMAN COULTER), and culture was performed at 30° C. for 19 hours with shaking by rotation at a velocity of 120 rpm. From the obtained culture broth, 400 OD units of the cells (1 OD unit is defined as cells contained in 1 ml of culture broth of which OD660 is 1) were collected by centrifugal separation. The supernatant was removed as much as possible, and the residual cells were suspended in 45 ml of Milli-Q water. The cells were collected again by centrifugal separation, and resuspended in 45 ml of Milli-Q water. By repeating this operation 3 times in total, the medium was completely removed from the cells. The washed cells were suspended in about 1.5 ml of Milli-Q water, and the suspension was heated at 70° C. for 10 minutes. By this step, the extractable components contained in the cells were extracted. Then, the extract and the cell residue were separated by centrifugation.

Cell debris were removed from the extract using a centrifugal filtration membrane of 10 kDa (Amicon Ultra—0.5 mL 10K, MILLIPORE, Catalogue Number UFC501096)), the obtained fraction was derivatized with the AQC reagent in the same manner as that used in Example 1, and γ-Glu-Val-Gly and γ-Glu-Val were measured by LC-MS/MS. Separately, the amount of GSH in the cells was measured in a conventional manner (GSH in the extract was derivatized by using a fluorescence reagent ABD-F that binds to thiol group, separated and quantified by HPLC). Furthermore, dry cell weight was measured after the washed cells were dried at 104° C. for 4 hours. From the amounts of γ-Glu-Val-Gly and γ-Glu-Val in the extract prepared from the cells that was contained in a certain volume of culture broth and dry cell weight measured as described above, the amount of these peptides based on weight of dried cells was calculated. The results are shown in Table 3.

TABLE 3

|  | γ-Glu-Val-Gly (ppm) | γ-Glu-Val (ppm) | GSH (%) |
|---|---|---|---|
| S288C | 1 | 3 | 0.43 |
| AJ14819 | 1 | 2 | 1.06 |

As a result, particular correlation between the γ-Glu-Val-Gly or γ-Glu-Val content and the GSH content was not observed.

Example 3

Addition of γ-Glu-Val-Gly to S288C strain (1)

One loop of the S288C strain was inoculated into the SD medium (50 ml in a 500 ml-volume Sakaguchi flask), and cultured at 30° C. for 24 hours with shaking at a velocity of 120 rpm. Absorbance of the obtained culture broth was measured, the culture broth was inoculated into SD medium (400 ml in a 2 L-volume conical flask with baffle fins, two or more flasks) so that OD660 was 0.01 at the start of the culture, and culture was performed at 30° C. for 16 hours with shaking by rotation at a velocity of 120 rpm. To the SD medium, γ-Glu-Val-Gly (purchased from Kokusan Chemistry) was added in advance at a final concentration of 100 ppm.

Using the above culture broth, content of γ-Glu-Val-Gly in dry cells was calculated in the same manner as in Example 2. As a result, the γ-Glu-Val-Gly content was about 20,000 ppm (=2%).

Furthermore, when the content of γ-Glu-Val-Gly in the washing solution was measured after various washing steps, the content was 0.01 ppm, i.e., below the quantitation limit, after centrifugation three times. The cells were washed once, and therefore it was confirmed that γ-Glu-Val-Gly in the medium was sufficiently removed in the washing process by four separation steps, and did not remain in the cell extract.

Example 4

Addition of γ-Glu-Val-Gly to S288C Strain (2)

One loop of the S288C strain was inoculated into SD medium (50 ml in a 500 ml-volume Sakaguchi flask), and cultured at 30° C. for 24 hours with shaking at a velocity of 120 rpm. Absorbance of the obtained culture broth was measured, the culture broth was inoculated into SD medium (400 ml in a 2 L-volume conical flask with baffle fins, two or more flasks) so that OD660 was 0.01 at the start of the culture, and culture was performed at 30° C. for 19 hours with shaking by rotation at a velocity of 120 rpm. After 19 hours, γ-Glu-Val-Gly aqueous solutions of various concentrations were added to obtain predetermined concentrations, and the culture was continued for 1 hour. Using these culture broths, the γ-Glu-Val-Gly content in dry cells was calculated in the same manner as in Example 2. Furthermore, the solid content of the extract was calculated, and the amount of γ-Glu-Val-Gly in the solid content was also calculated. The results are shown in Table 4.

TABLE 4

| Amount of γ-Glu-Val-Gly added to medium (ppm) | 0.01 | 0.1 | 1 | 5 | 10 | 100 |
|---|---|---|---|---|---|---|
| γ-Glu-Val-Gly content in dry cells (ppm) | 5 | 28 | 363 | 2647 | 5341 | 10191 |
| γ-Glu-Val-Gly content in solid content of extract (ppm) | 21 | 96 | 1110 | 10119 | 17408 | 32183 |

As a result, it was seen that as the amount of γ-Glu-Val-Gly increased, the γ-Glu-Val-Gly content in the dried cells and solid content of the extract increased.

Example 5

Production of Yeast Extract Containing γ-Glu-Val-Gly

A yeast extract was produced from yeast cells cultured with the addition of γ-Glu-Val-Gly. One loop of the S288C strain was inoculated into SD medium (50 ml in a 500 ml-volume Sakaguchi flask), and cultured at 30° C. for 24 hours with shaking at a velocity of 120 rpm. Absorbance of the obtained culture broth was measured, the culture broth was inoculated into SD medium (400 ml in a 2 L-volume conical flask with baffle fins, 12 flasks) so that OD660 was 0.01 at the start of the culture, and culture was performed at 30° C. for 19 hours with shaking by rotation at a velocity of 120 rpm. After 19 hours, a γ-Glu-Val-Gly aqueous solution was added at a final concentration of 50 ppm, and the culture was continued for 1 hour.

The cells were collected from the total culture broth, and washed in the same manner as that of Example 2. The washed cells in an amount of 400 OD units were suspended in 1.5 ml of Milli-Q water. This suspension was maintained at 70° C. for 10 minutes to produce an extract from the yeast cells. Furthermore, the suspension was centrifuged to remove the cell residues and thereby collect only the extract. The γ-Glu-Val-Gly concentration of this extract (extract of addition experiment) was measured to be about 300 ppm, and solid content was about 1%. The γ-Glu-Val-Gly concentration in an extract prepared in the same way but without adding γ-Glu-Val-Gly to the culture broth (extract of no addition experiment) was below the quantitation limit, and solid content was about 1%.

The extracts prepared as described above were evaluated for kokumi in the presence of MSG (sodium glutamate) as follows. As a control, an aqueous solution containing 0.2% MSG and 0.5% NaCl was used, and the organoleptic score thereof was defined to be 0.0. Then, an aqueous solution containing 0.2% MSG, 0.5% NaCl and 10 ppm of γ-Glu-Val-Gly was used as a standard solution for kokumi, and the organoleptic score thereof was defined to be 3.0. By using these two kinds of solutions as standards of kokumi intensity, the kokumi intensity of the extract was evaluated using an aqueous solution containing the extract, 0.2% MSG, and 0.5% NaCl as a test sample. The amount of the extract of the addition experiment in the test sample was adjusted so that the γ-Glu-Val-Gly concentration became 10 ppm. The amount of the extract of the no addition experiment was adjusted so that the solid content in the test sample was the same as that in the test sample of the extract of the addition experiment. That is, the γ-Glu-Val-Gly concentrations in the standard solution of kokumi and the test sample containing the extract of the addition experiment were equivalent, and the solid contents in the test sample containing the extract of the addition experiment and the test sample containing the extract of the no addition experiment were equivalent.

The test samples prepared as described above were evaluated for kokumi by four special panelists. As a result, all four of the panelists evaluated that kokumi obtained with the extract of the addition experiment was stronger than that obtained with the same concentration of γ-Glu-Val-Gly. Furthermore, kokumi was evaluated at different stages of tasting, that is, it was evaluated for initial and middle tastes and also for aftertaste. The averages of the scores of the four panelists for each type of kokumi were used as the evaluation scores. The results are shown in Table 5. The initial and middle tastes means the taste sensed at 0 to 4 seconds after eating, and the aftertaste means the taste sensed 5 seconds after eating and thereafter. As seen from these results, it is estimated that kokumi for initial and middle tastes and kokumi for aftertaste of the extract prepared by adding γ-Glu-Val-Gly during the culture process was enhanced, because γ-Glu-Val-Gly was metabolized in a certain manner, or because of synergism of γ-Glu-Val-Gly and a component in the yeast extract.

TABLE 5

|  | Evaluation score for kokumi for initial and middle tastes | Evaluation score for kokumi for aftertaste |
| --- | --- | --- |
| Control | 0.0 | 0.0 |
| Standard solution (10 mM γ-Glu-Val-Gly, 0.2% MSG, 0.5% NaCl) | 3.0 | 3.0 |
| Extract of addition experiment | 4.0 ± 0.1 | 3.9 ± 0.3 |
| Extract of no addition experiment | 2.5 ± 0.9 | 1.8 ± 0.6 |

Example 6

Addition of γ-Glu-Val to the S288C Strain (1)

One loop of the S288C strain was inoculated into SD medium (50 ml in a 500 ml-volume Sakaguchi flask), and cultured at 30° C. for 24 hours with shaking at a velocity of 120 rpm. Absorbance of the resulting culture broth was measured, the culture broth was inoculated into SD medium (400 ml in a 2 L-volume conical flask with baffle fins, two or more flasks) so that OD660 was 0.01 at the start of the culture, and culture was performed at 30° C. for 24 hours with shaking by rotation at a velocity of 120 rpm. To the SD medium, γ-Glu-Val (purchased from Bachem) was added in advance to a final concentration of 100 ppm. Using the culture broth, the amounts of γ-Glu-Val and γ-Glu-Val-Gly present in dry cells were calculated in the same manner as that of Example 2. The results are shown in Table 6.

TABLE 6

|  | γ-Glu-Val (ppm) | γ-Glu-Val-Gly (ppm) |
| --- | --- | --- |
| No addition | 3 | 0 |
| Addition of γ-Glu-Val | 7171 | 20 |

As a result, a part of γ-Glu-Val taken up into the yeast cells was converted into γ-Glu-Val-Gly.

Example 7

Addition of γ-Glu-Val to the S288C Strain (2)

One loop of the S288C strain was inoculated into SD medium (50 ml in a 500 ml-volume Sakaguchi flask), and cultured at 30° C. for 24 hours with shaking at a velocity of 120 rpm. Absorbance of the resulting culture broth was measured, the culture broth was inoculated into SD medium (400 ml in a 2 L-volume conical flask with baffle fins, two or more flasks) so that OD660 was 0.01 at the start of the culture, and culture was performed at 30° C. for 19 hours with shaking by rotation at a velocity of 120 rpm. After 19 hours, γ-Glu-Val aqueous solutions of various concentrations were added to obtain predetermined concentrations, and the culture was continued for 1 hour. Using these culture broths, the γ-Glu-Val content in the dry cells was calculated in the same manner as that of Example 2. Furthermore, the solid content of the extracted extract was calculated, and the amount of γ-Glu-Val in the solid content of the extract was also calculated. The results are shown in Table 7.

TABLE 7

| Amount of γ-Glu-Val added to medium (ppm) | 0 | 25 | 100 | 200 |
| --- | --- | --- | --- | --- |
| γ-Glu-Val content in dry cells (ppm) | 2 | 1468 | 6369 | 10930 |
| γ-Glu-Val content in solid content of extract (ppm) | 9 | 8491 | 27599 | 49474 |

As a result, as the addition amount of γ-Glu-Val increased, the γ-Glu-Val content in the dry cells and solid content of the extract increased.

Example 8

Addition of Val-Gly to the S288C Strain

One loop of the S288C strain was inoculated into SDP medium (ammonium sulfate used for the preparation of the SD medium was replaced with proline, final concentration of proline was 0.1 g/L, 50 ml in a 500 ml-volume Sakaguchi flask), and cultured at 30° C. for 24 hours with shaking at a velocity of 120 rpm. Absorbance of the resulting culture broth was measured, the culture broth was inoculated into SDP medium (400 ml in a 2 L-volume conical flask with baffle fins, two or more flasks) so that OD660 was 0.01 at the start of the culture, and culture was performed at 30° C. for 24 hours with shaking by rotation at a velocity of 120 rpm. To the SDP medium, Val-Gly (purchased from Bachem) was added in advance to a final concentration of 100 ppm. Using the culture broth, the amount of γ-Glu-Val-Gly in dry cells was calculated in the same manner as that of Example 2. The results are shown in Table 8.

TABLE 8

|  | γ-Glu-Val-Gly (ppm) |
| --- | --- |
| Val-Gly no addition experiment | 0 |
| Val-Gly addition experiment | 2 |

When Val-Gly was added to the medium, γ-Glu-Val-Gly accumulated in the yeast cells.

Example 9

Yeast Extract Obtained with Addition of Val-Gly on which γ-glutamyl Transferase was Made to Act A 1% aqueous solution of the yeast extract containing about 8% of GSH based on the solid content (yeast extract sample was prepared by adding reagent grade GSH into the commercially available yeast extract) was prepared, and adjusted to pH 7.0 with NaOH. To this solution, powdered Val-Gly was added to final concentrations in the aqueous solutions of 400 ppm, 800 ppm and 4000 ppm to prepare test samples. An aqueous solution of the yeast extract without addition of Val-Gly was also used as a control. To these test samples, a glutaminase (Glutaminase Daiwa SD-C100S, Daiwa kasei) was added at 1 mg/ml, and the enzymatic reaction was allowed at 37° C. for 120 minutes. Furthermore, γ-GTP (γ-Glutamyltranspeptidase from equine kidney, Sigma, Code G9270-100UN) was added at 0.05 mg/ml instead of the glutaminase, and the enzymatic reaction was similarly allowed at 37° C. for 120 minutes. The reaction mixtures were immediately cooled on ice, and the amounts of γ-Glu-Val-Gly, GSH and Cys-Gly were measured.

As a result, as shown in the following tables, very little γ-Glu-Val-Gly was generated in the Val-Gly no addition experiment, but as the addition amount of Val-Gly was increased, more γ-Glu-Val-Gly was generated. When γ-GTP was used, in particular, production of γ-Glu-Val-Gly was remarkable.

TABLE 9

Concentrations of components in reaction mixture observed with glutaminase

|  |  | γ-Glu-Val-Gly (ppm) | GSH (ppm) | Cys-Gly (ppm) |
|---|---|---|---|---|
| No addition | Before reaction | 0.0 | 835.6 | 6.3 |
|  | After reaction | 0.0 | 3.1 | 701.6 |
| 400 ppm | Before reaction | 0.0 | 862.4 | 9.9 |
|  | After reaction | 1.4 | 3.5 | 715.0 |
| 800 ppm | Before reaction | 0.0 | 851.5 | 6.7 |
|  | After reaction | 3.8 | 3.6 | 705.7 |
| 4000 ppm | Before reaction | 0.0 | 826.2 | 6.1 |
|  | After reaction | 16.0 | 3.4 | 683.3 |

TABLE 10

Concentrations of components in reaction mixture observed with γ-GTP

|  |  | γ-Glu-Val-Gly (ppm) | GSH (ppm) | Cys-Gly (ppm) |
|---|---|---|---|---|
| No addition | Before reaction | 0.0 | 813.6 | 5.2 |
|  | After reaction | 0.8 | 432.4 | 335.1 |
| 400 ppm | Before reaction | 0.0 | 824.6 | 4.5 |
|  | After reaction | 150.9 | 333.2 | 388.2 |
| 800 ppm | Before reaction | 0.0 | 836.9 | 6.1 |
|  | After reaction | 157.9 | 316.3 | 417.3 |
| 4000 ppm | Before reaction | 0.0 | 857.2 | 6.7 |
|  | After reaction | 340.5 | 180.8 | 462.6 |

If Val or nVal is added instead of Val-Gly, and the enzyme reaction is allowed to proceed in a similar manner, γ-Glu-Val or γ-Glu-nVal is also produced.

Indeed, the same experiments were executed by adding 4000 ppm Val, 800 ppm nVal, or 4000 ppm nVal to a final concentration instead of Val-Gly. Also in this experiment, the yeast extract prepared from *Candida utilis* was used as commercially available yeast extract. Moreover, dry matter of the reaction mixture was measured to calculate the amount of γ-Glu-Val or γ-Glu-nVal in the dry matter base. As a result, 0.239% γ-Glu-Val on the dry matter base of yeast extract was produced when 4000 ppm Val was added as a final concentration, 0.709% γ-Glu-nVal on the dry matter base of yeast extract was produced when 800 ppm nVal was added as a final concentration, and 1.029% γ-Glu-nVal on the dry matter base of yeast extract was produced when 4000 ppm nVal was added as a final concentration. The γ-Glu-nVal content was measured in the same manner described in the experimental example 1 by using 1 μM γ-Glu-nVal as a standard solution. The analysis result (HPLC-MS chromatogram) of derivatized γ-Glu-nVal standard sample is shown in FIG. 2.

Example 10

Addition of γ-Glu-Val to GSH2-Enhanced Strain

A GSH2 expression-enhanced strain can be bred by the following procedure.

1) Acquisition of Uracil Auxotrophic Strain (Ura3 Mutant) from the S288C Strain

A uracil auxotrophic strain can be obtained by spreading a *Saccharomyces cerevisiae* strain treated with a mutagen in a conventional manner on an agar medium containing 5-FOA, and selecting an ura3 mutant strain from the strains that grow (see, for example, METHODS IN YEAST GENETICS, 2000 EDITION, p. 179). A uracil auxotrophic strain can also be obtained by introducing an URA3-neighboring DNA except for the URA3 gene into the S288C strain, and disrupting the URA3 gene, as shown below.

First, a 500-bp upstream region of URA3 was amplified by PCR using the primers shown in SEQ ID NOS: 1 and 2, and the chromosomal DNA of the S288C strain as the template. Furthermore, a 500-bp downstream region of URA3 was also amplified using the primers shown in SEQ ID NOS: 3 and 4. As for PCR conditions, a cycle consisting of thermal denaturation at 94° C. for 10 seconds, annealing at 55° C. for 10 seconds, and extension at 72° C. for 1 minute was repeated 25 times. Then, overlap PCR was performed using the above two kinds of DNA fragments purified by ethanol precipitation as templates and the primers shown in SEQ ID NOS: 5 and 6 to obtain a 1-kb DNA fragment consisting of the 500-bp upstream region and 500-bp downstream region of the URA3 gene ligated together. The S288C strain was transformed with this DNA fragment, and then cultured overnight in the SD medium to which uracil was added, and the cells were applied to 5-FOA plate medium. The ura3Δ0 strain was obtained from the resulting transformants.

2) Preparation of a Template Plasmid for Promoter Substitution

First, the URA3 locus was amplified by PCR using the primers of SEQ ID NOS: 7 and 8 and the chromosomal DNA of a *Saccharomyces cerevisiae* wild-type strain as the template (thermal denaturation: 94° C. for 10 seconds, annealing: 50° C. for 10 seconds, extension: 72° C. for 1 minute, 25 cycles). The resulting DNA fragment was purified by ethanol precipitation, and then digested with SphI and EcoRI, and the product was inserted into the plasmid pUC19 at the SphI-EcoRI sites to obtain pUC19-URA3. Then, the PGK1 promoter region was amplified from the chromosomal DNA of the *Saccharomyces cerevisiae* wild-type strain using the primers shown in SEQ ID NOS: 9 and 10. This DNA fragment was digested with PstI, and inserted into pUC19-URA3 digested with PstI and treated with CIAP at the PstI site to obtain pUC19-PGK1p-URA3. In a similar manner, the PGK1 promoter amplified using the primers shown in SEQ ID NOS:

11 and 12 was digested with AatII, and inserted into pUC19-PGK1p-URA digested with AatII and treated with CIAP at the AatII site to obtain pUC19-PGK1p-URA3-PGK1p. When the nucleotide sequence of the prepared template plasmid was confirmed by sequencing, it was equivalent to the nucleotide sequence expected when using the chromosomal DNA of the S288C strain as the template. Therefore, even if the chromosomal DNA of the S288C strain is used as the template instead of chromosomal DNA of a wild-type strain, a similar plasmid can be prepared.

3) Introduction of PGK1 Promoter into GSH2 Gene on Chromosome

PCR is performed using the primer of SEQ ID NO: 13, which has a GSH2 upstream sequence at the 5' end, the primer of SEQ ID NO: 14, which has a part of a sequence in ORF starting from the start codon of the GSH2 gene, and pUC19-PGK1p-URA3-PGK1p as the template (thermal denaturation: 94° C. for 10 seconds, annealing: 60° C. for 10 seconds, extension: 72° C. for 4 minutes, 25 cycles) to prepare a DNA fragment having URA3 between PGK1 promoters. The ura3Δ0 strain can be transformed with this DNA fragment, and plated on an SD plate medium to obtain transformants, and a strain in which the GSH2 promoter is replaced with the PGK1 promoter-URA3-PGK1 promoter can be obtained from the transformants.

4) Elimination of URA3 Selective Marker and Substitution of Promoter for GSH2 Gene The strain in which the PGK1 promoter-URA3-PGK1 promoter substitutes for the GSH2 promoter is cultured overnight in a uracil-supplemented SD medium, and an appropriate volume of the culture is applied to 5-FOA plate medium. From colonies that appeared, a strain in which URA3 is removed by homologous recombination between the introduced PGK1 promoters, and the GSH2 promoter is replaced with the PGK1 promoter, can be obtained. Furthermore, by introducing a DNA amplified using a wild-type genome as the template and the primers of SEQ ID NOS: 15 and 16 into the above strain, a strain with a genotype that is the same as that of the ura3Δ0 strain except that URA3 is returned to wild-type, and the GSH2 promoter is replaced with the PGK1 promoter, can be obtained.

A yeast extract is produced from the strain obtained as described above, and evaluated in the same manner as described in Examples 3, 4, and 6 to 8.

Example 11

Addition of a γ-Glu-Val-Gly to HGT1-Enhanced Strain

An HGT1 expression-enhanced strain can be obtained in the same manner as described in Example 10. Specifically, by performing PCR using pUC19-PGK1p-URA3-PGK1p as a template, the primer of SEQ ID NO: 17, which has a GSH1 upstream sequence at the 5' end, and the primer of SEQ ID NO: 18, which has a part of a sequence in ORF starting from the start codon of the GSH11 gene, and introducing the obtained DNA fragment into sporulating yeast, cells in which the promoter of GSH11 is replaced with the PGK1 promoter are obtained.

A yeast extract is produced from the strain obtained as described above, and evaluated in the same manner as described in Examples 3, 4, and 6 to 8.

Example 12

Evaluation of γ-Glu-Val-Gly Uptake Activity of HGT1 or PRT2 Modified Strain

The influence of Hgt1p, which has been considered to be a GSH specific transporter, and Ptr2p, which is a peptide transporter, on γ-Glu-Val-Gly accumulation was evaluated as follows.

1) The Acquisition of Uracil Auxotrophic Mutant (Ura3 Mutant) from S288C

Figure 2A:
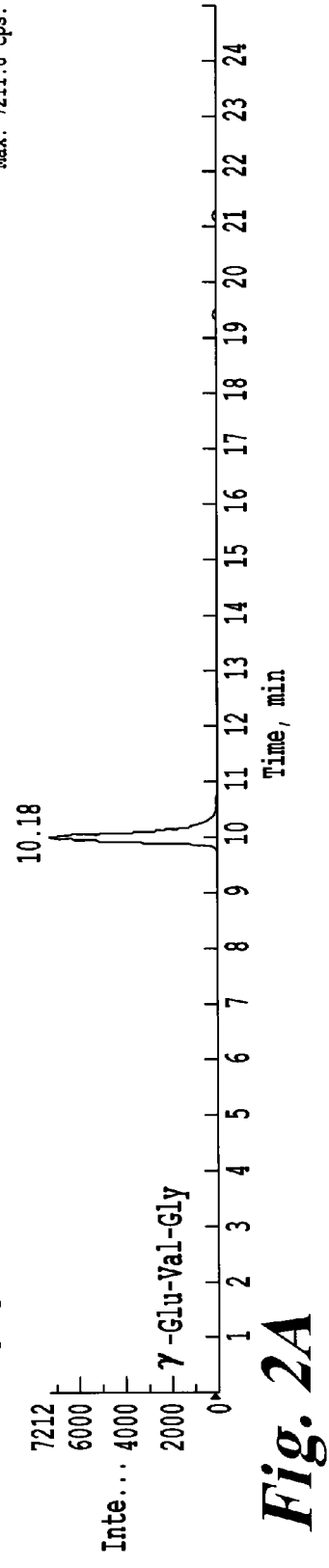
FIG. 2 shows HPLC-MS chromatograms of γ-Glu-Val-Gly, γ-Glu-Val, Val-Gly, γ-Glu-nVal-Gly, and γ-Glu-nVal standard samples.
Figure 2B:
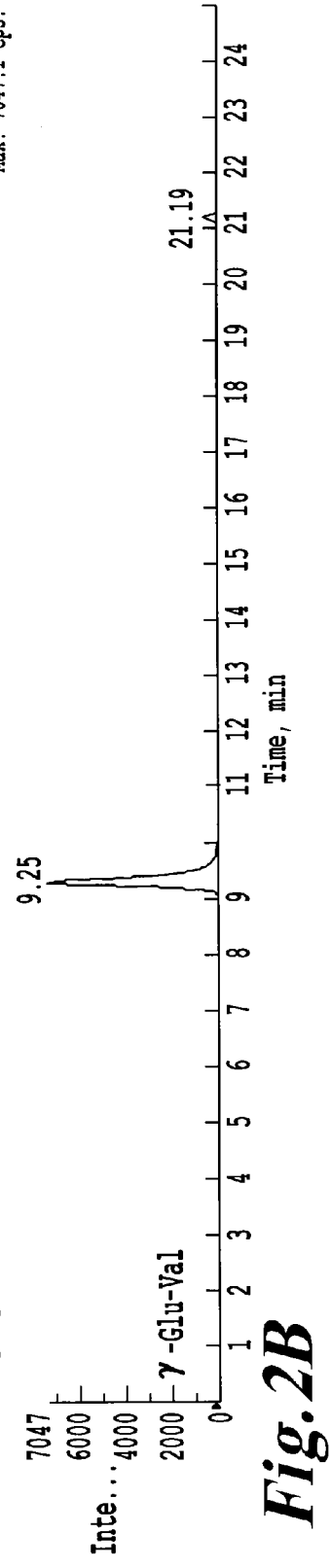
Figure 2C:
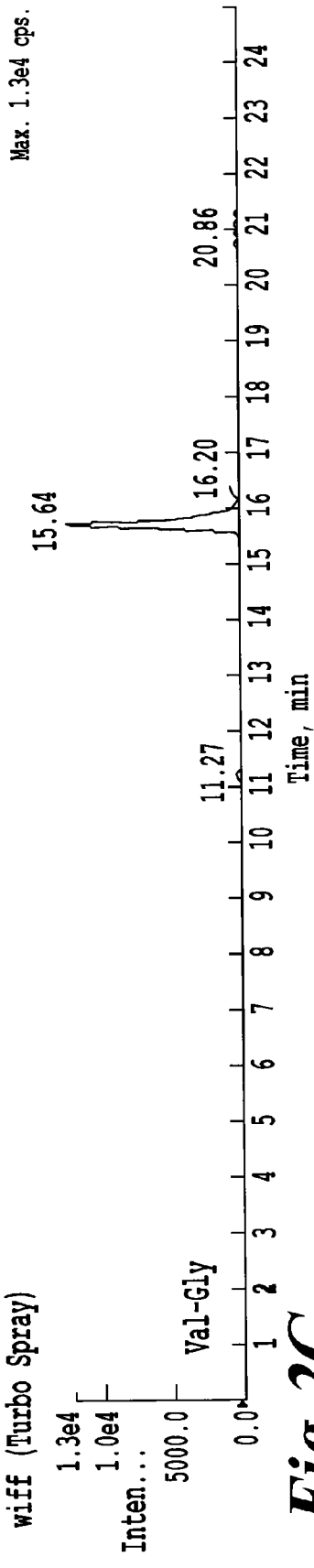
Figure 2D:
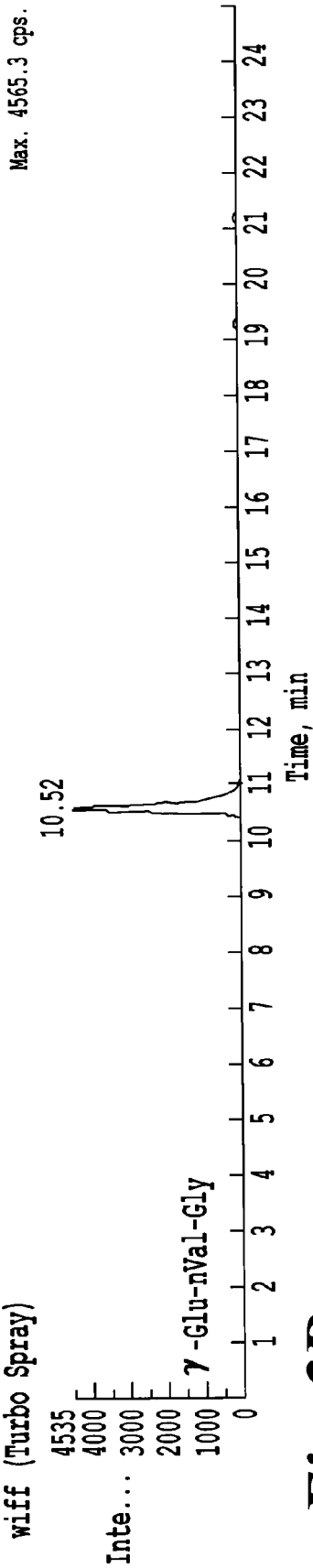
Figure 2E:
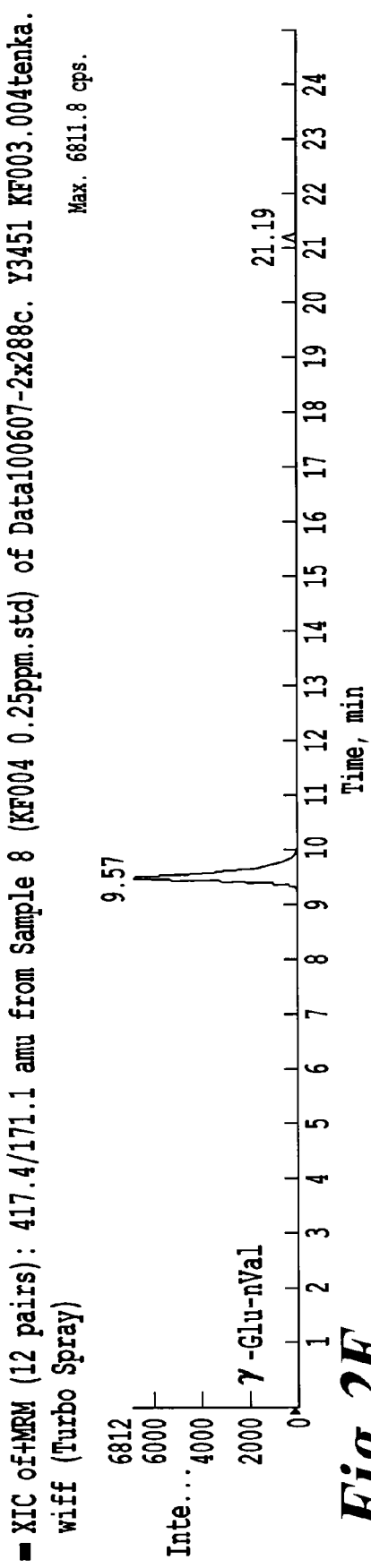
Figure 3:
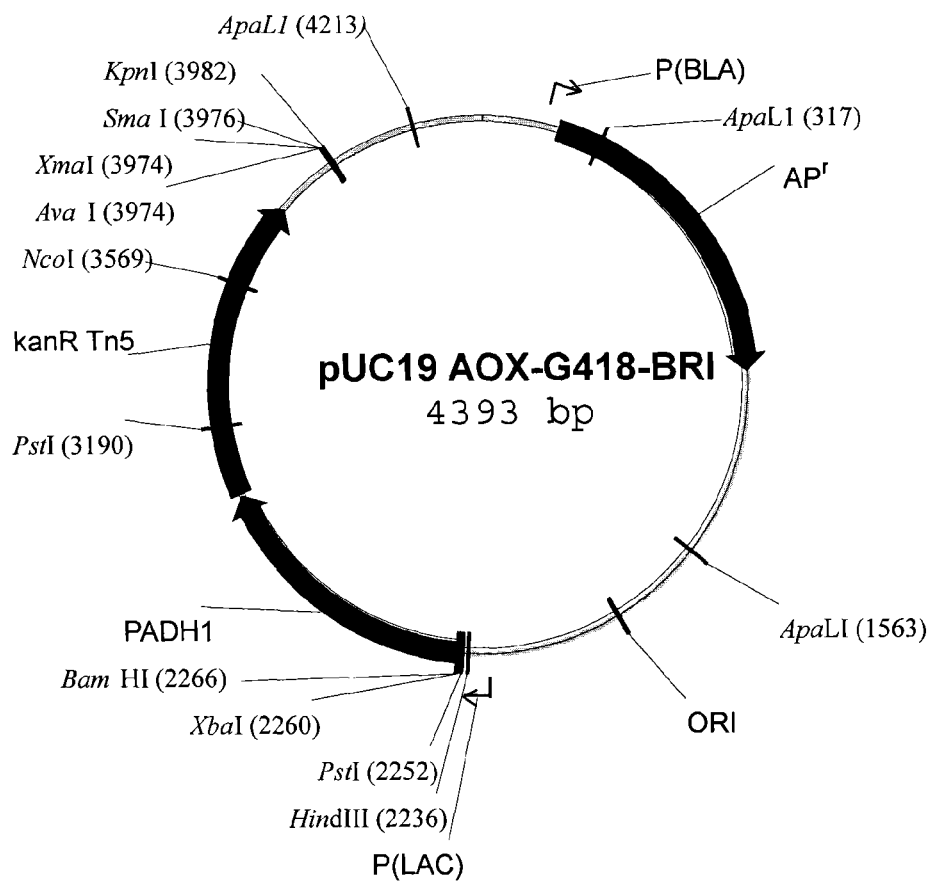
FIG. 3 shows the structure of the plasmid pUC19AOX-G418-BRI.

The geneticin (G418)-resistance cassette ($P_{ADH1}$-kanR) was amplified by PCR using pUC19AOX-G418-BRI (FIG. 3, SEQ ID NO: 23, Olga A. et al., Mol. Biotechnol., Pubslished online Dec. 19, 2010)) as the template and primers URA3 Km-L1 (SEQ ID NO: 24) and URA3 Km-R2 (SEQ ID NO: 25). The plasmid pUC19AOX-G418-BRI consists of the kanamycin resistant gene (neo) from E. coli transposon Tn5 under control of S. cerevisiae ADH1 (ADC1) promoter cloned in pUC19 vector. BR1 means that in this plasmid the BamHI and EcoRI sites, which are present in parental pUC19AOX-G418 between $P_{ADH1}$ and kaznR, were deleted. The $P_{ADH1}$-kanR cassette or its equivalent can be obtained by PCR using the plasmid pKat7 (Lang-Hinrichs, C. et al., 1989. Applied Microbiology and Biotechnology. 30:388-394) or pUM2 (Merckelbach A, et al., 1993, Appl Microbiol Biotechnol. November; 40:361-364) instead of pUC19AOX-G418-BRI as a template and the above described primers URA3Km-L1 and URA3Km-R2.

40 nucleotides at 5'-end of primer URA3 Km-L1 are homologous to the URA3 upstream region, and 40 nucleotides at 5'-end of primer URA3 Km-R2 are complementary to the URA3 downstream region.

The resulting DNA fragment was used for transformation of S. cerevisiae S288C. Transformants were selected on YPD plates containing 200 μg/ml of G418. Deletion of the URA3 gene was verified by PCR with primers ura3up2 (SEQ ID NO: 26) and ura3dn2 (SEQ ID NO: 27).

The resulting strain was S288C ura3Δ0::$P_{ADH1}$-kanR. It may also be referred to as S288C ura3Δ0. This strain was used to construct a HGT1 or PTR2 overxpressing strain.

Figure 4:
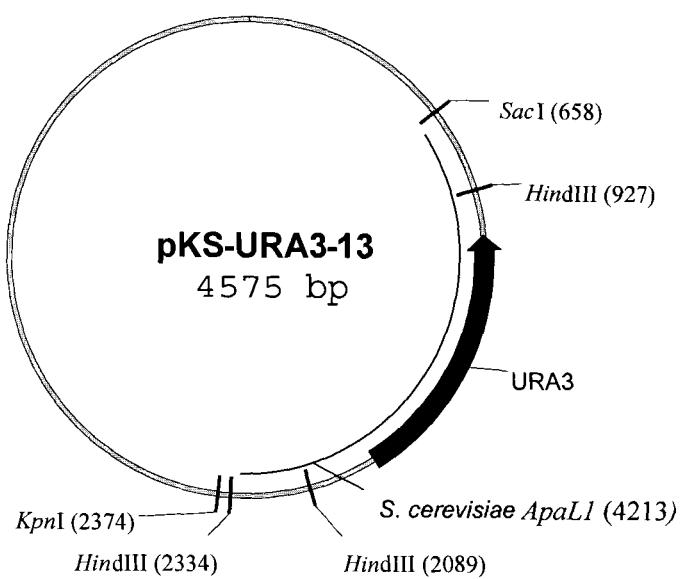
FIG. 4 shows the structure of the plasmid pKS-URA3-13.

On the other hand, another uracil auxotrophic mutant was acquired as follows in order to use it to construct a strain in which HGT1 or PTR2 is deleted. A fragment which contains URA3 with promoter and terminator regions was amplified by PCR using chrojmosomal DNA of S288C as the template and the aforementioned primers ura3up2 and ura3dn2. This fragment was cloned into the SmaI site of pBluescript II KS (+), and its structure was confirmed by sequencing analysis. The resulting plasmid was referred to as pKS-URA3-13 (FIG. 4, SEQ ID NO: 28).

Figure 5:
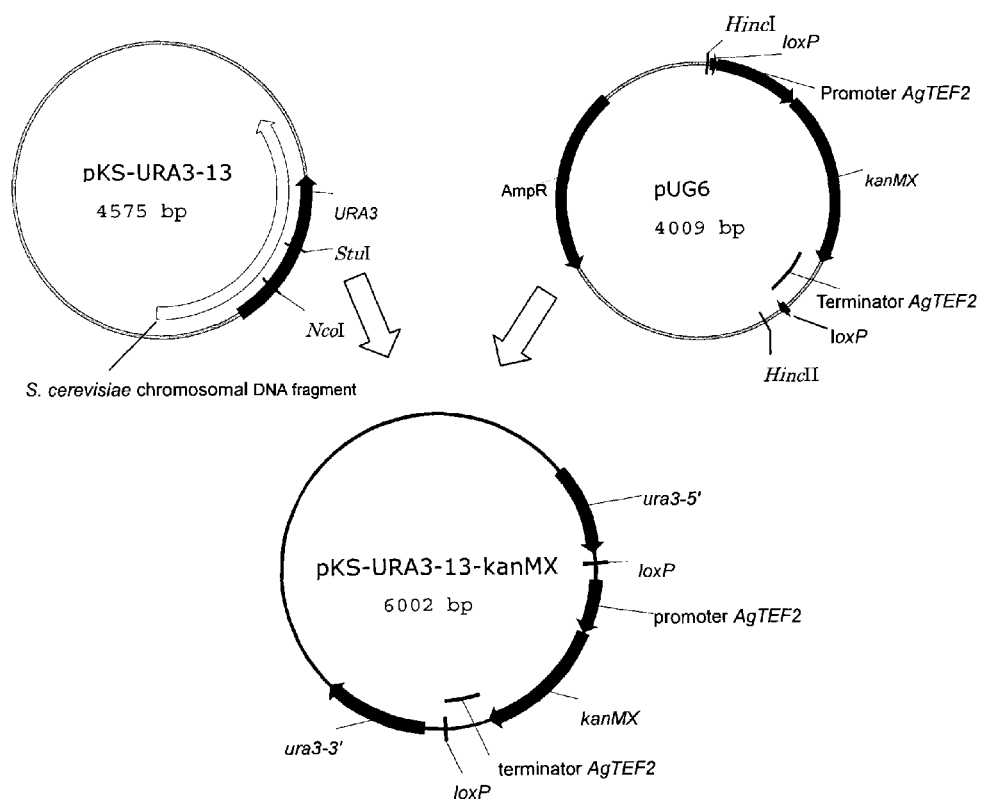
FIG. 5 shows construction of the plasmid pKS-URA3-13-kanMX.

Plasmid pKS-URA3-13 was digested with StuI and NcoI, and then treated with Klenow fragment to blunt-end the NcoI site. The resulting 4.38-kb fragment was ligated with the 1.64-kb HincII-HincII fragment from pUG6 [Güldener, U., Heck, S., Fiedler, T., Beinhauer, J., and Hegemann, J.H.1996. A new efficient gene disruption cassette for repeated use in budding yeast. Nucleic Acids Research 24, 2519-2524], containing a loxP-kanMX-loxP module. The resulting plasmid was referred to as pKS-URA3-13-kanMX. Its map and scheme of construction is shown in FIG. 5, SEQ ID NO: 29.

Then, the kanMX gene flanked by URA3 fragments was amplified by PCR using the aforementioned primers ura3up2 and ura3dn2, and pKS-URA3-13-kanMX as the template. The resulting fragment was used for transformation of S. cerevisiae S288C strain, and then transformants were selected on YPD medium containing 200 μg/ml of G418. As a result, a S288C derivative strain with deletion of 227 nucleotides of coding region of URA3 was obtained. This deletion was referred to as ura3Δ227::loxP-kanMX-loxP. To delete the kanMX marker, the resulting strain was transformed with plasmid pSH47 [Güldener, U., Heck, S., Fiedler, T., Beinhauer, J., and Hegemann, J.H.1996. A new efficient gene disruption cassette for repeated use in budding yeast. Nucleic Acids Research 24, 2519-2524], containing a gene encoding Cre-recombinase under the control of the GAL1 promoter and URA3 as a selective marker. Marker excision occurred after induction of Cre-recombinase synthesis by shifting cells from the YPD medium to YPG (containing galactose). The resulting strain from which the plasmid pSH47 had been deleted was designated S288C ura3Δ227::loxP.

2) Acquisition of HGT1 Deletion Mutant

DNA fragment containing an Agleu2-CaURA3-Agleu2 cassette was amplified by PCR using plasmid pAG61 [Goldstein, A. L., Pan, X., and McCusker, J.H.1999. Heterologous URA3MX cassettes for gene replacement in *Saccharomyces cerevisiae*. Yeast 15, 507-511] as the template and primers hgt1-pUG6u (SEQ ID NO: 30) and hgt1-pUG6d (SEQ ID NO: 31). The Agleu2-CaURA3-Agleu2 cassette contains *Candida albicans* URA3 gene under control of *Ashbya gossypii* TEF promoter and terminator, surrounded with two identical fragments of *Ashbya gossypii* LEU2 gene. Each of the LEU2 gene fragments is a 470 bp sequence spanning from C-terminal region to 3' UTR of the gene. The Agleu2-CaURA3-Agleu2 cassette is excisable from the plasmid pAG61.

47 nucleotides at the 5'-end of primer hgt1-pUG6u are homologous to the HGT1 5'-region, and 44 nucleotides at the 5'-end of the primer hgt1-pUG6d are complementary to the HGT1 3'-region.

The resulting fragment was used for transformation of the S288C ura3Δ227::loxP strain. Transformants were selected on plates containing SD medium. The resulting strain S288C ura3Δ227::loxP hgt1Δ1981::Agleu2-CaURA3-Agleu2, in which nucleotides at position 1981 to 2400 of the coding region of the HGT1 gene was deleted, was referred to as S288C hgt1Δ.

The deletion of the HGT1 gene was verified by PCR using the primers hgt1-51 (SEQ ID NO: 32) and hgt1-32 (SEQ ID NO: 33).

3) Acquisition of PTR2 Deletion Mutant

Figure 6:
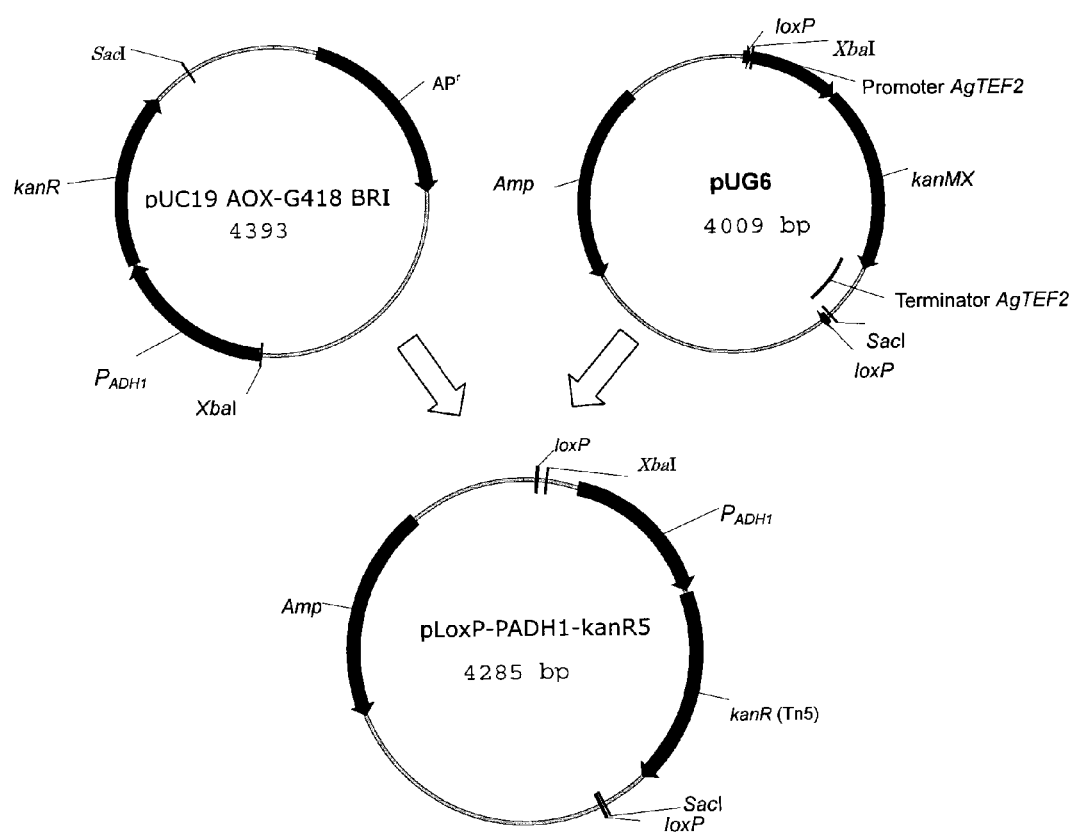
FIG. 6 shows construction of the plasmid pLoxP-PADH1-kanR5.

The $P_{ADH1}$-kanR module from plasmid pUC19AOX-G418-BRI was excised with XbaI and SacI and subcloned into the same sites of plasmid pUG6. The resulting plasmid was referred to as pLoxP-PADH1-kanR5 (FIG. 6).

A DNA fragment containing the loxP-$P_{ADH1}$-kanR-loxP module was amplified by PCR using the pLoxP-PADH1-kanR5 plasmid as the template and primers ptr2-pUG6u (SEQ ID NO: 34) and ptr2-pUG6d (SEQ ID NO: 35).

47 nucleotides at the 5'-end of primer hgt1-pUG6u are homologous to the PTR2 5'-region, and 44 nucleotides at the 5'-end of primer hgt1-pUG6d are complementary to the PTR23'-region.

The resulting fragment was used for transformation of S288C ura3Δ227::loxP strain. Transformants were selected on plates containing YPD medium with 200 μg/ml of G418. The resulting strain S288C ura3Δ227::loxP ptr2Δ967::loxP-$P_{ADH1}$-kanR-loxP, in which nucleotides at postions 422 to 1388 of the coding region of the PTR2 gene are deleted, is referred to as S288C ptr2Δ.

The deletion of the PTR2 gene was verified by PCR using primers ptr2-51 (SEQ ID NO: 36) and ptr2-31 (SEQ ID NO: 37).

4) Acquisition of the HGT1 and PTR2 Deletion Mutant from the S288C Strain

The strain S288C hgt1Δ ptr2Δ was constructed in a manner similar to the S288C ptr2Δ strain, but the strain S288C hgt1Δ was used for transformation.

5) Acquisition of an Hgt1p Overproducing Strain

Figure 7:
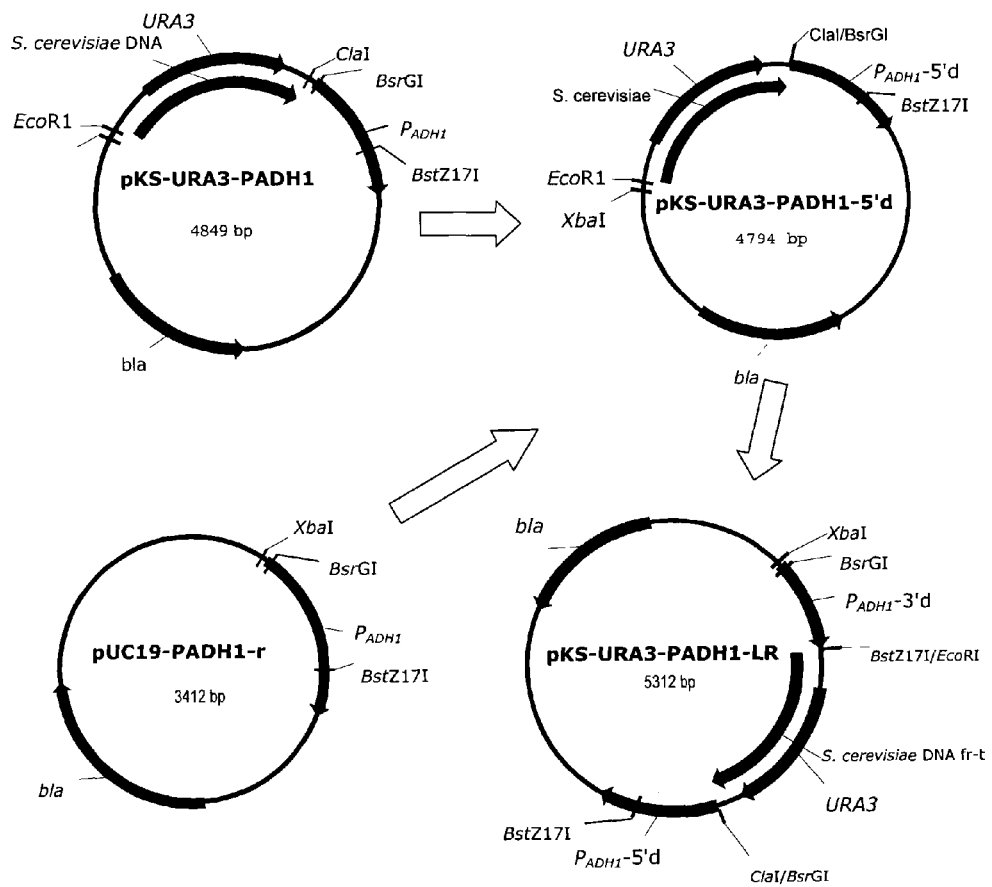
FIG. 7 shows construction of the plasmid pKS-URA3-PADH1-LR.

A DNA fragment containing the promoter of ADH1 was amplified by PCR using chromosomal DNA of *S. cerevisiae* strain S288C as the template and primers adh1L1 (SEQ ID NO: 38) and adh1R1 (SEQ ID NO: 39). The resulting fragment was cloned into the SmaI site of plasmid pUC19 and its structure was confirmed by sequence analysis. The resulting plasmid was referred to as pUC19-PADH1-r (FIG. 7).

Figure 8:
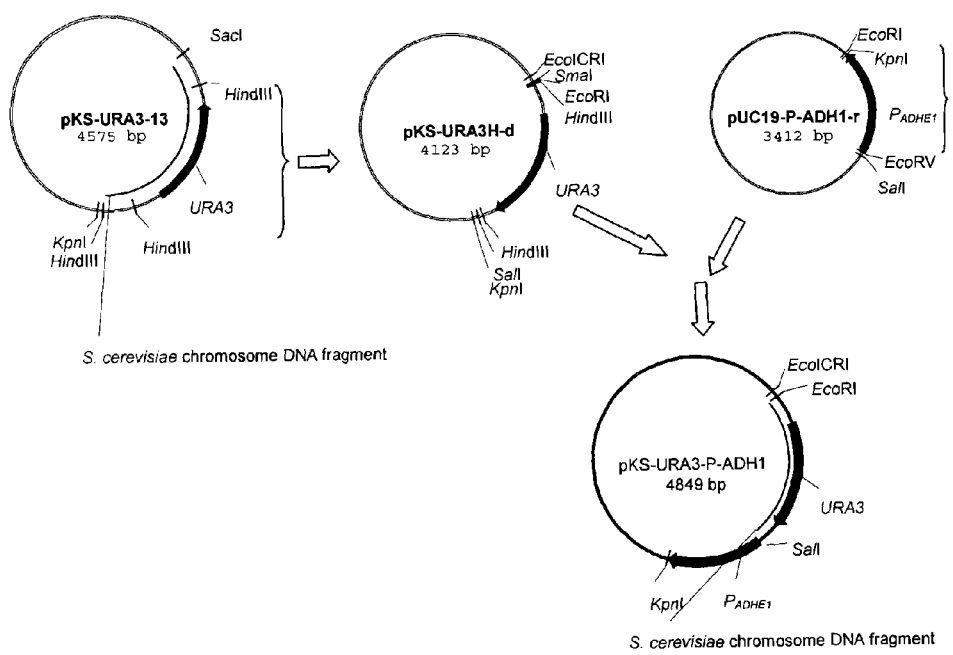
FIG. 8 shows construction of the plasmid pKS-URA3-P-ADH1.

The HindIII-HindIII fragment (1.16 kb) from the plasmid pKS-URA3-13 was subcloned into the HindIII site of the plasmid pBluescript II KS(+) yielding pKS-URA3H-d. The KpnI-SalI fragment from the plasmid pUC19-PADH1-r was cloned into the SalI-KpnI sites of pKS-URA3H-d. The resulting plasmid was referred to as pKS-URA3-P-ADH1 (FIG. 8).

Then, plasmid pKS-URA3-PADH1 was digested with ClaI and BsrGI. The digested plasmid was blunt-ended with Klenow fragment and self-ligated. The resulting plasmid, referred to as pKS-URA3-PADH1-5' d, was digested with EcoPJ, treated with Klenow fragment, and then digested with)(bal. The resulting fragment was ligated with a fragment of $P_{ADH1}$, and excised from plasmid pUC19-PADH1-r with XbaI and BstZ17I. The resulting plasmid was referred to as pKS-URA3-PADH1-LR (FIG. 7).

A DNA fragment containing a $P_{ADH1}$-URA3-$P_{ADH1}$ cassette was amplified by PCR using the plasmid pKS-URA3-PADH1-LR as the template and primers PADH1-HGT1 (SEQ ID NO: 40) and HGT1-PADH1 (SEQ ID NO: 41).

40 nucleotides at the 5'-end of primer PADH1-HGT1 are complementary to the first 40 nucleotides of the HGT1 coding region, and 40 nucleotides at the 5'-end of primer HGT1-PADH1 are homologous to the HGT1 upstream region.

A DNA fragment containing the HGT1 upstream region was amplified by PCR using chromosomal DNA of *S. cerevisiae* strain S288C as the template and primers hgt53 (SEQ ID NO: 42) and hgt33 (SEQ ID NO: 43).

Then, fragments obtained as described above were fused by PCR using primers hgt53 and PADH1-HGT1 as it was described in Shevchuk, N. A., Bryksin, A. V., Nusinovich, Y. A., Cabello, F. C., Sutherland M., Ladisch S. 2004. Construction of long DNA molecules using long PCR-based fusion of several fragments simultaneously. Nucleic Acids Res. 32(2):e19. The resulting fragment was used for transformation of strain S288C ura3Δ0::$P_{ADH1}$-kanR. Transformants were selected on plates containing SD medium. As a result, the strain S288C ura3Δ0::$P_{ADH1}$-kanR $P_{ADH1}$-URA3-$P_{ADH1}$-HGT1 was obtained. It was referred to as S288C $P_{ADH1}$-HGT1.

Figure 9:
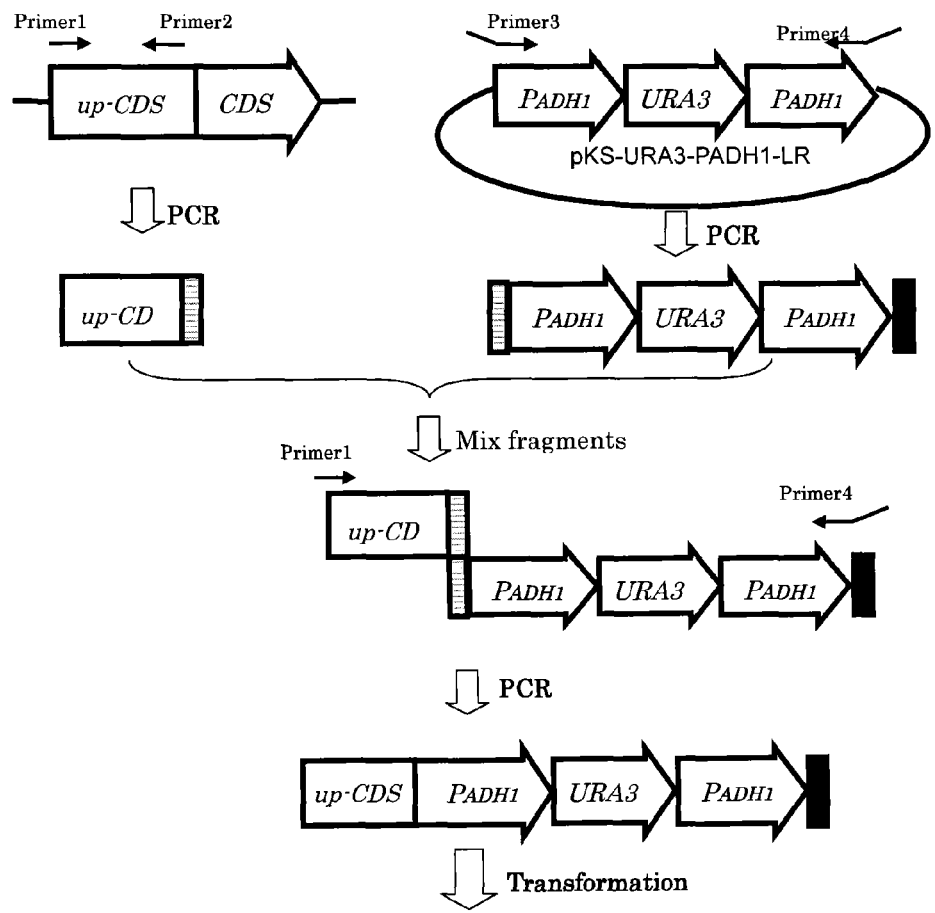
FIG. 9 shows preparation of a DNA fragment used for promoter substitution.

The scheme for the promoter replacement experiment is provided in FIG. 9. Primer hgt53 corresponds to Primer1, primer hgt33 corresponds to Primer2, primer HGT1-PADH1 corresponds to Primer3, primer PADH1-HGT1 corresponds to Primer4.

6) Acquisition of Ptr2p Overproducing Strain

Replacement of the native promoter of PTR2 was carried out in a manner similar to the replacement of the promoter of HGT1 (FIG. 9).

Primers Used:
ptr52 (SEQ ID NO: 44), correspond to Primer1;
ptr32 (SEQ ID NO: 45), correspond to Primer2;
PTR2-PADH1 (SEQ ID NO: 46), correspond to Primer4;
PADH1-PTR2 (SEQ ID NO: 47), correspond to Primer3;

40 nucleotides at the 5'-end of primer PADH1-PTR2 are complementary to the first 40 nucleotides of the PTR2 coding region, and 30 nucleotides at the 5'-end of the primer PTR2-PADH1 are homologous to the PTR2 upstream region.

7) Evaluation of Mutants

Each strain was cultivated in 50-ml tubes containing 5 ml of SD medium with 100 ppm γ-Glu-Val-Gly as a final concentration. Tubes were inoculated by overnight culture of the corresponding strain at initial $OD_{600}$=0.5, and placed in a rotation shaker at 240 rpm, 30° C. The cultivation time was 7 hours. Then, cells from 2 ml of broth culture were harvested by centrifugation, and were washed with 1 ml of milliQ water three times. Then, washed cells were suspended in 1 ml of milliQ and were incubated at 70° C. for 10 min with a water bath to extract intracellular materials. After cell debris and the extract were separated by centrifugation, the aqueous phase was transferred to a clean vial and the vial was then vacuum-dried. Thus, a dried extract was prepared. Then, the amount of γ-Glu-Val-Gly in the dried extract was measured with LC-MS/MS analysis. The detailed procedures are described below.

Equipment:
Mass spectrometer: Triple Quadrupole Agilent 6410
HPLC: Agilent 1200
Columns: Thermo Hypersil-Keystone C18 100 mm*2.1 mm*5 μm 1. Sample was dissolved in 100 μl of water, and then 100 μl of acetonitrile (MeCN) was added, and then centrifuged.
2. 190 μl of supernatant was transferred to a new tube and dried.
3. Pellet was dissolved in 40 μl of water.
4. For derivatization, 20 μl of the obtained solution was mixed with 60 μl of buffer and 80 μl of derivatization reagent, and incubated at 55° C. for 10 min.
5. After incubation, 200 μl of 0.1% solution of HCOOH in water was added to stop AQC derivatization reaction.

40 μl of the resultingsolution was taken for HPLC, and γ-Glu-Val-Gly in the elutants was analyzed with MS/MS detector.

HPLC Conditions:
mobile phase A—0.1% HCOOH in $H_2O$
mobile phase B—0.1% HCOOH in MeCN.
Flow rate—0.250 ml/min

TABLE 11

Gradient conditions:

| Time, min | mobile phase A | mobile phase B |
|---|---|---|
| 0 | 95 | 5 |
| 0.5 | 95 | 5 |
| 30 | 75 | 25 |
| 35 | 20 | 80 |
| 40 | 20 | 80 |
| 41 | 95 | 5 |

TABLE 12

Detecting conditions in Mass spectrometer

| Compound | Precursor ion (m/z) | Product ion (m/z) |
|---|---|---|
| γ-Glu-Val-Gly | 474.2 | 304.2 |
|  |  | 300.1 |
|  |  | 229.0 |

With these data, the amount of intracellular γ-Glu-Val-Gly was caluculated. The results are shown in Tables 13 and 14. It was shown that the HGT1 gene is essential to transport γ-Glu-Val-Gly from the medium, but PTR2 is not.

TABLE 13 evaluation of HGT1 and/or PTR2 deleting strains

| Strain | $OD_{600}$ | γ-Glu-Val-Gly (mg $l^{-1}$ $OD_{600}^{-1}$) |
|---|---|---|
| S288C | 3.3 | 1.93 |
| S288C hgt1Δ | 3.3 | 0.01 |
| S288C ptr2Δ | 3.8 | 1.84 |
| S288C hgt1Δ ptr2Δ | 3.4 | 0.01 |

TABLE 14 evaluation of Hgt1p or Ptr2p overproducing strains

| Strain | $OD_{600}$ | γ-Glu-Val-Gly (mg $l^{-1}$ $OD_{600}^{-1}$) |
|---|---|---|
| S288C | 3.40 | 3.3 |
| S288C $P_{ADH1}$-HGT1 | 1.64 | 28.6 |
| S288C $P_{ADH1}$-PTR2 | 2.64 | 2.6 |

Example 13

Effect of the Addition of γ-Glu-Val-Gly to a Hgt1p Overproducing Strain

The S288C $P_{ADH1}$-HGT1, Hgt1p overproducing strain obtained in Example 12, and its parental strain S288C, were evaluated for their ability to take up γ-Glu-Val-Gly in the same manners as described in Example 4. The amount of γ-Glu-Val-Gly added into the medium was 100 ppm as a final concentration. As a result, intracellular content of γ-Glu-Val-Gly in S288C on the dry weight cell was about 0.9%, but intracellular content of γ-Glu-Val-Gly in S288C $P_{ADH1}$-HGT1 on the dry weight cell was about 4.9%. This result confirms the effect of Hgt1p overproduction.

Example 14

Effect of the Addition of γ-Glu-nVal-Gly to S288C Strain

γ-Glu-nVal-Gly uptake ability of S288C was evaluated in the same manner as described in example 4. γ-Glu-nVal-Gly was added into the medium in advance at a final concentration of 10 ppm or 100 ppm. The γ-Glu-nVal-Gly content was measured in the same manner described in experimental example 1 by using 1 μM γ-Glu-nVal-Gly as a standard solution instead of γ-Glu-Val-Gly. As a result, the γ-Glu-nVal-Gly content in the dry cell was under the quantitative limit when γ-Glu-nVal-Gly was not added into the medium, but γ-Glu-nVal-Gly content in the dry cell was about 0.07% when γ-Glu-nVal-Gly was added into the medium at a final concentration of 10 ppm, and γ-Glu-nVal-Gly content in the dry cell was about 0.09% when γ-Glu-nVal-Gly was added into the medium at a final concentration of 100 ppm. The analysis result (HPLC-MS chromatogram) of derivatized γ-Glu-nVal-Gly standard sample is shown in FIG. 2.

Example 15

Effect of the Addition of γ-Glu-nVal to S288C Strain

γ-Glu-nVal uptake ability of S288C was evaluated in the same manner as described in example 7. To the SD medium, γ-Glu-nVal was added in advance at a final concentration of 10 ppm or 100 ppm. And the γ-Glu-nVal content was measured in the same manner described in the experimental example 1 by using 1 μM γ-Glu-nVal as a standard solution instead of γ-Glu-Val. As a result, the γ-Glu-nVal content in the dry cell was under the quantitative limit when γ-Glu-nVal was not added into the medium, but γ-Glu-nVal content in the dry cell was about 0.03% when γ-Glu-nVal was added into the medium at a final concentration of 10 ppm, and γ-Glu-nVal content in the dry cell was about 0.13% when γ-Glu-nVal was added into the medium at a final concentration of 100 ppm.

Example 16

Production of Yeast Extract Containing γ-Glu-nVal-Gly

A yeast extract was produced from yeast cells cultured with addition of γ-Glu-nVal-Gly in the same manner as described in example 5. One loop of the S288C strain was inoculated into SD medium (50 ml in a 500 ml-volume Sakaguchi flask), and cultured at 30° C. for 24 hours with shaking at a velocity of 120 rpm. Absorbance of the resulting culture broth was measured, the culture broth was inoculated into SD medium (400 ml in a 2 L-volume conical flask with baffle fins, 12 flasks) so that OD660 was 0.01 at the start of the culture, and culture was performed at 30° C. for 19 hours with shaking by rotation at a velocity of 120 rpm. After 19 hours, a γ-Glu-nVal-Gly solution was added to a final concentration of 50 ppm, and the culture was continued for 1 hour.

The cells were collected from the obtained total culture broth, and washed in the same manner as described in Example 2. The washed cells in an amount of 400 OD units were suspended in 1.5 ml of Milli-Q water. This suspension was maintained at 70° C. for 10 minutes to produce an extract from the yeast cells. Furthermore, the suspension was centrifuged to remove the cell residues and thereby collect only the extract. The γ-Glu-nVal-Gly concentration of this extract (extract of addition experiment) was measured to be about 100 ppm, and the solid content was about 1%. The γ-Glu-nVal-Gly concentration of an extract prepared by the same operation without adding γ-Glu-nVal-Gly to the culture broth (extract of no addition experiment) was below the detection limit, and the solid content was about 1%.

The extracts prepared as described above were evaluated for kokumi in the presence of MSG (sodium glutamate) as follows. As a control, an aqueous solution containing 0.2% MSG and 0.5% NaCl was used, and the organoleptic score thereof was defined to be 0.0. Then, an aqueous solution containing 0.2% MSG, 0.5% NaCl and 1 ppm of γ-Glu-nVal-Gly was used as a standard solution for kokumi, and the organoleptic score thereof was defined to be 3.0. By using these two kinds of solutions as standards of kokumi intensity, kokumi intensity of the extract was evaluated. The kokumi intensity of the extracts was evaluated using an aqueous solution containing the extract, 0.2% MSG and 0.5% NaCl as a test sample. The amount of the extract of the addition experiment in the test sample was adjusted so that the γ-Glu-nVal-Gly concentration became 1 ppm. The amount of the extract of the no addition experiment was adjusted so that the solid content in the test sample was the same as that in the test sample of the extract of the addition experiment. That is, the γ-Glu-nVal-Gly concentrations in the standard solution of kokumi and the test sample containing the extract of the addition experiment were equivalent, and the solid contents in the test sample containing the extract of the addition experiment and the test sample containing the extract of the no addition experiment, were equivalent. Moreover, a model sample was prepared by adding a γ-Glu-nVal-Gly solution into the extract of no addition experiment so as to be at an equivalent concentration of γ-Glu-nVal-Gly as compared to the extract of addition experiment. Therefore the γ-Glu-nVal-Gly concentration contained in the model sample was about 100 ppm, and the solid content was about 1%.

The test samples prepared as described above were evaluated for kokumi by four special panelists. As a result, all four of the panelists evaluated that kokumi obtained with the extract of the addition experiment was stronger than that obtained with the same concentration of γ-Glu-nVal-Gly. Furthermore, kokumi was evaluated for initial and middle tastes, and for aftertaste. Averages of the scores of the four panelists for each taste point of kokumi were used as the evaluation scores. The results are shown in Table 15. The initial and middle tastes means the taste at 0 to 4 seconds after eating, and the aftertaste means the taste 5 seconds after eating and thereafter. As seen from these results, it is estimated that kokumi for initial and middle tastes and kokumi for aftertaste of the extract prepared by adding γ-Glu-nVal-Gly during the culture process was enhanced, because γ-Glu-nVal-Gly was metabolized in a certain manner, or because of synergism of γ-Glu-nVal-Gly and a component in the yeast extract.

TABLE 15

|  | Evaluation score for kokumi for initial and middle tastes | Evaluation score for kokumi for aftertaste |
|---|---|---|
| Control | 0.0 | 0.0 |
| Standard solution (1 mM γ-Glu-nVal-Gly, 0.2% MSG, 0.5% NaCl) | 3.0 | 3.0 |
| Extract of addition experiment | 4.2 ± 0.7 | 3.6 ± 0.5 |
| Extract of no addition experiment | 1.1 ± 0.9 | 1.1 ± 0.9 |
| Model sample | 3.3 ± 0.2 | 3.3 ± 0.2 |

Example 17

Effect of Addition of γ-Glu-nVal-Gly to an Hgt1p Overproducing Strain

S288C $P_{ADH1}$-HGT1, Hgt1p overproducing strain obtained in Example 12, and its parental strain S288C were evaluated for their γ-Glu-nVal-Gly uptake abilities in the same manners as described in Example 4 and Example 13. The amount of γ-Glu-nVal-Gly added to the medium was 100 ppm as a final concentration. As a result, intracellular content of γ-Glu-Val-Gly in S288C on the dry weight cell was about 0.09%, but intracellular content of γ-Glu-nVal-Gly in S288C $P_{ADH1}$-HGT1 on the dry weight cell was about 2.84%.

Example 18

Effect of Addition of Val-Gly to a Ptr2p Overproducing Strain

S288C $P_{ADH1}$-HGT1, Hgt1p overproducing strain obtained in Example 12, S288C $P_{ADH1}$-PTR2, Ptr2p overproducing strain obtained in Example 12, and their parental strain S288C were evaluated for their γ-Glu-Val-Gly producing abilities from Val-Gly. Each strain was cultivated in 50-ml tubes containing 10 ml of SD medium with 100 ppm Val-Gly as a final concentration. Tubes were inoculated by overnight culture of corresponding strain at initial $OD_{600}$=0.01, and placed in rotation shaker at 240 rpm, 30° C. Cultivation time was for 20 hours. Then, cells from 2 ml of broth culture were harvested by centrifugation, and washed with 1 ml of milliQ water three times. Then, washed cells were suspended in 1 ml of milliQ and incubated at 70° C. for 10 min with a water bath to extract intracellular materials. After cell debris and the extract were separated by centrifugation, the aqueous phase was transferred to a clean vial and then the vial was vacuum-dried. Thus, the dried extract was prepared. Then γ-Glu-Val-Gly in the dried extract was measured with LC-MS/MS analysis as described in Example 12. As seen from the results, PTR2 seems to be a transporter of Val-Gly from the medium, and was effective to increase cellular γ-Glu-Val-Gly content from Val-Gly.

TABLE 16 evaluation of Hgt1p or Ptr2p overproducing strains

| Strain | $OD_{600}$ | γ-Glu-Val-Gly ($\mu g\ l^{-1}\ OD_{600}^{-1}$) |
|---|---|---|
| S288C | 3.38 | 0.04 |
| S288C $P_{ADH1}$-HGT1 | 3.96 | 0.03 |
| S288C $P_{ADH1}$-PTR2 | 1.86 | 8.89 |

Example 19

Effect of Addition of nVal to a GSH1 Overexpressing Strain

S288C strain was cultivated in SDP medium in the same manner as the Val-Gly no addition experiment described in Example 8. Then, cellular γ-Glu-nVal-Gly and γ-Glu-nVal were measured but were below the detection limit Therefore, the effect of addition of nVal to the GSH1 overexpressing strain was evaluated.

First of all, GSH1 overexpressing strain was constructed as described below.
1) Acquisition of Uracil Auxotrophic Strain (Ura3 Mutant) of a *Saccharomyces cerevisiae* Wild Type Strain Uracil auxotrophic strain (ura3 mutant) was obtained in the same manner described in Example 10, but a *Saccharomyces cerevisiae* wild type strain (MAT a type haploid strain) was used instead of S288C strain. The resulting strain was given a private number AJ14956, and was deposited at the independent administrative agency, Agency of Industrial Science and Technology, International Patent Organism Depository (Tukuba Central 6, 1-1, Higashi 1-chome, Tsukuba-shi, Ibaraki-ken, 305-8566, Japan) on Aug. 18, 2010, and assigned an accession number of FERM P-22000. Then, the deposit was converted to an international deposit under the provisions of the Budapest Treaty on Nov. 17, 2010, and assigned an accession number of FERM BP-11299.
2) Acquisition of GSH1 Overexpressing Strain Template plasmid pAUA (Olga, A. S. et al, 2010, Mol Biotechnol, published on line; 19 Dec. 2010, DOI 10.1007/s12033-010-9362-6) was used to substitute the native promoter of GSH1 with the promoter of ADH1. Then, the native promoter of GSH1 in AJ14956 was replaced with the promoter of ADH1 as we reported previously (Olga, A. S. et al, 2010). Then, the deleted URA3 gene was returned to the wild-type strain in the same manner as described in Example 10. Thus, a GSH1 overexpressing strain AG1 was obtained, which was, of course, non-auxotrophic to uracil.

Then, this AG1 strain was cultivated in SD medium supplemented with nVal. More specifically, one loop of the AG1 strain was inoculated into SD medium (50 ml in a 500 ml-volume Sakaguchi flask), and cultured at 30° C. for 24 hours with shaking at a velocity of 120 rpm. Absorbance of the obtained culture broth was measured, and the culture broth was inoculated into SDP medium (400 ml in a 2 L-volume conical flask with baffle fins, two or more flasks) so that OD660 was 0.01 at the start of the culture, and culture was performed at 30° C. for 23 hours with shaking by rotation at a velocity of 120 rpm. After 23 hours, nVal solution was added to a final concentration of 10 ppm or 100 ppm, and the cultures were continued for 1 hour. Then, the amount of γ-Glu-nVal was measured in the same manner described in the experimental example 15. The γ-Glu-nVal content was 0.07% when 10 ppm of nVal was added to the medium and the γ-Glu-nVal content was 0.37% when 100 ppm of nVal was added to the medium. Then, yeast extract containing γ-Glu-nVal was prepared from the broth culture cultivated with 100 ppm nVal basically in the same manner as described in Example 16. This yeast extract contained 1.44% γ-Glu-nVal at the dry matter base. This yeast extract would give strong kokumi for initial and middle taste from its character.

Example 20

Effect of Addition of γ-Glu-Val to a GSH2 Overexpressing Strain (1)

GSH2 overexpressing strain PG2 was constructed basically in the same manner as described in Example 10 except that AJ14956 described in Example 19 was used instead of ura3Δ0 from S288C. As a control, WT strain was obtained by returning the deleted URA3 gene into wild type gene from AJ14956 in the same manner described in Example 10 and Example 19.

One loop of the WT strain or PG2 strain was inoculated into SD medium (50 ml in a 500 ml-volume Sakaguchi flask), and cultured at 30° C. for 24 hours with shaking at a velocity of 120 rpm. Absorbance of the obtained culture broth was measured, and the culture broth was inoculated into the SD medium supplemented with various concentrations of γ-Glu-Val (400 ml in a 2 L-volume conical flask with baffle fins, two or more flasks) so that OD660 was 0.01 at the start of the culture, and culture was performed at 30° C. with shaking by rotation at a velocity of 120 rpm until OD660 reached to the predetermined value. Then, the amount of γ-Glu-Val-Gly in dry cells and the solid content of the extracted extract were calculated in the same manner described previously. As shown in the results, PG2, a GSH2 overexpressing strain, took up γ-Glu-Val from the medium and converted it into γ-Glu-Val-Gly in the cell.

TABLE 17 evaluation of GSH2 overexpressing strain

| Strain | γ-Glu-Val in the medium | CT (hr) | $OD_{660}$ | γ-Glu-Val-Gly content in dry cells (ppm) | γ-Glu-Val-Gly content in solid content of extract (ppm) |
|---|---|---|---|---|---|
| WT | 0 ppm | 19 | 1.67 | 0 | 0 |
| WT | 100 ppm | 19 | 1.79 | 7 | 29 |
| WT | 500 ppm | 19 | 1.69 | 7 | 29 |
| PG2 | 0 ppm | 21 | 1.68 | 0 | 0 |
| PG2 | 100 ppm | 21 | 1.74 | 81 | 384 |
| PG2 | 500 ppm | 21 | 1.65 | 123 | 585 |

Example 21

Effect of Addition of γ-Glu-Val to GSH2 Overexpressing Strain (2)

1) Preparation of Template Plasmid with Excisable kanMX Marker and TDH3 Promoter The DNA fragment containing promoter of the TDH3 gene, encoding the glyceraldehyde 3-phosphate dehydrogenase, was amplified by PCR, using the chromosomal DNA of S288C strain as a template, and tdh3-EcoR1 (SEQ ID NO: 48) and tdh3-Pci1 (SEQ ID NO: 49) primers (thermal denaturation: 94° C. for 20 seconds, annealing: 50° C. for 20 seconds, extension: 72° C. for 30 seconds, 30 cycles). Resulting fragment was cloned into SmaI site of pUC57 vector. The plasmid where promoter of TDH3 gene was orientated in direction from HindIII site to EcoRI site was selected and referred to as pUC57-PTDH3. The structure of cloned DNA fragment was confirmed by sequence analysis.

The NdeI-SalI DNA fragment of pUC57-PTDH3 was cloned into NdeI-SalI sites of pUG6 (Güldener, U., Heck, S., Fiedler, T., Beinhauer, J., and Hegemann, J. H. 1996. A new efficient gene disruption cassette for repeated use in budding yeast. Nucleic Acids Research 24, 2519-2524). Resulting plasmid was referred to as pUG6-PTDH3 (FIG. 10).

2) Substitution of GSH1 and GSH2 Native Promoters with Promoter of TDH3

The loxP-kanMX-loxP-$P_{TDH3}$ cassette was amplified by PCR using the pUG6-PTDH3 as a template and GSH1-pUG (SEQ ID NO: 50) and PTDH3-GSH1 (SEQ ID NO: 51) primers (thermal denaturation: 94° C. for 20 seconds, annealing: 48° C. for 60 seconds, extension: 72° C. for 120 seconds, 2 cycles; 94° C. for 20 seconds, annealing: 65° C. for 20 seconds, extension: 72° C. for 120 seconds, 20 cycles). Resulting DNA fragment was used for transformation of S288C strain. Transformants were selected on YPD medium containing 200 μg/ml of G418. As a result, the S288C derivative strain with promoter of GSH1 gene replaced with promoter of TDH3 was obtained (S288C loxP-kanMX-loxP-$P_{TDH3}$-GSH1 strain). The ura3 derivative of this strain (S288C ura3 loxP-kanMX-loxP-$P_{TDH3}$-GSH1 strain) was obtained then, by selection on 5-FOA containing medium according to conventional method (see, for example, METHODS IN YEAST GENETICS, 2000 EDITION, p. 179). The kanMX marker was deleted from resulting strain by means of transformation by pSH47 plasmid, as it is described in Example 12. As a result the S288C ura3 loxP-$P_{TDH3}$-GSH1 strain was obtained.

The native promoter of GSH2 gene was then replaced with promoter of TDH3. For this purpose, the loxP-kanMX-loxP-$P_{TDR3}$ cassette was amplified by PCR using the pUG6-PTDH3 as a template and PTDH3-GSH2 (SEQ ID NO: 52) and GSH2-pUG (SEQ ID NO: 53) primers (thermal denaturation: 94° C. for 20 seconds, annealing: 48° C. for 60 seconds, extension: 72° C. for 120 seconds, 2 cycles; 94° C. for 20 seconds, annealing: 65° C. for 20 seconds, extension: 72° C. for 120 seconds, 20 cycles). The GSH2 upstream region was amplified by PCR using chromosomal DNA of S288C strain as a template and GSH2up2 (SEQ ID NO: 54) and GSH2d_tail (SEQ ID NO: 55) primers (thermal denaturation: 94° C. for 20 seconds, annealing: 48° C. for 20 seconds, 72° C. for 30 seconds, 30 cycles). The resulting fragments were fused by means of overlap extension PCR (Shevchuk, N. A. at al. 2004. Construction of long DNA molecules using long PCR-based fusion of several fragments simultaneously. Nucleic Acids Res. 32(2):e19) using GSH2up2 (SEQ ID NO: 54) and PTDH3-GSH2 (SEQ ID NO: 52) primers (thermal denaturation: 94° C. for 20 seconds, annealing: 55° C. for 20 seconds, 72° C. for 120 seconds, 30 cycles). Resulting DNA fragment was used for transformation of S288C ura3 loxP-$P_{TDH3}$-GSH1 strain. Transformants were selected on YPD medium containing 200 μg/ml of G418. As a result, S288C ura3 loxP-$P_{TDH3}$-GSH1 loxP-kanMX-loxP-$P_{TDH3}$-GSH2 strain was obtained. Then, the kanMX marker was deleted from this strain as was described above, and the S288C ura3 loxP-$P_{TDH3}$-GSH1 loxP-$P_{TDH3}$-GSH2 strain was obtained. It was referred to as Y3560.

3) Construction of GSH2 Overexpressed Plasmid

The $P_{TDH3}$-GSH2 construction was amplified using Y3560 chromosomal DNA as a template and yepgsh2-F (SEQ ID NO: 56) and yepgsh2-R (SEQ ID NO: 57) primers. The 45 nucleotides of 5' sequences of these primers were complementary to regions flanking the SmaI-BamHI fragment in YEp24 plasmid (FIG. 11). Then the YEp24 plasmid was digested with SmaI and BamHI and the larger of the resulting fragments were isolated by means of agarose gel electrophoresis. The resulting $P_{TDH3}$-GSH2 and YEp24 fragments were mixed and used for transformation of S288C ura3Δ227::loxP and Y3560 strains. Transformants were selected on SD medium. Resulting plasmid was referred to as YEp24-PTDH3-GSH2, and resulting strains were referred to as S288C ura3Δ227/YEp24-PTDH3-GSH2 and Y3560/YEp24-PTDH3-GSH2, respectively.

4) Evaluation of Mutants

Each of the S288C ura3Δ227/YEp24-PTDH3-GSH2, Y3560/YEp24-PTDH3-GSH2, S288C and Y3560 strains, was cultivated in 50-ml tubes containing 10 ml of SD medium with 100 ppm γ-Glu-Val as a final concentration. For Y3560 strain medium was also supplemented with uracil (20 mg/L). Tubes were inoculated by overnight culture of corresponding strain at initial $OD_{600}$=0.01, and placed in rotation shaker at 240 rpm, 30° C. for 18 hours. Then cells from 2 ml of broth culture were harvested by centrifugation, and were washed by 1 ml of milliQ water three times. Then washed cells were suspended in 1 ml of milliQ and were incubated at 70° C. for 10 min with a water bath to extract intracellular materials. After cell debris and the extract were separated by centrifugation, aqueous phase was transferred to clean vial and then the vial was vacuum-dried. Thus the dried extract was prepared. Then γ-Glu-Val-Gly in the dried extract was measured with LC-MS/MS analysis as it is described in example 12. The results are shown in Table 18.

As shown in the results, GSH2 overexpressing strains converted γ-Glu-Val into γ-Glu-Val-Gly in the cell.

TABLE 18

The influence of YEp24-PTDH3-GSH2 on γ-EV to γ-EVG conversion

| Strain | $OD_{600}$ | γ-EVG, μg $l^{-1}$ $OD_{600}^{-1}$ |
|---|---|---|
| S288C | 3.1 | 6 |
| S288C ura3Δ227/YEp24-PTDH3-GSH2 | 3.0 | 705 |
| Y3560 | 2.7 | 110 |
| Y3560/YEp24-PTDH3-GSH2 | 2.5 | 2039 |

The invention claimed is:

1. A method for producing a yeast extract containing a peptide selected from the group consisting of γ-Glu-X and γ-Glu-X-Gly, which comprises culturing a yeast in a medium containing a peptide selected from the group consisting of γ-Glu-X, γ-Glu-X-Gly and X-Gly, and preparing a yeast extract from the obtained cells,
    wherein X of the γ-Glu-X represents an amino acid or an amino acid derivative selected from the group consisting of Val, Ile, Ser, Thr, Met, Asn, Gln, Pro, Asp, Lys, Arg, His, Phe, Tyr, Trp, and derivatives thereof,
    wherein X of the γ-Glu-X-Gly represents an amino acid or an amino acid derivative other than Cys and derivatives thereof.

2. The method according to claim 1 wherein the medium contains 0.1 ppm or more of the peptide, and the yeast extract contains the peptide selected from the group consisting of γ-Glu-X and γ-Glu-X-Gly in a total amount of 0.005% or more based on dry weight of the yeast extract.

3. The method according to claim 1 or 2, wherein X is Val.

4. The method according to claim 1 or 2, wherein X is nVal.

5. The method according to claim 1 or 2, wherein the yeast has been modified so that uptake of the peptide into cells is improved.

6. The method according to claim 5, wherein the activity of Hgt1p of the yeast has been enhanced.

7. The method according to claim 5, wherein the activity of Ptr2p of the yeast has been enhanced.

8. The method according to claim 5, wherein the activity of glutathione synthetase of the yeast has been enhanced.

9. A method for producing a yeast extract containing γ-Glu-nVal, which comprises culturing a yeast in a medium containing nVal.

10. The method according to claim 9, wherein the activity of γ-glutamylcysteine synthetase of yeast has been enhanced.

11. The method according to claim 1 or 2, wherein the yeast is *Saccharomyces cerevisiae*.

12. A yeast extract produced by the method according to claim 1 or 2.

13. The method according to claim 3, wherein the yeast has been modified so that uptake of the peptide into cells is improved.

14. The method according to claim 3, wherein the activity of Hgt1p of the yeast has been enhanced.

15. The method according to claim 3, wherein the activity of Ptr2p of the yeast has been enhanced.

16. The method according to claim 3, wherein the yeast is *Saccharomyces cerevisiae*.

17. The yeast extract according to claim 12, wherein X is Val.

18. The yeast extract according to claim 12, wherein the yeast is *Saccharomyces cerevisiae*.

* * * * *